United States Patent [19]

Dearth et al.

[11] 4,159,874
[45] * Jul. 3, 1979

[54] OPTICAL PROPERTY MEASUREMENT SYSTEM AND METHOD

[75] Inventors: Leonard R. Dearth, Appleton; Fred P. Lodzinski, Port Edwards, both of Wis.

[73] Assignee: Nekoosa Papers Inc., Port Edwards, Wis.

[*] Notice: The portion of the term of this patent subsequent to Nov. 16, 1993, has been disclaimed.

[21] Appl. No.: 706,827

[22] Filed: Jul. 19, 1976

Related U.S. Application Data

[63] Continuation-in-part of Ser. No. 438,993, Feb. 4, 1974, Pat. No. 3,992,190.

[51] Int. Cl.² .................... G01N 21/53; G01N 21/30; G01J 3/50
[52] U.S. Cl. .................... 356/73; 250/571; 356/418; 356/419
[58] Field of Search .................... 356/51, 73, 188–189, 356/199–203, 209; 250/571; 162/263

[56] References Cited

U.S. PATENT DOCUMENTS

| 3,762,817 | 10/1973 | Harklau | 356/73 |
| 3,827,808 | 8/1974 | Cho | 356/199 |
| 4,019,819 | 4/1977 | Lodzinski | 356/176 |

FOREIGN PATENT DOCUMENTS 323718  2/1972  U.S.S.R. .................... 356/200

OTHER PUBLICATIONS

Aminco-Bowman "Spectrophotofluorometer" Instruction & Service Manual, Instructions #768, American Instrument Co., Wash., D.C. 10-1958, pp. 1–2.
Springer, G., "A Light Transmission Type On-Line Opacity Meter", Tappi, 3-1971, pp. 411–412.
King, J.A.E. "Colour Measurement", Paper Technology 7-1973, pp. 21–24.
Hunter, R. S. "New Reflectometer & its use for Whiteness Measurement", Jr. Optical Soc. America, vol. 50, 1-1960, pp. 44–48.
Norman et al., "New Optical Techniques", Paper Technology, 2-1973, pp. 17–21.
Hunter, R. S. "Achieving Accuracy in Measurements of Textiles for Reflectance & Whiteness", American Dyestuff Reporter, vol. 50, 10-16-61, pp. 45–53.
Rutledge, W. C. "Extended Outputs from a System with an On-Line Tristimulus Colorimeter & a Digital Computer", Tappi, 7-1971, pp. 1152–1155.

Primary Examiner—John K. Corbin
Assistant Examiner—Wm. H. Punter
Attorney, Agent, or Firm—Hill, Gross, Simpson, Van Santen, Steadman, Chiara & Simpson

[57] ABSTRACT

In an illustrated embodiment, brightness, color, opacity and fluorescent contribution to brightness of single thickness sheet material are measured by an optical measuring system providing for simultaneous measurement of transmitted and reflected light. One embodiment is designed so as to be capable of transverse scanning of a moving paper web on the paper machine. An optical window member of translucent diffusing material serves as a backing for the web for reflectance measurements and is in series with the web with respect to transmittance measurements. The optical window itself is selected as to its reflectance and transmittance so as to provide for periodic standardization of the instrument in an off-sheet position. Another embodiment will measure the same optical properties of single thickness sheet material selectively, with spectral response filters for characterizing such optical properties and with a series of narrow band filters. This latter embodiment also has the capability of measuring reflectance of an opaque pad of sheet material.

45 Claims, 23 Drawing Figures

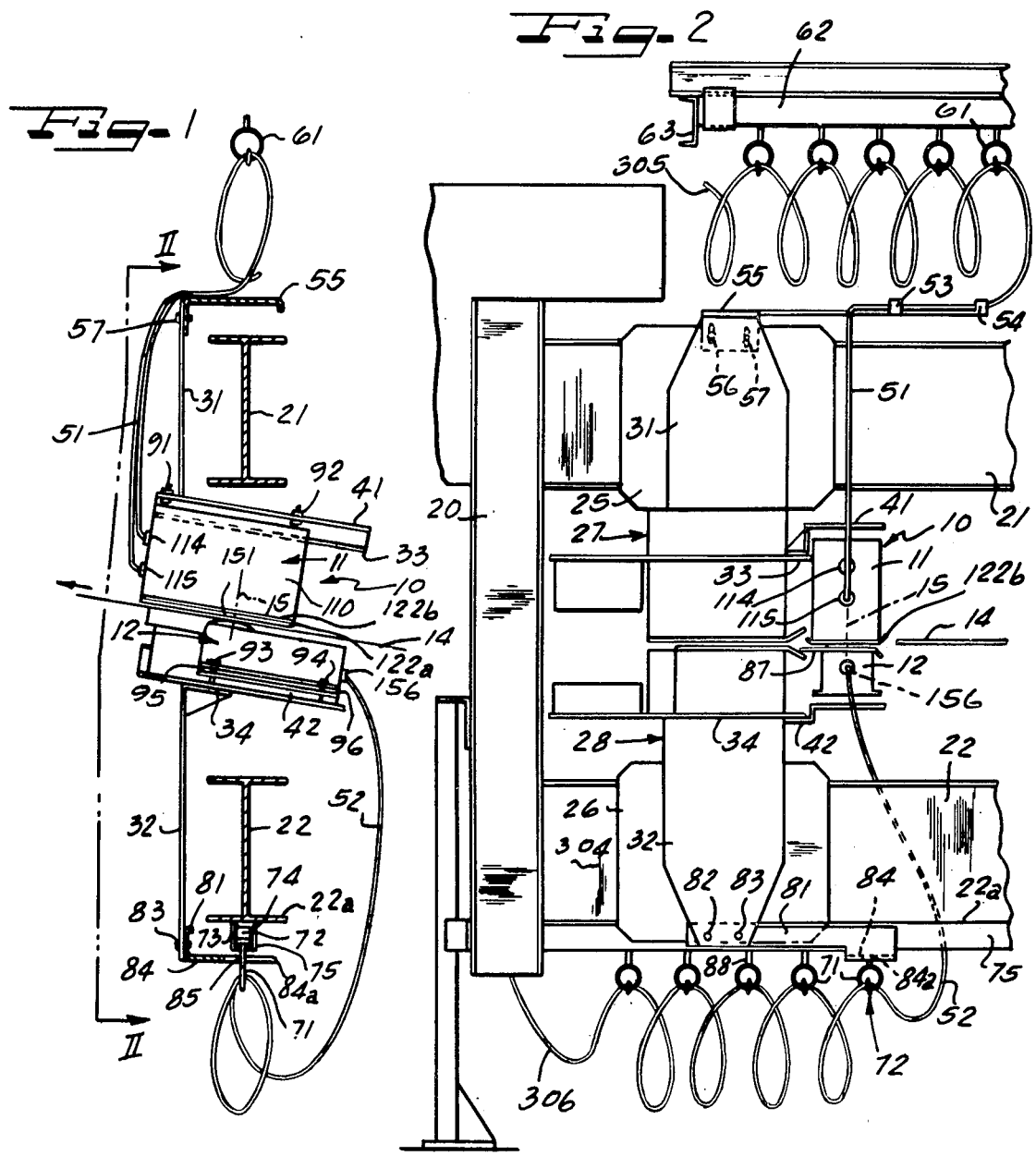

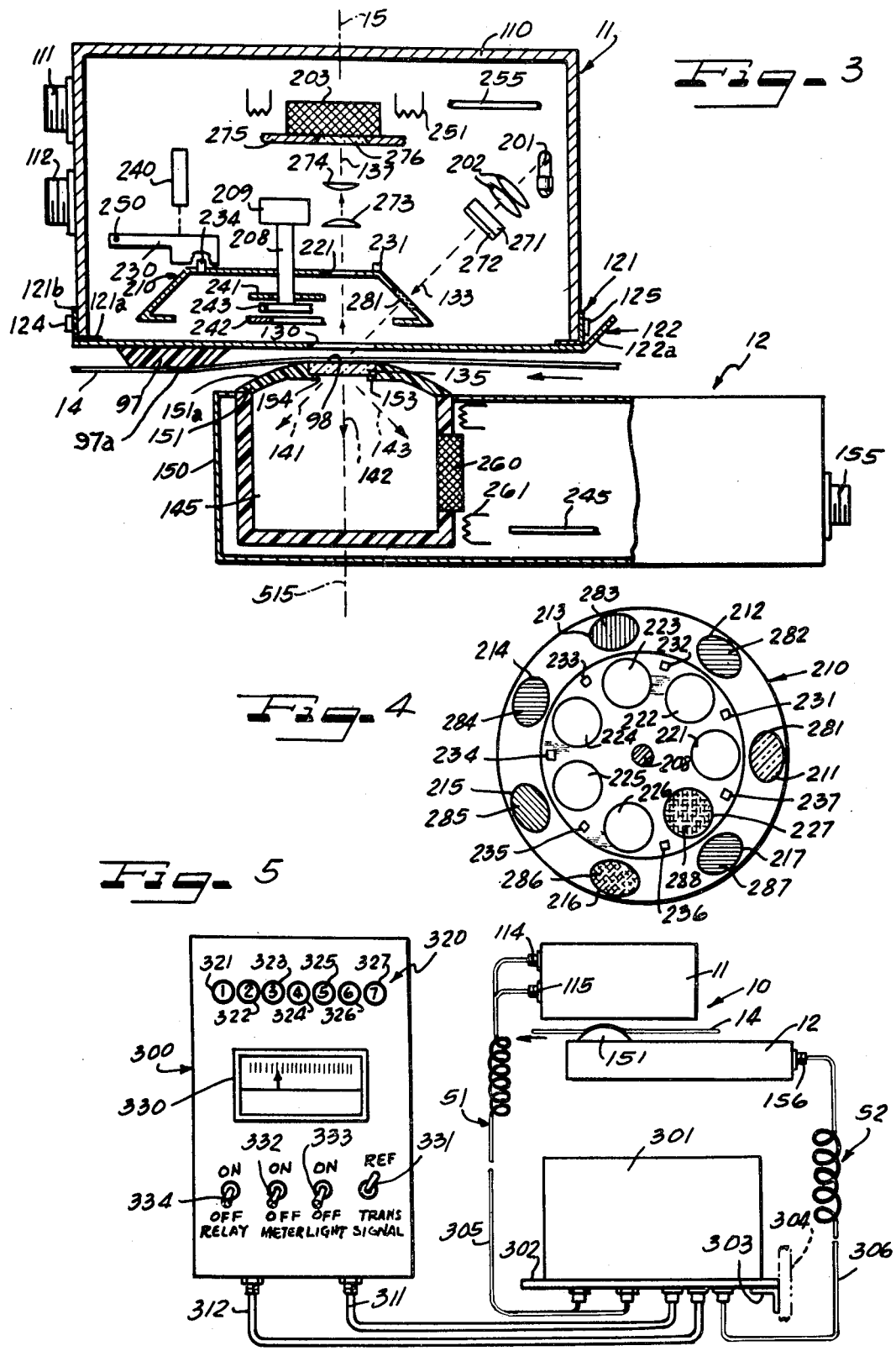

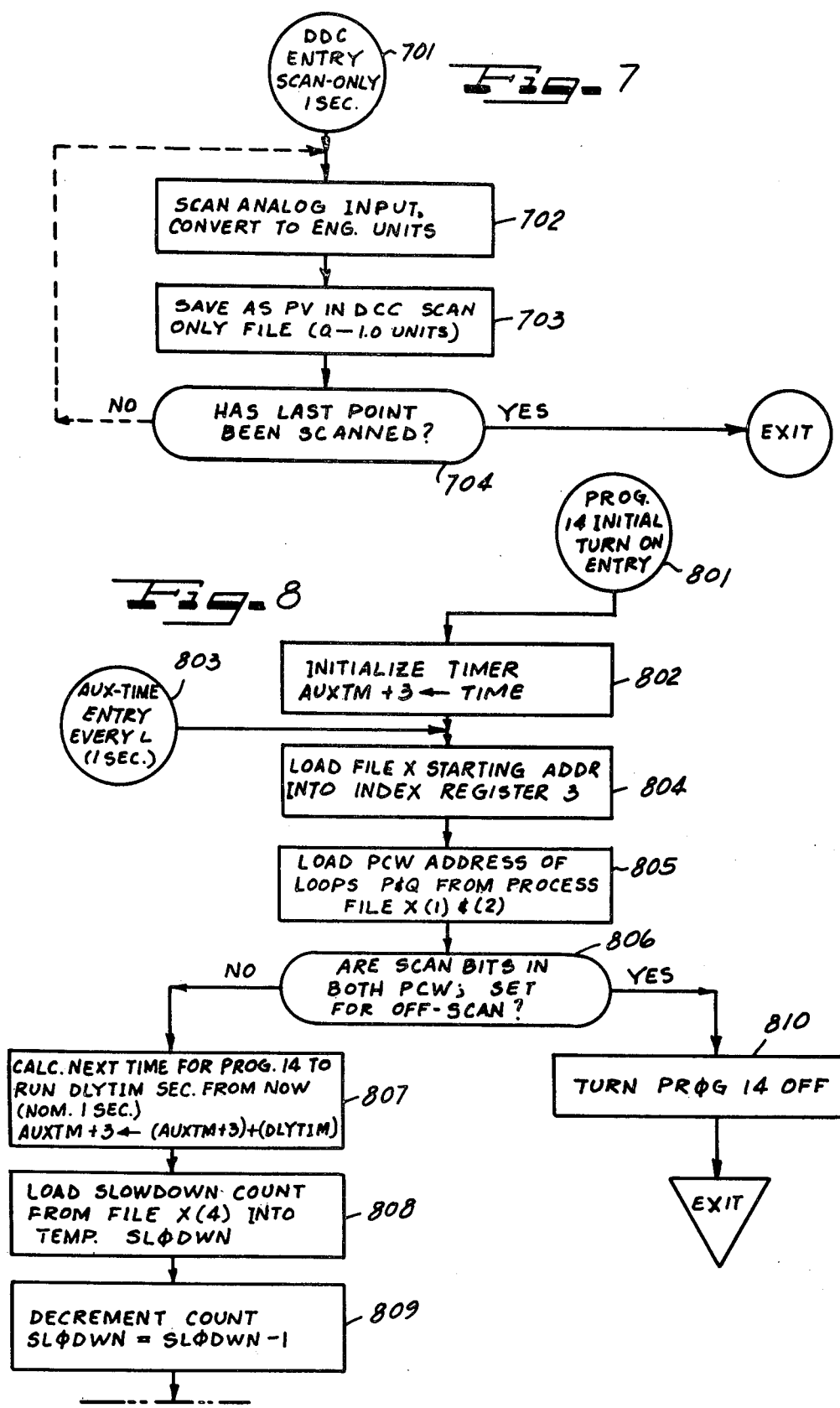

OPTICAL PROPERTY MEASUREMENT SYSTEM AND METHOD

CROSS-REFERENCE TO RELATED APPLICATION

The present application is a continuation in part of our pending application U.S. Ser. No. 438,993 filed Feb. 4, 1974 now U.S. Pat. No. 3,992,100 issued Nov. 16, 1976.

Certain of the subject matter hereof was first disclosed in a Lodzinski sole application U.S. Ser. No. 429,637 filed Dec. 28, 1973 (now abandoned) while other subject matter hereof was first disclosed in a Lodzinski sole application U.S. Ser. No. 540,251, filed Jan. 10, 1975 as a continuation in part of said application Ser. No. 429,637. Said application Ser. No. 540,251 is to issue as U.S. Pat. No. 4,019,819 on Apr. 26, 1977.

BACKGROUND OF THE INVENTION

In the prior art it is known to obtain an indication of color and brightness characteristics of a paper web during manufacture by an on-line measurement of reflectance value (Rg), but this measurement is decidedly different from that necessary for actual color and brightness characterizations. Accordingly, such a measurement must be accompanied by very frequent off-line testing, so as to enable an adequate empirical calibration of the measuring instrument. Further, a separate set of calibration parameters is required for each grade and weight of paper. Instruments which measure different optical parameters of single sheets sequentially, as by changing from a black backing to a white backing, are not adapted to obtaining two distinct measurements from the same region of a moving web. Laboratory instruments are generally delicate and bulky and not readily adaptable to on-line use.

SUMMARY OF THE INVENTION

This invention relates to an optical device and method for sensing optical properties of single thickness sheet material, and particularly to an on-the-paper-machine device and method for simultaneously sensing both transmitted and reflected light so as to obtain measurements from which the optical properties of interest can be calculated substantially independently of grade and weight of paper involved.

Accordingly it is an object of the present invention to provide an optical measuring system and method for sensing optical properties based on reflectance and transmittance measurements made at substantially a common region of a single thickness of partially translucent sheet material while such common region is backed by an optically stable material exhibiting uniform reflectance and transmittance values of substantial magnitude.

Another object of the invention is to provide such an optical measuring system and method capable of accurately sensing optical properties such as brightness, color, opacity and/or fluorescent contribution to brightness, and wherein the backing material serves as a standard for both the reflectance and transmittance measurements.

While such an optical measuring system is useful off-line for sensing optical properties of a single thickness sample, it is a further important object of the present invention to provide an embodiment of such an optical measuring system which is of sufficiently stable and durable construction so as to be adapted for on-line monitoring of the desired optical properties in the environment of the paper manufacturing process.

Another and further object of the invention is to provide an on-the-paper-machine optical monitoring device capable of automatic standardization by means of the same backing used during measurement of the reflectance and transmittance of the paper web.

A unique feature of the on-line optical monitoring device is its ability to simultaneously measure both reflected and transmitted light while a fixed backing stably supports the web and serves both as a standard for the reflectance measurement and as a conduit for the light energy which is to be collected as a measure of the transmittance of the web.

Other objects, features and advantages of the present invention will become apparent from the following detailed description taken in connection with the accompanying drawings.

ON THE DRAWINGS

FIG. 1 is a fragmentary somewhat diagrammatic longitudinal sectional view of a paper machine showing in outline a side view of an optical monitoring device in accordance with the present invention operatively mounted on line with the machine;

FIG. 2 is a fragmentary somewhat diagrammatic transverse sectional view of the paper machine of FIG. 1 and taken generally as indicated by the line II—II of FIG. 1 and looking in the direction of the arrows (toward the wet end of the paper machine), the view being taken so as to show in outline a direct front view of the optical monitoring device of FIG. 1;

FIG. 3 is a diagrammatic longitudinal sectional view of an on-the-paper-machine optical monitoring device in accordance with the present invention;

FIG. 4 is a partial diagrammatic plan view of the filter wheel assembly utilized in the monitoring device of FIG. 3;

FIG. 5 is a somewhat diagrammatic view illustrating an optical analyzer unit in electrical association with the optical monitoring device of FIGS. 1-4 and with a power supply unit;

FIG. 7 is a flow chart illustrating an existing direct digital control analog point scan program which has been adapted to allow for the collection and temporary storage of the reflectance and transmittance data acquired from the system of FIGS. 1-6;

Figure 20:
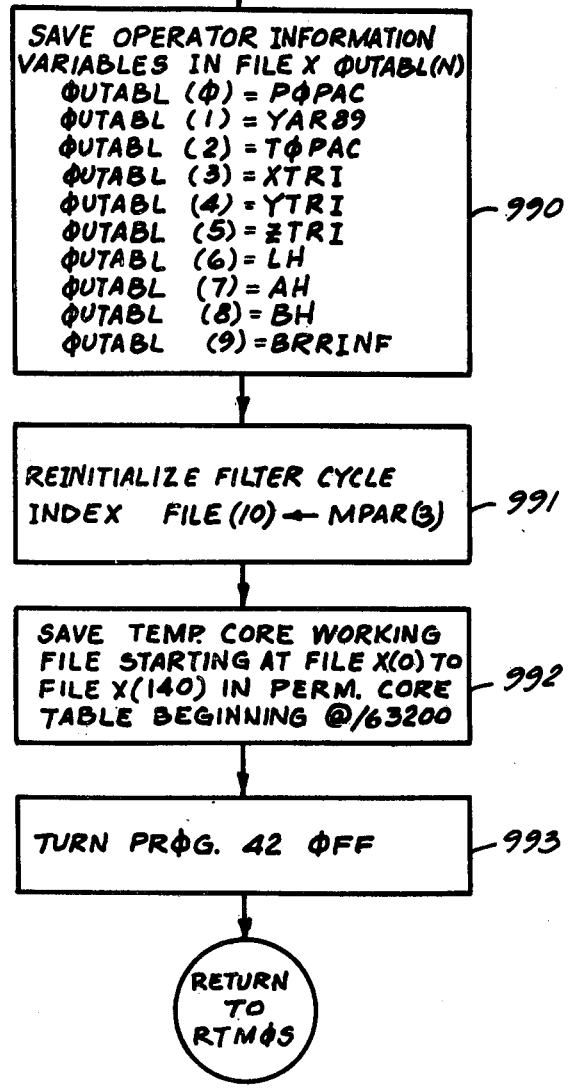
Figure 21:
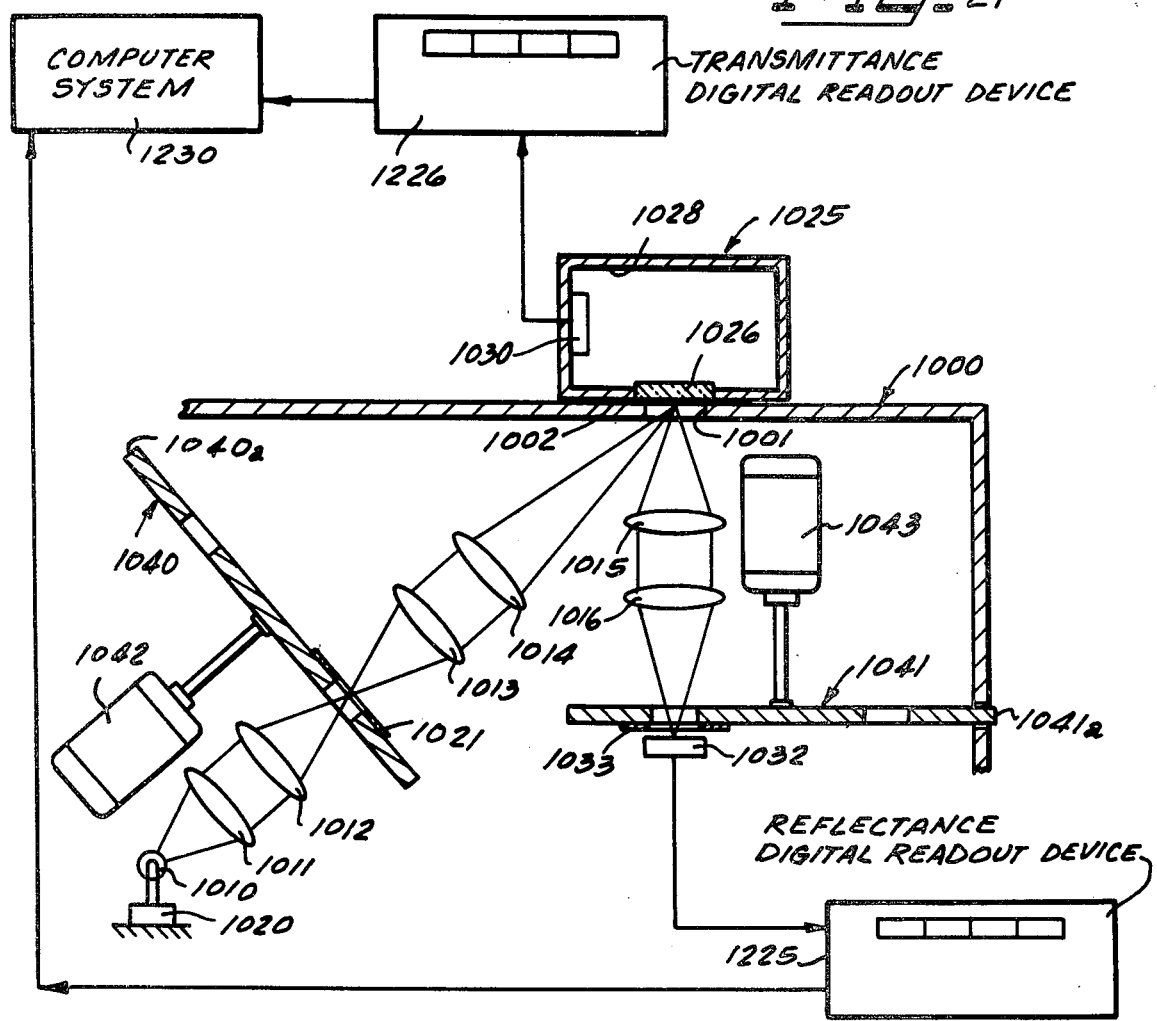
Figure 22:
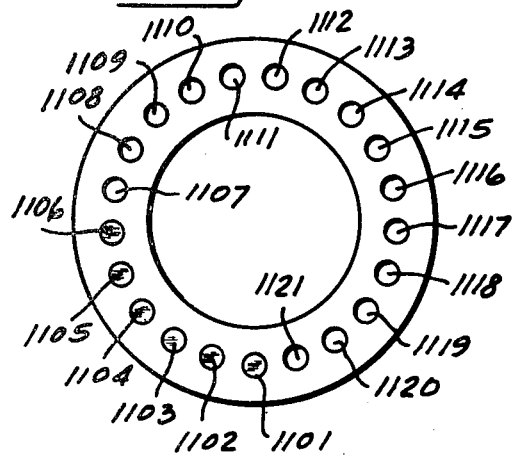
Figure 23:
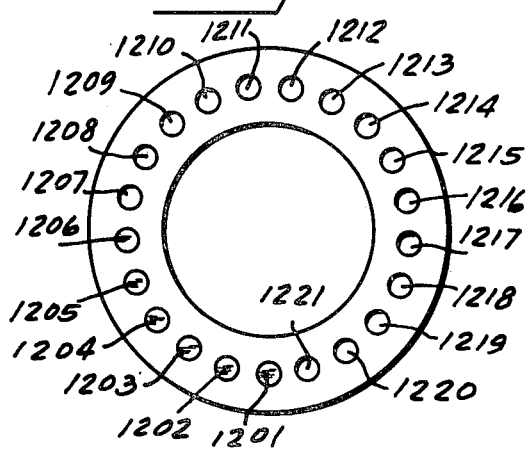

FIGS. 8-16 when arranged in a vertical series represent a program fourteen which is designed to read the reflectance and transmittance values stored pursuant to FIG. 7 and generally to control the operation of the system of FIGS. 1-6 and to apply correction factors to the raw reflectance and transmittance data;

FIGS. 17-20 when arranged in a vertical sequence represent a data reduction program forty-two whose purpose is to reduce the corrected reflectance and transmittance data as produced by the program of FIGS. 8-16 into terms with which papermakers are familiar and upon which paper optical specifications are based, e.g. brightness, opacity, color and fluorescence;

FIG. 21 is a diagrammatic vertical sectional view showing an off-the-machine instrument for simulating the optical measurements of the embodiment of FIGS. 1-20; and FIGS. 22 and 23 are diagrammatic plan views showing the incident beam filter wheel and the reflected beam filter wheel, respectively, for the instrument of FIG. 21.

DESCRIPTION OF THE PREFERRED EMBODIMENTS

Detailed Description Of The Apparatus Of FIGS. 1 and 2

FIGS. 1 and 2 will serve to illustrate the modifications of an existing paper machine which are required for carrying out a preferred embodiment of the present invention. Referring to FIGS. 1 and 2, an on-the-paper-machine optical monitoring device is diagrammatically indicated at 10 and comprises an upper sensing head 11 and a lower sensing head 12 which are maintained in precise relative alignment and disposed for operative association and transverse scanning movement relative to a paper web located as indicated at 14 in FIGS. 1 and 2. As will be described hereinafter with reference to FIGS. 3 and 4, in a particular design of the optical monitoring device, upper head 11 includes a light source for projecting light onto the web such that a portion of the light is reflected parallel to an optical axis indicated at 15, while a further portion of the light is transmitted through the paper web for collection and measurement by means of the lower sensing head 12.

For purposes of illustration, FIGS. 1 and 2 show portions of an existing web scanner construction which is utilized to scan the web 14 for conventional purposes. The conventional scanner construction includes fixed frame components such as 20, 21 and 22 forming what is known as an "O" type scanner frame. The conventional scanning structure further includes upper and lower slides 25 and 26 for joint horizontal movement along the horizontal beams 21 and 22. Associated with the slides 25 and 26 are movable assemblies 27 and 28 carried by the respective slides 25 and 26 and including vertically disposed plates 31 and 32 and angularly disposed flange members such as indicated at 33 and 34 in FIG. 1. These flange portions 33 and 34 have broad surfaces lying in planes generally parallel to the plane of the web 14 and are utilized for mounting of the monitoring device 10 of the present invention. In particular a top head mounting bracket is indicated at 41 in FIGS. 1 and 2 and is shown as being secured to the existing flange part 33 so as to mount the upper head 11 for scanning movement with the assembly 27. Similarly a lower head mounting bracket is indicated at 42 and is shown as being secured to flange part 34 of the lower movable assembly 28 so as to mount the lower sensing head 12 for scanning movement jointly with the upper sensing head 11.

For the purpose of electrical connection with the monitoring device 10 during its traverse of the web 14, electric cables are indicated at 51 and 52 for electrical connection with the components of the upper sensing head 11 and lower sensing head 12 of the monitoring device 10. The cable 51 is shown as being fastened by means of straps 53 and 54 to a top carrier slide bracket 55. The bracket is shown as being secured by means of fasteners 56 and 57 to the upper portion of vertical plate 31. As indicated in FIG. 2, successive loops of cable 51 are secured to swivel type ball bearing carriers such as indicated at 61. A trolley track 62 is supported from existing channels such as indicated at 63 and mounts the carriers 61 for horizontal movement as required to accommodate the scanning movement of the monitoring device 10 across the width of the web 14. Similarly, successive loops of the cable 52 are fastened to the eyes such as indicated at 71 of a lower series of carriers 72. As seen in FIG. 1 each of the carriers such as 72 includes a pair of rollers such as 73 and 74 riding in the trolley track 75 which is secured directly to the lower flange 22a of beam 22. A lower carrier slide bracket 81 is secured to vertical plate 32 by means of fasteners 82 and 83 and is provided with a horizontally extending flange 84 for engaging with the first of the series of lower carriers 72. In particular, carrier 72 is provided with a shank 85 which extends into a longitudinal slot 84a of flange 84. Thus, the first carrier 72 is interengaged with the bracket 81 and is caused to move with the lower assembly 28 and the lower sensing head 12. The remaining lower carriers such as that indicated at 83 move along the trolley track 75 as necessary to accommodate movement of the monitoring device 10 transversely of the web 14.

While FIGS. 1 and 2 have illustrated the optical monitoring device of the present invention as being mounted on line with the paper machine and have further illustrated the case where the monitoring device is to be scanned transversely of the web, it is considered that the optical monitoring device of the present invention would also be of great value if redesigned for bench mounting. By placing a single sheet of paper in a sample mount of the device, a technician could simultaneously test the sample for color, brightness, fluorescence, and opacity in a matter of seconds.

In the illustrated embodiment, however, it is contemplated that the monitoring device 10 will be mounted on line with the paper machine and will be capable of movement to a position clear of the edge of the web as indicated in FIG. 2 at the end of each hour of operation, for example. When the end of a production run for a given web 14 has been reached, or when a web break occurs for any other reason (such as accidental severance of the given web), the monitoring device 10 will be moved clear of the edge of the web path as indicated in FIG. 2. Each time the monitoring device 10 is moved to the off-web position shown in FIG. 2 it is preferred that readings be taken of the reflectance and transmittance values (without the web in the optical path) for the purpose of obtaining an updated calibration of the monitoring device. Thus, such updating of calibration may take place automatically (for example under the control of a process control computer controlling the paper manufacturing operation) at hourly intervals and also after web breaks. The monitoring device can, of course, be retracted manually any time desired by the operator for the purpose of checking calibration. By way of example, the monitoring device 10 may be capable of a normal scanning travel over a distance of 115 inches with provision for an additional travel of 16 inches to the position shown in FIG. 2. A flange is indicated at 87 which serves to insure proper re-engagement of the sensing head with the web at the operator's side of the illustrated paper machine (opposite the side indicated in FIG. 2).

The lower head 12 is designed to contact the web 14 during scanning thereof. The design spacing between the upper and lower heads 11 and 12 is 3/16 inch. The optical opening in the upper head 11 is aligned with the optical axis 15 and is to be maintained in alignment with the center of the window in the lower head 12. Four adusting screws such as those indicated at 91 and 92 are provided for accurate positioning of the upper head 11.

Similarly four position adjusting screws such as 93 and 94 serve for the accurate positioning of the lower head in conjunction with set screws such as indicated at 95 and 96. The adjusting screws are located at each corner of mounting brackets 41 and 42.

Modifications of FIGS. 1 and 2 To Insure Accurate Scanning

Where the web is not perfectly horizontal, but instead is curved across, its width, it is desirable to provide a web deflecting guide bar as indicated at 97 in FIG. 3 for insuring stable contact between the web 14 and the web engaging surface 98 of the lower sensing head 12. By way of example the guide bar may protrude from the lower surface of the upper sensing head a distance of 5/16 inch so as to overlap with respect to the vertical direction a distance of ⅛ inch relative to the lower sensing head web contacting surface 98. The guide bar 97 may have a width to force down at least about four inches of the width of the web at a section of web centered with respect to web engaging surface 98 of the lower sensing head relative to the machine direction. This insures a minimum of a ⅛ inch bellying of the sheet as it travels over the lower sensing head in all lateral positions of the sensing head.

In order to minimize changes in the 5/16 inch thickness dimension of the guide bar 97 due to wear, the guide bar is provided with a flat web engaging surface 97a which has a dimension in the direction of web movement of about one inch. By way of example, the guide bar may be made of Teflon.

Since the guide bar 97 is not necessary when the web is fed from the calender stack to the reel in a relatively planar configuration, it has not been shown in FIGS. 1 and 2.

Various modifications may of course be made to adapt the monitoring device of the present invention to various types of paper machinery, and to secure any desired degree of accuracy in the joint scanning movement of the upper and lower sensing heads relative to the paper.

Structure of the Optical Monitoring Device As Shown in FIGS. 3 and 4

Referring to FIG. 3, the upper sensing head 11 is shown as comprising a casing 110 having suitable connectors 111 and 112 for receiving suitable internally threaded fittings 114 and 115, FIG. 1, associated with the electric cable 51. The casing 110 receives a top head shoe 120 including an interior open rectangular frame 121 having a base flange 121a spot welded to shoe plate 122. The upstanding portion 121b engages the adjacent wall of casing 110 along all four sides thereof and is secured to the casing 110 by suitable fastening means such as indicated at 124 and 125 in FIG. 3. An edge 122a of shoe plate 122 is bent up at an angle of 45° at the side of the sensing head 11 facing the wet end of the paper machine, and a similar inclined edge 122b, FIG. 1, is provided at each of the sides of the sensing head so as to present smooth faces to the paper web during scanning movement of the sensing head. The shoe plate 122 is provided with a circular aperture of less than one inch diameter as indicated at 130 centered on the optical axis 15 of the device. In a present embodiment aperture 130 has a diameter of about ⅛ inch. This aperture 130 is preferably of minimum diameter necessary to accommodate the light paths of the instrument. In the illustrated embodiment the light path for the incident light beam as indicated at 133 is directed at an angle of approximately 45° and is focused to impinge on a window 135 at the optical axis 15. A reflected light path as indicated at 137 is normal to the web engaging surface 98 (which is the upper surface of window 135), and is coincident with the optical axis 15, while light transmitted through the web 14 and through the window 135 is directed as indicated by rays 141–143, for example, into an integrating cavity 145 of lower head 12.

The lower head 12 comprises a casing 150 having an annular dished plate 151 secured thereto and providing a generally segmental spherical web-contacting surface 151a surrounding window 135. The window 135 is preferably formed by a circular disk of translucent diffusing material. In the illustrated embodiment the window 135 is made of a polycrystalline ceramic material available under the trademark "Lucalux" from the General Electric Company. This material has physical properties similar to that of sapphire. The opposite faces of window 135 are flat and parallel and the thickness dimension is 1/16 inch. A lip is indicated at 153 for underlying an annular edge portion of window 135. This lip provides a circular aperture 154 having a diameter of about 15/16 inch so that the effective viewing area for the transmitted light is determined by the diameter of aperture 154. The casing 150 is shown as being provided with an electrical connector terminal 155 for receiving a suitable internally threaded fitting 156, FIG. 1, of cable 52.

As diagrammatically indicated in FIGS. 3 and 4, the upper sensing head 11 includes a light source 201, incident optical path means including lenses such as indicated at 202 and a photocell 203 for measuring reflected light returning along the reflected light path 137. A filter wheel 210 is shown diagrammatically as being mounted on a shaft 208 for rotation by means of a low torque motor indicated at 209. As best seen in FIG. 4, the filter wheel includes an outer series of apertures 211–217 for selective registry with the incident light beam path 133, and includes a series of inner apertures 221–227 for selective registry with the reflective light beam path 137. The various apertures may receive suitable filter elements as will hereinafter be explained in detail such that a series of measurements may be taken by successively indexing the filter wheel 210 to successive operating positions. In each operating position one aperture such as 211 is in alignment with the incident beam path 133 and a second aperture such as indicated at 221 is in alignment with the reflected light beam path 137.

By way of example, the motor 209 may be continuously energized during operation of the monitoring device, and the filter wheel may be retained in a selected angular position by engagement of a ratchet arm 230 with one of a series of cooperating lugs 231–237 arranged generally as indicated in FIG. 4 on the filter wheel 210. A solenoid is indicated at 240 as being mechanically coupled with ratchet arm 230 for momentarily lifting the ratchet arm 230 out of engagement with a cooperating lug such as 231 so as to permit the filter wheel to index one position. Immediately upon release of the energization of solenoid 240, the force of gravity returns to ratchet arm 230 to the position shown in FIG. 3 so as to be disposed in the path of the lugs and thus to engage the next lug in succession such as lug 232 as the motor 209 moves the filter wheel 210 into the next operating position.

As will hereafter be explained in greater detail, reed switches are mounted in circles on respective switching boards 241 and 242, FIG. 3, and the filter wheel shaft 208 carries a magnet 243 for actuating a respective pair of the reed switches in each operating position of the filter wheel 210. Thus the position of the filter wheel 210 determines which of the switches on the switching boards 241 and 242 are closed. As will be explained hereinafter, the reed switch on the upper switching board 241 which is closed determines the gain setting of an upper head amplifier at a level appropriate for the set of filters which are in the operating position. The reed switch on the lower switching board 242 which is closed activates a relay on a circuit board 245 in the lower head 12, and such relay in turn sets the lower head amplifier gain at the proper level. As will be explained in connection with the electric circuit diagram for the monitoring device, certain conductors of the cable 51 may be interconnected at a remote location so as to cause an indexing movement of the filter wheel 210. This external command serves to momentarily energize solenoid 240 and lift the ratchet arm 230 about is pivot point 250, allowing the motor 209 to rotate the filter wheel 210. The ratchet arm 230 returns to the position shown in FIG. 3 to catch the next lug on the filter wheel stalling the motor 209.

Four heaters such as indicated at 251 are mounted around photocell 204 so as to minimize the temperature variations of the photocell. A circuit board for mounting an amplifier for photocell 203 and for mounting the gain setting resistances associated with the reed switches is indicated at 255 in FIG. 3.

Referring to the lower head 12, FIG. 3 indicates a photocell 260 for receiving light from the intergrating cavity 145 and a series of heaters such as 261 mounted around the photocell 260 to minimize the temperature variations of the photocell. Circuit board 245 may mount a suitable amplifier for photocell 260, the gain of which being controlled by the relays previously mentioned.

The heaters 251 and 261 in the prototype unit were Pennsylvania Electronics Technology Type 12T55. (These are positive temperature coefficient thermistors with 55° C. switching temperatures.) These heaters will tend to stabilize the temperature since their ability to provide heat decreases as the ambient temperature increases. Above 55° C., they provide essentially no heat at all.

Discussion of Illustrative Operating Details for the Monitoring Device of FIGS. 3 and 4

A basic feature of the illustrated embodiment resides in its ability to measure simultaneously both reflected and transmitted light. While in the illustrated embodiment, the reflected light path 137 and the transmitted light path intersect the web 14 essentially at a common point, reflected light could be obtained from a point on the sample or web offset from the point where light is transmitted through the sample. For example, a backing of some specified reflectance such as a black body of zero or near zero reflectance could be located on the lower sensing head just ahead of or behind the transmitted light receptor compartment (with respect to the machine direction of the sample or the direction of movement of the web). In this case the upper sensing head could contain the light source as well as a reflected light receptor for receiving light reflected from the sample or moving web at a point directly above the backing of specified reflectance. Both the reflected light receptor in the upper sensing head and the transmitted light receptor in the lower sensing head could then supply signals simultaneously and continuously during measurement operations. Many other variations in the arrangement of the optics for measuring both reflected and transmitted light will occur to those skilled in the art.

Referring to the details of the illustrated embodiment, however, and to the case where it is desired to measure brightness, color, opacity and fluorescent contribution to brightness, light source 201, FIG. 3, may consist of a Model 1962 Quartzline lamp operated at 5.8 volts as measured at the lamp terminals. The 45° incident beam path 133 and the normal reflected beam path 137 correspond to those of a standard brightness tester, and a casting (not shown) from a bench type standard brightness tester was used in constructing a prototype of the illustrated embodiment to give rigid support for the optical components such as indicated at 202 and 271–276 in FIG. 3. In the specific prototype unit, a stock thickness polished Corning type 4–69 glass filter 271 and a second type 4–69 filter 272 ground and polished to an appropriate thickness were used in the incident beam path to absorb most of the infrared as well as to give proper spectral response.

The reflected light path 137 included a pair of lenses 273 and 274 which focus the light on a ⅜-inch aperture in the plate 275 of the casting. A piece of diffusing glass 276 is located on the ⅜-inch aperture so that the light distribution over the surface of photocell 203 will be reasonably uniform. A Weston model 856 RR Photronic cell was employed.

The filter wheel 210 is designed and located in such a way that either the incident or the reflected beam or both can be filtered as desired. In the prototype, the wheel 210 was driven by a small motor 209 operated at reduced voltage so that it could operate continuously in a stalled condition.

Commerically available color and brightness meters are usually manufactured with the spectral response filters located in the reflected beam. In the prototype device, and in the later on-machine version here illustrated as well, however, the filters which determine the spectral response of the first six filter positions are located in the incident beam. There are two basic reasons for this choice of design.

(1) Both the reflected and transmitted light have the same incident intensity and spectral response against which each can be compared. The alternate would necessitate two sets of identical filters, one set located in the reflected beam and another in the transmitted beam—a difficult design to achieve in practice.

(2) Filters in the incident beam can be used to absorb all ultraviolet light and prevent it from striking the specimen. Thus, fluorescence, a phenomenon not accounted for by Kubelka-Munk theory is avoided.

For reasons explained shortly, the seventh filter position is an exception to the above in that substantial ultraviolet light is intentionally permitted to exist within the incident beam. Outside of the phenomenon of fluorescence the spectral response is independent of whether such filters are located in the incident or the reflected beams.

The spectral response provided by the respective positions of the filter wheel 210 were as follows: (1) papermaker's brightness (TAPPI brightness), (2) blue portion of the $E_c\bar{x}$ function, (3) red portion of the $E_c\bar{x}$ function, (4) $E_c\bar{z}$ function without fluorescence (5) $E_c\bar{y}$ function, (6) $E_a\bar{y}$ function, and (7) $E_c\bar{z}$ function, with fluorescence.

As is understood in the art, the symbols $E_c\bar{x}$, $E_c\bar{y}$, $E_a\bar{y}$, and $E_c\bar{z}$ refer to tristimulus functions of wavelength as defined by the Commission Internationale c l'Éclairage which is identified by the abbreviation C.I.E. and is also known as the International Committee on Illumination. The subscript a in the function designation $E_a\bar{y}$ indicates that the function is based on a standardized illumination designated as C.I.E. Illuminant A, while the subscript c in the other function designations refers to a somewhat different standardized illumination which is designated as C.I.E. Illuminant C.

Filters for providing the above spectral response characteristics in the respective operating positions of the filter wheel 210 have been indicated in FIG. 4 by reference numeral 281-288. In the specific example under discussion apertures 221-226 are left open. Filter 281 is a standard filter for use in measuring TAPPI brightness, TAPPI referring to the Technical Association of the Pulp and Paper Industry. This filter transmits a narrow band of wavelengths in the vicinity of 457 nanometers.

Filters 282-285 are standard filters for a four-filter colorimeter and are conventionally designated X (blue), X (red), Z, and $Y_C$. These filters provide the wavelength distributions required for the measurement of the C.I.E. X, Y, and Z tristimulus values under Illuminant C.

Filter 286 is conventionally designated as a $Y_A$ filter and is required by the TAPPI standard method for opacity measurements. This is a broad band filter producing the C.I.E. Y wavelength distribution for Illuminant A, in conjunction with the source 201 previously described in this section. A discussion bearing on the feasibility of this type of measurement is found in a paper by L.R. Dearth, et al entitled "Study of Instruments for the Measurement of Opacity of Paper, V. Comparison of Printing Opacity Determined with Several Selected Instruments", Tappi, volume 53, No. 3 (March, 1970).

With respect to position No. 7 of the filter wheel 210, filters 287 and 288 are conventionally designated as Z (blue) and Z (yellow). As previously indicated, the purpose of the filters is to provide for a determination of the C.I.E. Z tristimulus value with the fluorescence component included. In filter position No. 4, filter 284 serves to remove the ultraviolet component from the incident beam so that a measure of the Z tristimulus value without fluorescence is obtained. In position No. 7 of the filter wheel, however, filter 287 in the incident beam is designed to transmit the ultraviolet component, so that the fluorescent component if any will be transmitted to photocell 203. The ultraviolet absorbing component of the Z type filter means is located in the reflected beam 137, whereas this component is in the incident beam for the No. 4 position. The fluorescent component is lineally related to the difference between the Z tristimulus values determined in the No. 4 and No. 7 positions of the filter wheel 210.

Filters 281-288 have been shown in FIG. 4 with different types of hatching which have been selected to represent generally the different light transmission properties of the filters. In particular, the hatching for filters 281-288 are those for representing white, blue, red, blue, green, orange, blue and yellow light transmission properties. The selection of hatching is primarily for purposes of graphical illustration and is not, of course, an exact representation of the light transmission properties of the respective filters.

Figure 6:
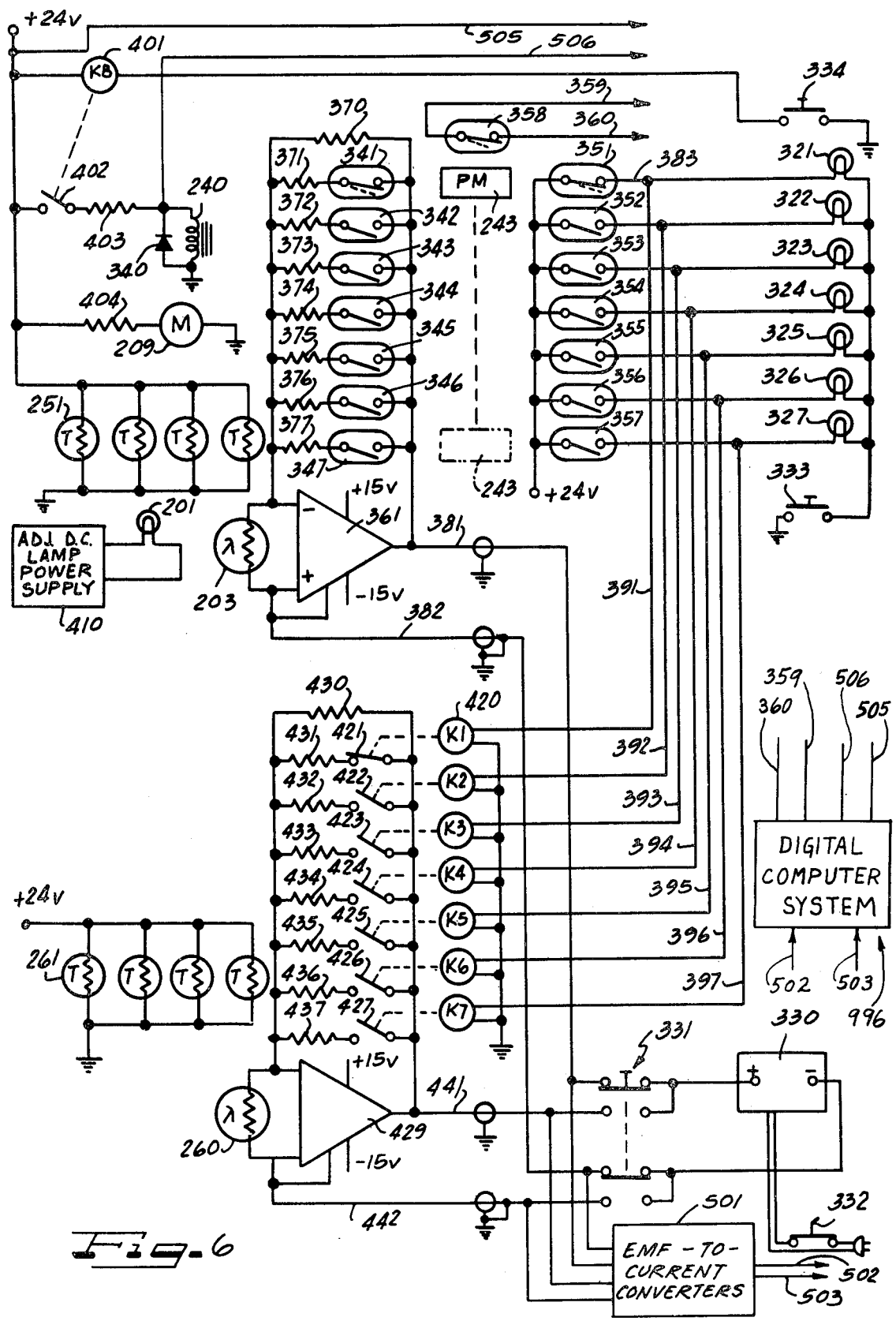
FIG. 6 is an electric circuit diagram illustrating the electrical connections between the various components of FIGS. 1-5.

Detailed Description of FIGS. 5 and 6

FIG. 5 illustrates diagrammatically the optical monitoring device 10 of FIGS. 1-4, and illustrates by way of example an optical analyzer unit 300 which may be electrically associated with the monitoring device and serve as an operator's console to be disposed at a convenient location adjacent the paper machine. By way of example, the optical analyzer unit may be mounted near the dry end of the paper machine, and may receive conventional alternating current power from the paper machine dry end panel. The optical analyzer unit 300 is illustrated as being coupled with the monitoring device 10 via a power supply unit 301 which is mounted adjacent the vertical column 20, FIG. 2, of the "O" frame along which the monitoring device is to travel in scanning the width of the web. For purposes of diagrammatic illustration, power supply unit 301 is shown as being provided with a mounting plate 302 which is secured by means of a bracket 303 to an end of horizontal beam 22 which has been specifically designated by reference numeral 304 in FIGS. 2 and 5. Referring to FIG. 2, it will be observed that the ends 305 and 306 of cables 51 and 52 are adjacent the end 304 of beam 22 so that this is a convenient location for mounting of the power supply 301. The electrical interconnections between the power supply unit 301 and the optical analyzer unit 300 are indicated as extending via a signal conduit 311 and a control conduit 312. By way of example, the signal conduit 311 may contain shielded electric cables for transmitting millivolt signals from the analogue amplifiers of the upper and lower sensing heads 11 and 12. The control conduit 312 may contain conductors which are respectively energized to represent the angular position of filter wheel 210, and may also contain a conductor for controlling the indexing movement of the filter wheel as will be explained in detail in connection with FIG. 6.

Referring to the optical analyzer unit 300 of FIG. 5, the front panel of the unit has been diagrammatically indicated at 320 as being provided with a series of lamps 321-327 for indicating the angular position of the filter wheel 210 within the upper sensing head 11. The lamps 321-327 have been numbered 1 through 7 in correspondence with the seven positions of the filter wheel, and the color of the lamps, for example, may be selected so as to signify the characteristics of the filters located in the openings of the filter wheel such as those indicated at 211-217.

In order to provide a visual indication of the amplitude of the millivolt signals supplied from the sensing heads 11 and 12, a suitable meter is indicated at 330 and a selector switch is indicated at 331 for selectively supplying to the meter the analogue signal from the upper sensing head 11 or from the lower sensing head 12. A switch 332 is indicated for controlling the supply of conventional alternating current power to the meter, and a second switch 333 is indicated for controlling the supply of energizing power for the lamps 321-327. Another switch 334 may be momentarily actuated so as to index the filter wheel 210 to a desired station. The switches 331-334 may, of course, take any desired form, and have merely been indicated diagrammatically in FIG. 5.

Referring to FIG. 6, various of the components previously referred to have been indicated by electrical symbols, and for convenience of correlation of FIG. 6 with FIGS. 1 through 5, the same reference characters have been utilized. In particular, FIG. 6 shows symbolically a light source 201, associated photocells, 203 and 260, filter wheel drive motor 209, control solenoid 240, and permanent magnet 243 which rotates with the filter wheel 210 so as to represent the angular position of the filter wheel. Also shown in FIG. 6, are the four heaters 251 associated with photocell 203, and the four heaters 261 associated with the photocell 260. Further, lamps 321-327, millivoltmeter 330 and switches 331-334 of the optical analyzer unit 300 have been symbolically indicated in FIG. 6.

Referring first to the components associated with the upper sensing head 11, there is illustrated in the upper left part of FIG. 6 a diode 340 connected across solenoid 240. For diagrammatic purposes, permanent magnet 243 is shown arranged between two series of reed switches 341-347 and 351-357. A further reed switch 358 is indicated for actuation in the number 1 position of the filter wheel 210 along with switches 341 and 351. The conductors 359 and 360 associated with switch 358 may be connected with the optical analyzer unit 300, and may be connected via the optical analyzer unit 300 with a remote computer, where the illustrated apparatus forms part of a computer control system for controlling the associated paper machinery.

The reed switches 341-347 are shown as being associated with an operational amplifier 361, so that switches 341-347 serve to select the desired value of feed back resistance for the amplifier in each position of the filter wheel 210. Thus, switches 341-347 served to selectively connect in parallel with resistance 370, additional resistance values 371-377, respectively, for adjusting the total resistance between the input and output terminals of the amplifier 361. Thus, in the number 1 position of the filter wheel, permanent magnet 243 is in a position to actuate switch 341, and connect resistance value 371 in parallel with resistor 370. As will hereinafter be explained, resistance means 371-377 may include variable resistors for adjustment so as to provide the desired gain of amplifier 361 in the respective filter positions, or fixed resistance values may be inserted as indicated, once the desired values have been determined for a given filter wheel. As indicated in FIG. 6, the output of amplifier 361 may be transmitted by means of shielded cables 381 and 382. These cables form part of the overall cable indicated at 51 in FIG. 5 leading from the upper sensing head 11 to the power supply unit 301.

Also forming part of the cable 51 would be the conductors such as indicated at 383 from the respective reed switches 351-357. These conductors such as 383 would connect with respective conductors 391-397 of cable 52 leading from the power supply 301 to the lower sensing head 12.

Included as part of the power supply unit 301 would be components such as relay actuating coil 401, associated normally open contact 402, and resistors 403 and 404 shown at the upper left in FIG. 6. Further, the power supply would include an adjustable direct current lamp power supply component 410 for supplying a precisely adjusted or controlled electrical energization for light source 201. Further, of course, the power supply would supply the required direct current operating potentials for the upper sensing head as indicated in FIG. 6.

The lower left section of FIG. 6 illustrates the electrical components of the lower sensing head 12. In the lower sensing head, conductors 391-397 control energization of the operating coils of respective relays K1 through K7. With the permanent magnet 243 in the number 1 position, reed switch 351 is closed, and operating coil 420 of relay K1 is energized closing the associated relay contact 421. The remaining relays K2 through K7 are deenergized, so that the respective associated contacts 422-427 remain open. The contacts 421-427 serve to control the resistance in the feed back path of operational amplifier 429 in conjunction with resistor 430 and resistance means 431-437. As explained in reference to the upper sensing head, resistance means 431-437 may include adjustable resistors, or fixed resistors as shown selected to provide the desired gain of amplifier 429 for the respective positions of the filter wheel 210. The shielded cables 441 and 442 from the output of amplifier 429 connect with power supply unit 301 as part of cable 52. The outputs from the amplifiers 361 and 429 are conducted from the power supply unit 301 to the optical analyzer unit 300 via signal conduit 311, and within the optical analyzer unit connect with respective terminals of the selector switch 331 as indicated at the lower part of FIG. 6. Thus, in the upper position of the selector 331, the output of amplifier 361 is connected with the meter 330, while in the lower position of selector 331, the output of amplifier 429 is supplied to the meter 330. Of course, the optical analyzer 300 may further include analogue to digital converters for converting the outputs of the amplifiers 361 and 429 to digital form for transmission to a remote computer, for example. It will be apparent to those skilled in the art that the remote computer could be programmed to control the sequential actuation of relay 401 during each increment of scanning movement of the monitoring device 10 so as to obtain readings from each desired sampling region of the web 14 for each of the seven positions of the filter wheel 210. The remote computer would then be in a position to correspondingly determine the average optical characteristics of a given length section of the paper web 14, for example, and control suitable inputs to the paper machine so as to maintain desired optical characteristics of the paper being manufactured. Alternatively, of course, the arrangement of FIGS. 1-6 can be utilized simply to take readings from the meter 330 for each filter wheel position during scanning of the web, so as to obtain readings reflecting the optical characteristics of the length sections of the web so scanned. Still further, of course, the circuitry of FIGS. 5 and 6 can be utilized either with the monitoring device located in a fixed position relative to the width of the web (by means of a C-type frame), or with the device off-line from the paper machine, so as to obtain desired readings from the meter 330 for each position of the filter wheel 210 during optical excitation of a single sheet sample of the web held in a sample holder so as to be disposed essentially as indicated for the web 14 in FIG. 3.

Exemplary Commercially Available Components

Commercially available components which are included in the present design of FIGS. 1-6 are as follows.

Main power supply. Lambda Electronics Corporation Model LQS-DA-5124 providing a direct current (DC) output voltage of 24 volts and a maximum current at 40° C. of 5 amperes.

Reed switches. For reflectance amplifier gain settings-Model MMRR-2, and for transmittance amplifier gain settings-Model MINI-2, manufactured by Hamlin, Inc. The relays in the lower sensing head of Type 821A of Grigsby-Barton, Inc.

Operational amplifiers, Model 233J chopper stabilized amplifiers of Analog Devices, Inc. Model 904 power supply supplying plus or minus 15 volts with a minimum full load output current of plus or minus 50 milliamperes.

Digital panel meter (used for off-line studies and for on-line operation before being interfaced with the computer). Weston Model 1290.

Filter wheel advance solenoid. Type T 12×13-C-24 volt DC flat plug plunger of Guardian Electric Manufacturing Company, Antibottoming washer made of polyurethane rubber. Operation of the solenoid until interfaced with the computer has been with the use of a time adjusted relay, namely a Model CG 102A6 transistorized repeat cycle timer of G. & W. Eagle Signal Co.

Filter wheel drive motor. Type 1AD3001 Siemens brushless DC motor. The drive belt and pulleys for coupling the motor 209 with the the shaft 208 are specified as positive drive belt FS-80 and positive drive pulleys FC5-20 and FC5-40 of PIC Design Corporation, a Benrus subsidiary. The belt has a stainless steel core and the pulleys have a ¼ inch diameter bore.

Computer Interfacing

In preparing the monitoring device for on-line operation on the paper machine, the zero to 140 millivolt DC signals from the sensing heads will be supplied to respective emf-to-current converters of component 501, FIG. 6. As an example, Rochester Instrument Systems Model SC-1304 emf-to-current converters may be used. Such a converter will provide an output of 10 to 50 milliamperes DC suitable for driving an analog to digital converter at the computer. The emf-to-current converters will provide an isolated input and output so that grounding will not be a problem.

The converters of component 501, will be housed with optical analyzer 300, FIG. 5, and will connect with respective points thirty one of Groups five hundred and six hundred (not shown) at the control computer analog signal input via conductors such as indicated at 502 and 503 in FIG. 6.

Conductors 505 and 506, FIG. 6, associated with filter wheel indexing solenoid 240, FIGS. 3 and 6, may extend within control conduit 312, FIG. 5, and connect with the control computer output terminals at a location designated Group forty two hundred and six, point nineteen (not shown). (Switch 334 should remain open (off) during computer operation of FIGS. 1–6).

Conductors 359 and 360, FIG. 6, may connect with an input of the control computer at a location designated Group fourteen hundred, point twenty-three (not shown).

Discussion of an Earlier Prototype System

Structure and Operation of a Prototype Optical Monitoring Device

A prototype optical monitoring device was first constructed so as to test the feasibility of the concepts of the present invention. As a result of the experimental work with the prototype system, a preferred system has been designed and will hereinafter be described in greater detail. Since the operation of the prototype system is somewhat different from that of the later designed system, a description of the prototype system will serve to illustrate alternative features and an alternative method of operation in accordance with the present invention.

In the original setting up of the prototype system, the upper and lower sensing heads should be brought into proper alignment and spacing. The spacing should be just under ¼-inch between the case 110 and the surface of the diffusing glass of window 135. (In the prototype unit, there were no additional parts between the case 110 and window 135 such as the shoe plate 122 shown in FIG. 3.) The lower sensing head should be moved laterally in all directions to locate the point where the maximum reading occurs from photocell 260 as well as the point of least sensitivity to relative movement of the upper and lower sensing heads. In an initial calibration of the prototype monitoring device, potentiometers are included as part of the resistance means 371–377 and 431–437 and are adjusted for the respective positions of the filter wheel 210 to give the correct readings for the reflectance and transmittance of the diffusing glass 135 (in the absence any paper sample between the upper and lower sensing heads). The values which were used in this initial calibration are indicative of percentage absolute reflectance and transmittance on a scale of 100, and are as follows:

Table 1

| Table Showing Exemplary Calibration for the Prototype System- Diffusing Glass Reflectance and Transmittance Values With No Paper Specimen Present | | |
|---|---|---|
| Filter Wheel Position No. | Reflectance Value, RSD (Millivolts) | Transmittance Value, TSD (Millivolts) |
| 1 | 35.4 | 54.0 |
| 2 | 35.0 | 56.1 |
| 3 | 34.4 | 56.9 |
| 4 | 34.6 | 56.6 |
| 5 | 34.7 | 56.4 |
| 6 | 34.5 | 56.6 |
| 7 | 34.8 | 0.6* |

*The transmittance valve of the No. 7 filter position is not needed, and consequently a low amplification of this signal was arbitrarily selected.

The readings in millivolts can be converted to other desired units by comparing the readings in millivolts for a given paper specimen with the readings obtained with a standard laboratory instrument, measuring the reflectance of the specimen with the laboratory instrument while backing the paper sheet with a piece of Lucalux and a black body. By measuring the reflectance of the single sheet backed with a black body (no fluorescence), the value of transmittance for the specimen can be calculated and this calculated value utilized for calibrating the lower sensing head. If the fluorescent component is included in the laboratory instrument, and if fluorescence is involved, the fluorescence component can be determined by means of a standard reflection meter, and the fluorescent component can then be subtracted from the measured data before making the calculation of transmittance.

The laboratory testing of the prototype system confirmed that a monitoring device such as illustrated in FIGS. 1–4 should have a potential accuracy equal to that of comparable off-line testers provided certain web scanning requirements are met.

Laboratory tests were run on color standard samples of the grades and colors usually run on the paper machine shown in FIGS. 1 and 2. In addition, a variety of opaques, and a variety of colored 50 pound and 70 pound offsets were included in the tests. A four centimeter diameter circle was scribed on each sample to insure that all tests would be done within the same 12 square centimeter section of the sample. Values of $R_o$, $R_{oo}$, and TAPPI opacity measurements were made on the available standard laboratory instruments. All test were made on the felt side of the sample with the grain in the standard direction. For $R_{oo}$ measurements, the samples were backed by piles of tabs cut from the edge of the same sheet of paper. In addition to the TAPPI opacity measured on the stadard opacimeter, TAPPI opacity was calculated via Kubelka-Munk theory from data obtained with a standard automatic color-brightness tester.

The same paper samples were clamped into a holder which held the sample under tension with the lower head of the monitoring device bellying ⅛-inch to ¼-inch into the sheet. The grain of the sheet was oriented parallel to the longitudinal axis of the upper sensing head (that is the machine direction of the sheet was in the same orientation as would occur on the paper machine as indicated in FIGS. 1 and 2). The felt side was always up. Care was taken to make sure that the tested area was within the twelve square centimeter circle scribed on the sample.

The transmittance and reflectance readings were taken from a digital volt meter attached to the output terminals of amplifiers 361 and 429. Calibration data was taken off the Lucalux with no sheet present. Test values were taken on all filters with the sheet in place. The transmittance and reflectance values were keyed into a standard calculator with the calibration data. The calculator was programmed to calculate the color (in C.I.E. X, Y, Z, for example), fluorescent component, brightness, TAPPI opacity and printing opacity (based on $Y_c$). By supplying the basis weight, the computer could also be requested to calculate s, the scattering coefficient (an index of the effect of pigment efficiency and fiber surface area), and k, the absorption coefficient (an index of the effectiveness of dyes in the sheet). The coefficient s and k are essentially independent of basis weight. Kubelka-Munk theory is the basis of the calculations used.

All of the samples were tested without changing the relative position of the two sensing heads. One set of data was obtained with the heads in a variety of positions to determine the effect of geometric variations.

Since fluorescence is not compatible with Kubelka-Munk theory, the prototype system was carefully designed so that all data used for Kubelka-Munk analyses have excluded fluorescence. The prototype system measures fluorescence separately. A fluorescent contribution is determined from the prototype data by subtracting the Z distribution reflectance without fluorescence (filter wheel position No. 4) from the Z distribution reflectance with fluorescence (filter wheel position No. 7), and multiplying by the appropriate factor.

An independent check on fluorescence measurements, a modified brightness tester was utilized which had a filter wheel allowing for standard brightness and Z distribution filters to be put in the reflected beam. In addition, the filter wheel contained brightness and Z distribution filters which had been modified by removing the ultraviolet absorbing component of these filters. A special mount allows the operator to put the appropriate ultraviolet absorbing filter in the incident beam. Thus, measurements of brightness and C.I.E. Z tristimulus, with and without fluorescence, could be made.

Fluorescent contributions were calculated by difference. Some measurements were made on single sheets with a standard backing. Most of the samples were measured with an infinite pack of tabs. The incident beam filter of the prototype's No. 7 position was such that it permitted about twice the standard quantity of ultraviolet light to strike the specimen. Consequently, measurements of the fluorescent contribution measured on the modified brightness tester and the prototype system correlated well (correlation coefficient of 0.992) but the modified brightness tester value is only 0.528 as large as that measured by the prototype system. Calculations of prototype data now involve calculation of the fluorescent component by multiplying the difference of filter positions No. 7 and No. 4 by 0.528.

Because only one fluorescent dye (Tinopal) in all of the paper specimens was used, the fluorescent contribution needed to be measured only once. The prototype data provides a basis for measuring the fluorescent component Z. Measurements by an independent laboratory showed that the paper specimens do not fluoresce significantly in the X (red) or Y distributions; therefore, fluorescent contributions need only be determined for the blue colored distributions. A linear regression was run on the independent laboratory data which demonstrated that the fluorescent component for X (blue) can be predicted by multiplying the fluorescent component for Z by 1.204. A regression run on fluorescent data from the modified brightness tester shows that the fluorescent contribution for brightness can be calculated by multiplying the fluorescent contribution for Z by 0.864. In summary, fluorescent contributions are calculated by the following formulas:

$F_Z = 0.528$ (Z reflectance with fluorescence minus Z reflectance without fluorescence.)

$F_{X(blue)} = 1.204 \, F_Z$ $F_{Brightness} = 0.864 \, F_Z$

These fluorescent contributions are added to the respective calculated $R_{oo}$ values when calculating optical properties from prototype data. The test results for fluorescent and non-fluorescent papers agree with values measured on the standard automatic color-brightness tester.

Discussion of the Results of Mechanical Life Testing of the Prototype System and Design Features Selected for the Preferred System In Light of Such Life Testing The following details concerning the results of life testing of the prototype system are considered to reflect minor problems of construction and operation which considered individually are readily corrected for by those skilled in the art. In order to minimize the burden of the total number of such minor problems, and thus to expedite practice of the prototype system, solutions to the various problems which were encountered are briefly referred to.

The filter wheel is advanced by a low torque stallable motor. A timing belt links sprockets on the motor and the filter wheel shaft. The original timing belt had a dacron core. The core of the original belt broke in two places resulting in stretching and eventual loss of teeth. Uneven rate of rotation of the filter wheel occurred due to binding of the belt. Eventually, the plastic drive sprocket broke. Both sprockets were replaced with stainless steel sprockets and the timing belt was replaced with a belt containing a steel core. Installation of the steel sprockets and steel core belt revealed that excessive belt tension could stall the motor. The motor mount holes were slotted allowing the motor to pivot slightly around one mounting screw. Belt tension was adjusted by pivoting the motor. It is concluded that future models should include an idler wheel or some other means of adjusting the tension of the timing belt.

Some problems were experienced with respect to indexing of the filter wheel with the ratchet arm sticking on the tooth so that the ratchet arm does not clear the tooth when a command is given to index the filter wheel. The remedy has been to reduce the roughness of the mating surfaces by filing on the tooth, or smoothing the tooth with a stone. In future models, the shapes and/or smoothness of the ratchet arm and the teeth should be altered to minimize sticking. One solution would be to provide the ratchet arm and the teeth with highly polished mating surfaces.

The ratchet arm is lifted by a 24 volt direct current solenoid. After some time, the plunger of the solenoid became magnetized and would stick to the inside of the coil. This "hanging up" would prevent the ratchet arm from catching the next tooth. A resistor was installed in series with the solenoid coil to reduce the strength of the magnetic field. The plunger of the solenoid was coated with a special material. The coated plunger worked well for about three months before it, too, magnetized enough to hang up. The solution adopted was to provide the solenoid with a flat topped plunger which is stopped at the end of its stroke by a bumper of rubber-like material.

The response of a photocell is somewhat temperature sensitive. For this reasons, it is necessary to keep the photocells at a constant temperature. Ambient temperatures on the O-frame of the No. 6 paper machine indicated at FIGS. 1 and 2 have been measured as high as 118° F. (48° C.) in the summer. The photocells in both heads are mounted in massive metal blocks. Each metal block has four thermistor heaters mounted in close proximity to the photocell. These thermistors have switching temperatures of 55° C., (that is about 130° F.). The intention of this design was to add enough heat to the instrument to hold the temperature steady at about 55° C. During bench studies, this temperature was never reached due to the low capacity of the heaters. At machine room temperatures, however, the instrument temperature may reach 55° C.

During the bench studies, it was found that the heaters did minimize temperature variations. The few degrees of temperature variation that were observed during normal operation usually occurred slowly. Changes in instrument temperature affected the output signal less than anticipated. Based on this experience in the laboratory, the maximum variation in head temperature should be less than 3° F. per hour. Temperature variations of this magnitude will not have a significant effect on the output signal. Long term temperature changes would be corrected for by the calibrations each time the head goes off web.

In the laboratory, there was a minimum of dirt problems. On the machine, however, the hole could allow dirt to enter the upper head. Up to a point, dirt on the lenses and filters will be corrected for by the periodic calibration routine. Excessive dirt, however, will reduce the sensitivity of the instrument and may even affect its accuracy. Periodic cleaning of the lexses and filters will be required. If dirt accumulates too rapidly, it may be necessary to attach an air purge to the upper head.

The lower head of the prototype system is completely sealed so that no dirt problem is anticipated inside the lower head. Because the Lucolux window is in contact with the sheet, friction will keep it clean.

Most of the filters consisted of two or three component parts. There have been some problems with dirt getting between the components of the filters.

The case on the lower head as well as the case on the upper head should allow most general maintenance and trouble-shooting to be done without dismounting the head. A completely removable case would be desirable. At a minimum access should be provided for the following: (1) convenient light bulb change, (available on the prototype), (2) cleaning of lenses, (available on the prototype), (3) cleaning of the filters. (Access is presently available to one side of each filter. The side which is most likely to collect dirt is not accessible in the prototype.) (4) The amplifier. The amplifier is a standard plug-in module. In the event of a breakdown it could be replaced in seconds if it is accessible. Furthermore, it is necessary to remove the amplifier to do any trouble-shooting on the gain circuitry. (5) The circuit board holding all of the gain control resistors. The choice of gain circuitry is controlled by reed switches which are not accessible on the prototype without a partial disassembly of the instrument. Malfunctions of the reed switches, however, can easily be diagnosed by removing the amplifier and taking resistance measurements on the gain control circuits. There is also the possibility of mechanical or electrical damage to a resistor or a potentiometer mounted on this circuit board. With proper access a damaged part could be replaced in five to twenty minutes. (6) The photocell. With proper access, the photocell could be replaced quickly and easily. (7) The heater. The heater are adjacent to the photocell and are generally just as easily serviced. (8) Indexing mechanism. The present accessibility to the ratchet teeth, rachet arm and solenoid is adequate but not very convenient on the prototype. A certain amount of access to these parts is needed to correct chronic indexing problems such as sticking and "hanging up".

The filters are presently mounted in the filter wheel of the prototype by spring clips. Most of the filters are compound filters containing as many as four component pieces of glass. During laboratory trials, increases in the optical density of a filter were frequently observed which could not be corrected by cleaning the surfaces of the filter. Upon removing one of the filters, it was discovered that foreign material was collecting between the components of the compound filter. The use of lens cleaning solution on the filters may have accelerated the problem if capillary action drew foreign material between the components. A set of gaskets and some type of threaded mount should be used to mount the filters in such a way as to minimize foreign material (including cleaning solutions) from getting between the components of compound filters.

In mounting the prototype sensing heads on an O-frame, it is necessary to bring the geometric alignment of the heads as close to their optimum relationship as possible. The original intention was to set the gap between the heads with the aid of a spacer; however, flexibility of the sheet metal case of the prototype upper sensing head prevented the use of a spacer for setting the gap. Accordingly, the shoe plate 122 of the new upper sensing head shown in FIG. 3 has been made of a thickness and consequent rigidity so as to enable the use of a spacer gauge to set the gap between the upper and lower heads. (The gap is reduced by 1/16 inch to 3/16 inch because of the thickness of shoe plate 122.)

The gap between the heads is a most critical dimension as far as calibration and reproducability is concerned. In the prototype it was intended to calibrate relative to an average gap, thus correcting the readings for variations in the gap from the average gap.

One of the criteria used in designing the prototype was minimum head length in the machine direction. Unfortunately, the upper head was turned 90° in order to give the prototype unit the same geometry as the General Electric Brightness Meter, Automatic Color-Brightness Tester, and Hunterlab Color Meter. In this new position, the prototype head is 12¼ inches long in the machine direction plus 2½ inches for cable connectors. Redesign should be possible to reduce the machine direction dimension to about 8 inches and to relocate the position of the cable connections.

The lining of the case for the upper head should be matte as well as black to prevent reflection of ambient light within the case and a possible spurious effect on the photocell reading.

Conclusions from Mechanical Testing of the Prototype System

Following the correction of miscellaneous start up problems the prototype system was found to function well mechanically. As a test of its durability, the prototype system was placed in continuous operation for a period of over ten months and no serious mechanical problems resulted except the failure of the solenoid. The solenoid failure was expected and the replacement solenoid is of a design which is expected to give a long service life. The light application of silicone lubricant spray to the indexing control ratchet arm and cooperating teeth corrected a problem of malfunctioning of the filter wheel indexing mechanism (which occurred on two occasions during the ten months). The prototype system was not intended to be a low maintenance instrument; however, the experience during the durability test with the prototype in continuous operation indicates that the prototype system should operate on a paper machine with an acceptably small amount of down time.

Discussion of Laboratory Testing of FIGS. 3-6

Laboratory Operation of the System of FIGS. 3-6

In the prototype system, potentiometers are included as part of the resistance means 371-377 and 431-437 and are adjusted for the respective positions of the filter wheel 210 to give desired values such as given in the foregoing Table 1. In the preferred system of FIGS. 3-6, these potentiometers for adjusting amplifier gain are omitted and are replaced with fixed resistors 371-377 and 431-437 selected to give scale readings from meter 330 in the respective filter wheel positions which are well above the values given in the preceding Table 1. This is intended to improve the stability and increase the sensitivity of measurement.

In calculating optical parameters from measurements relative to various samples, values were first established for the reflectance RD of the diffuser 135, FIG. 3, in the absence of a paper specimen, for each filter wheel position. Initially calculated values for RD were used in a first computation of optical values, and then the values of RD were adjusted slightly to give the best agreement with the corresponding optical measurements by means of the standard automatic color-brightness tester. The following table shows the reflectance values which were established for certain laboratory testing of the system of FIGS. 3-6.

Table 2

Table Showing Reflectance of the Diffusing Glass With No Paper Specimen Present in a Laboratory Test of the System of FIGS. 1-6

| Filter Wheel Position No. | Symbol | Diffusing Glass Reflectance Value |
|---|---|---|
| 1 | RD1 | 0.349 |
| 2 | RD2 | 0.347 |
| 3 | RD3 | 0.355 |
| 4 | RD4 | 0.349 |
| 5 | RD5 | 0.354 |
| 6 | RD6 | 0.354 |
| 7 | RD7 | 0.349 |

The transmittance of the diffusing glass 135 need not be known since the ratio of the transmittance of the diffusing glass and paper (in series) to the transmittance of the diffusing glass is employed in calculating the desired optical parameters.

A computer program was developed to process the data collected during laboratory operation of the monitoring device 10 as well as to compare the calculated reflectance value $R_{oo}$ and the calculated fluorescent components with the data collected with the standard automatic color-brightness tester. A listing of the symbols employed in a symbolic statement of the computer program in the Fortran computer language utilized in this laboratory study is set forth in Table 3 on the following pages.

Table 3

Listing of Symbols (Including Input Data Symbols and Output Data Symbols With a Brief Indication of Their Significance).

| | Input Data Symbols |
|---|---|
| RSD | OMOD scale reading for reflectance with no paper specimen in place. (Filters 1 through 6.) |
| RSP | OMOD scale reading for reflectance with paper specimen in position. (Filters 1 through 6.) |
| TSD | OMOD scale reading for transmittance with no paper spcimen in place. (Filters 1 through 6.) |
| TSP | OMOD scale reading for transmittance with paper specimen in position. (Filters 1 through 6.) |
| RSD7 | OMOD scale reading for reflectance with no specimen in place. (No. 7 filter.) |
| RSP7 | OMOD scale reading for reflectance with paper specimen in position. (No. 7 filter.) |
| $AR_{oo}FC$ | ACBT reflectance including the fluorescent component. |
| AFC | ACBT fluorescent component. |
| RSD4 | OMOD scale reading for reflectance with no paper specimen in place. (No. 4 filter.) |
| RSP4 | OMOD scale reading for reflectance with paper specimen in position. (No. 4 filter.) |
| GC | Grade Correction as determined by the difference between $R_{oo}FC$ and $AR_{oo}FC$ for each sample and each filter. |
| | Output Data Symbols |
| $R_0$ | Reflectance of a single sheet backed with a black body (no fluorescence) as calculated from OMOD data. |
| T | Transmittance of a single sheet backed with a black body (no fluorescence) as calculated from OMOD data. |
| $R_{oo}$ | Reflectance of an opaque pad (no fluorescence) as calculated from OMOD data. |

Table 3-continued

Listing of Symbols (Including Input Data Symbols and Output Data Symbols With a Brief Indication of Their Significance).

| | |
|---|---|
| $R_{oo}FC$ | Reflectance of an opaque pad (including fluorescence) as calculated from OMOD data. |
| $AR_{oo}FC$ | Reflectance of an opaque pad (including fluoresecence) ACBT. |
| DIFF | Difference between $R_{oo}FC$ and $AR_{oo}FC$. |
| FC | Fluorescent component OMOD. |
| AFC | Fluorescent component ACBT. |
| GC | Grade Correction as determined by the difference between $R_{oo}FC$ and $AR_{oo}FC$ for each sample and each filter. |

Additional Symbols (Used in the Computation of the Output Data from the Input Data)

| | |
|---|---|
| RK | Reflectance correction factor (assigned a value of 1,000 for laboratory operation.) |
| TK | Transmittance correction factor (assigned a value of 1,000 for laboratory operation.) |
| RD | Value representing the absolute reflectance of the diffuser (on a scale of zero to 1.000 as adjusted to give best agreement with optical measurements by means of the standard automatic color brightness tester. (The values given in Table 2 are used for laboratory operation.) |
| RPD | Reflectance of paper specimen when backed with the diffuser, as calculated from current values of RK, RD, RSD, and RSP. |
| TPD | Transmittance of paper specimen and diffuser in series, as calculated from current values of TK, TSD, and TSP. |

In the foregoing listing of symbols, the letters of the symbol OMOD are taken from the phrase on-machine optical device; however, this particular section of the specification refers to a system essentially conforming to the system of FIGS. 3–6 operated to measure optical properties of individual paper sheets under laboratory conditions. (The laboratory work here reported was with an earlier version of the monitoring device designed for on-machine operation, prior to adoption of a thickened shoe plate 122. The standard spacing between the upper and lower sensing heads for the earlier version was ¼ inch, rather than 3/16 inch as with the final version of on-machine device as specifically shown in FIG. 3.) The OMOD scale readings are obtained from the meter 330, FIGS. 5 and 6, with the filter wheel 210, FIGS. 3 and 4, in the respective positions to activate the respective filters 281–286 (indicated as "Filters 1 through 6" in the preceding listing) and to activate filters 287 and 288 (indicated as "No. 7 filter" in the listing), and with switch 331, FIG. 5, in its upper position to measure reflectance, and in its lower position to measure transmittance. As to reflectance measurements, the cavity 145 is considered to form essentially a black body backing for the diffusing glass 135.

The symbol "ACBT" in the foregoing listing of symbols is used to designate a measurement made on the standard commercially available automatic color-brightness tester. The brightness measurement obtained from the ACBT represents a value accepted as standard in the U.S. Paper industry. A further appreciation of the importance of the fact that the OMOD measurements can closely conform to this industry standard is gained from a consideration of the article by L. R. Dearth et al "A Study of Photoelectric Instruments for the Measurement of Color Reflectance, and Transmittance, XVI. Automatic Color-Brightness Tester", *Tappi, The Journal of the Technical Association of the Pulp and Paper Industry*, Vol. 50, No. 2, February 1967, pages 51A through 58A. As explained in this article, the ACBT is photometrically accurate, and the spectral response is correct for the measurement of both color and standard brightness. The spectral response of the ACBT very nearly matches the theoretical CIE functions as indicated by the special technique for determining spectral response. This involves the determination of the tristimulus values for deeply saturated colored glass filters a very rigorous check on the spectral response, especially when it is noted that colored papers are less saturated.

The symbols in the foregoing Listing of Symbols which as shown include lower case characters may also be written exclusively with capital letters. This form of the symbols is convenient for computer printout. The alternate forms of these symbols are as follows: $AR_{oo}FC$ or AROOFC; $R_o$ or RO; $R_{oo}$ or ROO and $R_{oo}FC$ or ROOFC.

Table 4

Symbolic Statement of the Computer Program (Used for Processing the Data Obtained During the Laboratory Operation of the System of FIGS. 3–6)

```
6PS FORTRAN D COMPILER
         C       OMOD (220)
S.0001           WRITE (6,2001)
S.0002   2001    FORMAT (1H , 'SAMPLE', 6X, '
                 RD',12X, 'T', 12X, 'ROO', 9X,
                 'ROOFC', 9X, 1'AROOFC', 10X,
                 'DIFF', 7X 'FC', 7X, 'AFC', 7X,
                 'GC',/)
S.0003           READ (5,1000) RK, TK, RD1,
                 RD2, RD3, RD4, RD5, RD6
S.0004   102     M=O
S.0005           READ (5,1000) RSD4, RSP4
S.0006   1000    FORMAT (10F8.0)
S.0007   100     READ (5,1001) IA, IN, ID, RSD,
                 RSP, TSD, TSP, RSD7, RSP7,
                 AROOFC, AFC, R
S.0008   1001    FORMAT (I2, I2, A4, 9F8, 0)
S.0009           GO TO (11,12,13,14,15,16), IN
S.0010   11      RD=RD1
S.0011           GO TO 17
S.0012   12      RD=RD2
S.0013           GO TO 17
S.0014   13      RD=RD3
S.0015           GO TO 17
S.0016   14      RD=RD4
S.0017           GO TO 17
S.0018   15      RD=RD5
S.0019           GO TO 17
S.0020   16      RD=RD6
S.0021   17      RPD=(RD*RSP*RK)/RSD)
S.0022           RPD4=RD4*RSP4*RK/RSD4
S.0023           TPDOTD=(TSP*TK)/TSD
S.0024           RO=(RPD−(RD*(TPDOTD**2)))/1.-
                 (RD*TPDOTC)**2)
S.0025           T=(TPDOTD*(1.−(RD*RPD)))/(1.-
                 (RD*TPDOTD)**2)
S.0026           A=((1.+(RO**2))−(T**2))/RO
S.0027           ROO=(A/2.)-SOR[(((A/2.)**2)−1.)]
S.0028           RPD7=RD4 *RSP7*RK/RSD7
S.0029           IF (IN−2)1,2,3
S.0030   3       GO TO (7,7,7,4,7,7), IN
S.0031   1       FC=(RPD7−RPD4)*.450
S.0032           GO TO 6
S.0033   2       FC=(RPD7−RPD4)*.570
S.0034           GO TO 6
S.0035   4       FC=(RPD7−RPD4)*.510
S.0036   6       ROOFC=ROO+FC
S.0037           GO TO 30
S.0038   7       ROOFC=ROO
S.0039           FC=0.0
S.0040   30      IF (IA−2)18,19,19
```

Table 4-continued

Symbolic Statement of the Computer Program
(Used for Processing the Data Obtained During the
Laboratory Operation of the System of FIGS. 3-6)

| S.0041 | 18 | ROOFC=ROOFC+R |
|---|---|---|

To indicate more concretely the calculations which are performed, the following Table 5 will illustrate exemplary input and output data for a given sample. The meaning of the various symbols will be apparent from the listing of the symbols of Table 3:

Table 5

Table Showing Exemplary Input and Output Data for a Given Sample

Sample No. 1, white Nekoosa Offset-60 pound paper, specimen A RK=1.000, TK=1.000

| Filter Wheel Position No. Input Data | 1 | 2 | 3 | 4 | 5 | 6 |
|---|---|---|---|---|---|---|
| RD | 0.349 | 0.347 | 0.355 | 0.349 | 0.354 | 0.354 |
| RSD | 0.515 | 0.529 | 0.583 | 0.636 | 0.525 | 0.596 |
| RSP | 1.161 | 1.187 | 1.339 | 1.422 | 1.191 | 1.357 |
| TSD | 1.422 | 1.625 | 1.627 | 1.702 | 1.625 | 1.546 |
| TSP | 0.236 | 0.256 | 0.354 | 0.277 | 0.335 | 0.326 |
| RSD7 | 0.568 | 0.568 | 0.568 | 0.568 | 0.568 | 0.568 |
| RSP7 | 1.381 | 1.381 | 1.381 | 1.381 | 1.381 | 1.381 |
| AROOFC | 0.837 | 0.829 | 0.847 | 0.830 | 0.839 | 0.844 |
| AFC | 0.034 | 0.034 | 0.0 | 0.036 | 0.0 | 0.0 |
| RSD4 | 0.636 | 0.636 | 0.636 | 0.636 | 0.636 | 0.636 |
| RSP4 | 1.422 | 1.422 | 1.422 | 1.422 | 1.422 | 1.422 |
| GC | −0.006 | −0.014 | −0.021 | −0.007 | −0.009 | −0.012 |

Table Showing Exemplary Input and Output Data for a Given Sample - continued

| Filter Wheel Position No. Output Data | 1 | 2 | 3 | 4 | 5 | 6 |
|---|---|---|---|---|---|---|
| RO | 0.779777 | 0.772313 | 0.803330 | 0.773563 | 0.792249 | 0.794690 |
| T | 0.120798 | 0.115319 | 0.155529 | 0.118812 | 0.148337 | 0.151546 |
| ROO | 0.812093 | 0.800173 | 0.874419 | 0.803542 | 0.849399 | 0.856230 |
| ROOFC | 0.836794 | 0.824838 | 0.853419 | 0.831337 | 0.840399 | 0.844230 |
| AROOFC | 0.837000 | 0.829000 | 0.847000 | 0.830000 | 0.839000 | 0.844000 |
| DIFF | −0.000206 | −0.004162 | 0.006419 | 0.001337 | 0.001399 | 0.000230 |
| FC | .0307 | .0387 | .0 | .0348 | .0 | .0 |
| AFC | .0340 | .0340 | .0 | .0360 | .0 | .0 |
| GC | −.006 | −.014 | −.021 | −.007 | −.009 | −.012 |

| S.0042 | | GO TO 20 |
|---|---|---|
| S.0043 | 19 | ROOFC=ROOFC−1 |
| S.0044 | 20 | DIFF=ROOFC−AROOFC |
| S.0045 | | GO TO (21,22), IA |
| S.0046 | 21 | WRITE (6,2000)ID,RO,T,ROO, ROOFC, AROOFC,DIFF,FC,AFC,R |
| S.0047 | 2000 | FORMAT (1H A4,7X,2(F8.6,4X),4 (F10.6,4X),2(F5.,4,4X), '+',F4.3) |
| S.0048 | | TO TO 23 |
| S.0049 | 22 | WRITE (6,2002)ID,RO,T,ROO, ROOFC,AROOFC,DIFF,FC,AFC,R |
| S.0050 | 2002 | FORMAT (1H,A47X, 2(F8.6,4X),4 (F10.6,4X),2(F5.4,4X), '−',F4.3 |
| S.0051 | 23 | M=M+1 |
| S.0052 | | IF (M−6) 100,102,102 |
| S.0053 | END | |
| | | SIZE OF COMMON OOOOO PROGRAM O193O |

END OF COMPILATION MAIN

In the foregoing Table 4, the symbols representing basic mathematicl operations were as follows:

| Operation | Symbol | Example |
|---|---|---|
| Addition | + | A+B |
| Subtraction | − | A−B |
| Multiplication | * | A*B |
| Division | / | A/B |
| Exponentiation | ** | A**B($A^B$) |
| Equality | = | A=B |

In the foregoing table showing exemplary input and output data, the input and output data symbols have been shown as they are actually printed out by the computer with all letters capitalized. In the text, certain of the input and output data symbols are shown in a more conventional manner with subscripts since the symbols are more familiar in such form.

The data such as exemplified in Table 5 are based on a single determination for each specimen. The "grade correction" GC is based on the average difference between $R_{oo}FC$ and $AR_{oo}FC$ for two specimens, specimens A and B.

The data as exemplified in Table 5 show that there is generally good agreement between the calculated $R_{oo}FC$ and $AR_{oo}FC$ values. The spread in values for the duplicate specimens (A and B) is good with the exception of several samples. Some difficulty was experienced in positioning the specimen on the monitoring device 10 to give reproducible results. The difficulty should be minimized when the unit is placed "on-machine". The grade correction GC takes this discrepancy into consideration so the correction should be established "on-machine".

The RD values shown in Table 5 were punched into the first data card along with the values for RK and TK for input to the computer in advance of a desired computation. The factors RK and TK were included as factors in the computations so that the transmittance and reflectance values could be adjusted independently, if desired. In this evaluation, RK and TK were left at 1.000. (Calculated values for RD were used in a first computer run and then the values were adjusted slightly to give the best agreement with the standard automatic color-brightness tester. The values for RD shown in Table 5 are the slightly adjusted values utilized in obtaining the data discussed in this section of the specification.)

A second set of data for the same fourteen samples was collected using the monitoring device in the same condition as for the collection of the data previously given. All of the variables were left the same to see how closely the data could be reproduced for the identical specimens. The agreement was quite good except for samples 8 and 14. It appears that the paper may not have been lying flat in one or the other tests. The grade correction GC on some of the grades was changed and the second set of data was again calculated for samples 1, 2, 4, 5, 6, 8 and 14. This improved the agreement between the monitoring device and the standard automatic color-brightness tester.

The reflectance head of the monitoring device was then lowered 0.025 inch and another set of data was collected for the same seven samples. The same ACBT data was used. The data show that lowering the reflectance head reduces the reflectance while transmittance remains essentially unchanged. The effects are not as large as was expected and could be corrected through adjustment of RK; however, the variables RK, TK and GC were again held constant.

The reflectance head was then raised to a spacing of 0.050 inch (0.025 inch above the normal position for these tests), and another set of data was collected for the same seven samples. The effects were larger than when the reflectance head 11 was lowered. Again, an adjustment of RK would improve the agreement.

It was concluded from these test results that a change of plus or minus 0.025 inch from "normal position" is larger than can be tolerated. An estimate of a reasonable tolerance, based on this and earlier work, would be plus or minus 0.010 inch from "normal position".

All of the variables used in calculating the data for samples 1, 2, 4, 5, 6, 8 and 14, after the initial change in the grade correction GC, were held the same to determine the effects of changing the reflectance head position. The same input data for the case of the reflectance head being raised 0.025 inch were processed again but with RK equal to 0.975 instead of 1.000. This reduces the reflectance value to the proper level. The data obtained in this way show good agreement between the monitoring device and the standard automatic color-brightness tester. Apparently the factor RK can be used quite effectively in adjusting for some variation in the geometric relationship of the upper and lower sensing heads. It would be preferred, of course, to maintain proper alignment and spacing.

A second set of samples were evaluated after returning the reflectance head to its normal spacing from the transmittance head. Before calculating new output data, the computer program of Table 4 was corrected in statements S.0022 and S.0028 by changing RD to RD4. The corrected computer program has been shown herein since tthe error in the previously referred to data was insignificant in most cases. Thus with the corrected computer program, the inut data for the second set of samples were processed. The values RK and TK were set to 1.000 and the same grade corrections were used as for samples 1, 2, 4, 5, 6, 8 and 14 previously referred to.

Conclusions drawn from all of the data are that the grade correction GC will handle errors resulting from less than ideal characteristics of the monitoring device 10 such as the relatively wide bandwidth of light transmitted in the various filter positions in comparison to the requirements of Kubelka-Munk theory and the fact that this theory applies strictly only to diffuse light rather than collimated light as actually employed in the illustrated monitoring device 10. This correction must be established "on-machine". Use of the diffusing glass 135 to calibrate the monitoring device 10 will handle changes in light level, photocell sensitivity and amplifier again. The reflectances RD of the diffusing glass 135 for the various filters as established in the present work are set forth in the previous Table 2 entitled "Table Showing Reflectance of the Diffusing Glass With No Paper Specimen Present in a Laboratory Test of the System of FIGS. 1-6".

As previously mentioned, the transmittance of the diffusing glass 135 need not be known as the ratio of the transmittance of the diffusing glass and paper (in series), identified by the symbol TSP, to the transmittance of the diffusing glass 135, identified by the symbol TSD, is employed as will be apparent from the explanation of the calculations employed set forth hereinafter.

The fluorescent component is handled through the difference in reflectance as measured with the number 4 and the number 7 filters (RPD7 minus RPD4). The factors used in the subject computations, for filters number 1, 2 and 4, are 0.500, 0.600 and 0.550 respectively. This means of determining the fluorescent contribution FC appears to be successful.

The factor RK whereby the reflectance can be adjusted to account for misalignment or incorrect spacing seems to function better than was expected.

The following examples will serve to explain the calculations of the output data for the different filter positions in greater detail.

Table 6- Table Showing Exemplary Calculation of Paper Optical Parameters

Calculation of $R_o$, T, $R_{oo}$, FC and $R_{oo}FC$ from OMOD data with the No. 1 filter in position.

Input: RSD1, RSP1, TSD1, TSP1, RSD7, RSP7, TK, RK, RSD4, RSP4, RD1, RD4, and GC1

Calculation:

$RPD1 = (RD1 \times RSP1 \times RK)/RSD1$ $RPD4 = (RD4 \times RSP4 \times RK)/RSD4$ $RPD7 = (RD4 \times RSP7 \times RK)/RSD7$ $TPD/TD = (TSP1 \times TK)/TSD1$ $R_o = [RPD1 - RD1(TPD/TD)^2]/[1 - (RD1(TPD/TD)^2)]$ $T = [(TPD/TD)(1 - (RD1 \times RPD1))]/[1 - (RD1(TPD/TD)^2)]$ $A = (1 + R_o^2 - T^2)/R_o$ $R_{oo} = (A/2) - \sqrt{(A/2)^2 - 1}$ $FC = 0.500 (RPD7 - RPD4)$ $R_{oo}FC = R_{oo} + FC + GC1$ Calculation of $R_o$, $T$, $R_{oo}$, FC and $R_{oo}$FC from OMOD data with the No. 2 filter in position
Input: RSD2, RSP2, TSD2, TSP2, RSD7, RSP7, TK, RK, RSD4, RSP4, RD2 and GC2.
Calculation:

$$RPD2=(RD2\times RSP2\times RK)/RSD2$$

$$RPD4=(RD4\times RSP4\times RK)/RSD4$$

$$RPD7=(RD4\times RSP7\times RK)/RSD7$$

$$TPD/TD=(TSP2\times TK)/TSD2$$

$$R_o=[RPD2-(RD2(TPD/TD)^2)]/[1-(RD2(TPD/TD)^2)]$$

$$T=[(TPD/TD)(1-(RD2\times RPD2))]/[1-(RD2(TPD/TD)^2)]$$

$$A=(1+R_o^2-T^2)/R_o$$

$$R_{oo}=(A/2)-\sqrt{(A/2)^2-1}$$

$$FC=0.600(RPD7-RPD4)$$

$$R_{oo}FC=R_{oo}+FC+GC2$$

Calculation of $R_o$, $T$, $R_{oo}$, FC and $R_{oo}$FC from OMOD data with the No. 3 filter in position
Input: RSD3, RSP3, TSD3, TSP3, TK, RK, RD3 and GC3
Calculation:

$$RPD3=(RD3\times RSP3\times RK)/RSD3$$

$$TPD/TD=(TSP3\times TK)/TSD3$$

$$R_o=[RPD3-(RD3(TPD/TD)^2)]/[1-(RD3(TPD/TD)^2)]$$

$$T=[(TPD/TD)(1-(RD3\times RPD3))]/[1-(RD3(TPD/TD)^2)]$$

$$A=(1+R_o^2-T^2)/R_o$$

$$R_{oo}=(A/2)-\sqrt{(A/2)^2-1}$$

$$FC=0.0$$
$$R_{oo}FC=R_{oo}+FC+GC3$$

Note: The calculations for Filters No. 5 and 6 are carried out in the same manner as for filter No. 3 except that the appropriate filter data are employed. FC is made equal to zero for filters No. 3, 5 and 6 for all samples.

Calculation of $R_o$, $T$, $R_{oo}$, FC and $R_{oo}$FC from OMOD data with the No. 4 filter in position.
Input: RSD4, RSP4, TSD4, TSP4, RSD7, TK, RK, RD4 and GC4.
Calculation:

$$RPD4=(RD4\times RSP4\times RK)/RSD4$$

$$RPD7=(RD4\times RSP7\times RK)/RSK7$$

$$TPD/TD=(TSP4\times TK)/TSD4$$

$$R_o=[RPD4-(RD4(TPD/TD)^2)]/[1-(RD4(TPD/TD)^2)]$$

$$T=[(TPD/TD)(1-(RD4\times RPD4))]/[1-(RD4(TPD/TD)^2)]$$

$$A=(1+R_o^2-T^2)/R_o$$

$$R_{oo}=(A/2)-\sqrt{(A/2)^2-1}$$

$$FC=0.550(RPD7-RPD4)$$

$$R_{oo}FC=R_{oo}+FC+GC4$$

On the basis of further experimental data, the factors relating the fluorescent component, as measured on the monitoring device, to the fluorescent component as measured with the standard automatic colorbrightness tester, have the following presently preferred values for filter wheel position numbers 1, 2 and 4: 0.528, 0.636, and 0.456, respectively.

Discussion of the On-Machine System of FIGS. 1–6

Set Up Procedure For the System of FIGS. 1–6

In the prototype system, potentiometers were included as part of the gain control resistance means and were adjusted for the respective positions of the filter wheel 210 to give values correlated directly with absolute reflectance and transmittance of the diffusing glass, such as given in the foregoing Table 1. In the preferred system of FIGS. 1–6, however, these potentiometers for adjusting amplifier gain are omitted and are replaced with fixed resistors 371–377 and 431–437 selected to give scale readings from meter 330 in the respective filter wheel positions which are well above the values given in Table 1. The higher gain values selected for the amplifiers 361 and 429 in the preferred system are intended to provide improved stability and increased sensitivity of measurement.

The upper and lower sensing heads are placed at a spacing of 3/16 inch by means of a gauging plate made of 3/16 inch Teflon. The incident beam 133 forms a light spot of elliptical configuration on the planar upper and surface 98 of the diffusing window 135. The major axis of the elliptical light spot has a length of about ⅝ inch and is parallel to the direction of web movement, i.e. the machine direction, while the minor axis has a length of about ⅜ inch and is at right angles to the machine direction. The reflected beam 137 consists of the total light reflected from a circular spot of approximately ⅜ inch diameter. This viewed area lies substantially within the ellipitcal illuminated area on surface 98; however, the two essentially coincide in the direction of the minor axis of the illuminated spot.

Since the effective optical aperture 154, FIG. 3, of the lower sensing head is of a diameter of about 15/16 inch, the system will be insensitive to a certain amount of lateral offset between the optical axis 15 of the upper sensing head and the optical axis 515 of the lower sensing head.

In setting up the system, the position of the lower sensing head may be adjusted laterally so that the spot formed by the incident beam 133 is essentially centered on the surface 98 of window 135.

The optimum relationship between the upper and lower sensing heads can be precisely detected by observing the reflectance output from the upper sensing head (in any position of the filter wheel 210) as the heads are moved relative to one another while maintaining the spacing of 3/16 inch between the heads. When the correct geometrical relationship is attained between the incident beam 133, the reflected beam path 137 and the plane of the surface 98 of the window 135, the reflectance signal will have a maximum value.

With the upper and lower sensing heads in the optimum geometric relationship, and with the incident beam impinging on the central part of surface 98, it is considered that relative shifting between the upper and lower heads in the plane of surface 98 over a range of plus or minus ⅛ inch in any lateral direction should have an insignificant effect because of the flat planar configuration of surface 98.

Direct Digital Control Analog Point Scan Subroutine of FIG. 7

The program subroutine of FIG. 7 accepts digital information from the analog to digital converters of component 501, FIG. 6, at one second intervals. Referring to FIG. 7 where the blocks containing the flow chart steps are individually numbered in their operational sequence, the step 701 represents the entry into the subroutine at one second intervals. Step 702 shows the acceptance of an analog input and conversion to engineering units. Step 703 indicates saving such converted input as a process variable in a scan only file of the digital control computer. A type of control computer which has utilized such a scan program for a number of years for collecting data in an overall paper machine direct digital control system is the General Electric Company PAC 4020 Process Control Computer. Minor additions to the existing program routine will allow for the collection of the reflectance and transmittance data by means of the existing computer system. A suitable computer interface between monitoring device 10 and such a control computer has been described previously. Block 702 suggests that valid reflectance and transmittance values might be limited to a range from 0 to 1.0 units, for example. In this event the program could include provision for checking that the collected reflectance and transmittance values were within the range and for printing out a message or the like if invalid data is received.

Block 704 indicates the sequential reading of process data input points in a predetermined order until the last data input point has been scanned, whereupon the computer exits from the subroutine.

Process File (FILE X) for the Data Acquisition and Data Reduction Programs

The arrangement of FILE X which is utilized during acquisition of data from the system of FIGS. 1–6 and conversion thereof to desired output paper optical quantities can be visualized from the following Table 7. In the first column of Table 7, sequential memory locations of the process file have been assigned sequential numbers beginning with zero. A convenient label has been assigned to certain groups of sequential memory locations, and this is also given in the first column. (The term FILE X is used to designate all of the locations zero through one hundred forty while subsequent labels refer to only the subadjacent group of sixteen locations or less.)

In general the significance of the various stored data will be apparent from the descriptions given in the righthand column of Table 7 and from the use of the stored data as indicated by the flow charts of FIGS. 8–20.

Table 7
FILE X (Process File For the Data Acquisition and Data Reduction Programs)

| Label and Relative Location of File | Location Description of Stored Data |
|---|---|
| FILE X | |
| 0 | STATUS |
| 1 | PCW ADR LOOP P (REFLECTION CELL) |
| 2 | PCW ADR LOOP Q (TRANSMISSION CELL) |
| 3 | PFA GAGE HEAD POSITION (TAG 129) |
| 4 | SLOW DOWN COUNT |
| 5 | SLOW DOWN INITIAL VALUE COUNT |
| 6 | FILTER WHEEL POSITION INDEX EST. (I) |
| 7 | PFA BASIS WEIGHT AVG. (TAG. B00) |
| 8 | MINIMUM ON SHEET HEAD POS. |
| 9 | INITIALIZATION INDEX (K) |
| 10 | FILTER WHEEL CYCLE COMPLETION INDEX (CYCLE) |
| 11 | SMOOTHING CONSTANT (ALPHA) |
| CTABL | |
| 12 (0,0) | STANDARDIZATION CORR. FACTOR, CTABLE = (C) |
| 13 (1,0) | |
| 14 (2,0) | |
| 15 (3,0) | |
| 16 (4,0) | |
| 17 (5,0) | |
| 18 (6,0) | |
| 19 (7,0) | SPARE |
| 20 (0,1) | |
| 21 (1,1) | |
| 22 (2,1) | |
| 23 (3,1) | |
| 24 (4,1) | |
| 25 (5,1) | |
| 26 (6,1) | |
| 27 (7,1) | SPARE |
| STTABL | |
| 28 (0,0) | STANDARDIZATION INPUT DATUM, ST = (R*) |
| 29 (1,0) | |
| 30 (2,0) | |
| 31 (3,0) | |
| 32 (4,0) | |
| 33 (5,0) | |
| 34 (6,0) | |
| 35 (7,0) | SPARE |
| 36 (0,1) | ,″ = (T*) |
| 37 (1,1) | |
| 38 (2,1) | |
| 39 (3,1) | |
| 40 (4,1) | |
| 41 (5,1) | |
| 42 (6,1) | |
| 43 (7,1) | SPARE |
| RGTABL | |
| 44 (0,0) | NOMINAL BACKING REFLECT., RG = (Rg) |
| 45 (1,0) | |
| 46 (2,0) | |
| 47 (3,0) | |
| 48 (4,0) | |
| 49 (5,0) | |
| 50 (6,0) | |
| 51 (7,0) | SPARE |
| 52 (0,1) | NOMINAL DIFFUSER TRANS. ″ = (Td) |
| 53 (1,1) | |
| 54 (2,1) | |
| 55 (3,1) | |
| 56 (4,1) | |
| 57 (5,1) | |
| 58 (6,1) | |
| 59 (7,1) | SPARE |
| VTABL | |
| 60 (0,0) | CORRECTED & SMOOTHED INPUT, NFCELL=R |
| 61 (1,0) | |
| 62 (2,0) | |

Table 7-continued
FILE X (Process File For the Data Acquisition and Data Reduction Programs

| Label and Relative Location of File | Location Description of Stored Data | |
|---|---|---|
| 63 (3,0) | | |
| 64 (4,0) | | |
| 65 (5,0) | | |
| 66 (6,0) | | |
| 67 (7,0) | SPARE | |
| 68 (0,1) | " = TDP | |
| 69 (1,1) | | |
| 70 (2,1) | | |
| 71 (3,1) | | |
| 72 (4,1) | | |
| 72 (5,1) | | |
| 74 (6,1) | | |
| 75 (7,1) | SPARE | |
| SGTABL | | |
| 76 (0,0) | REFLECTANCE SPECIFIC GRADE CORR., SGCF | |
| 77 (1,0) | | |
| 78 (2,0) | | |
| 79 (3,0) | | |
| 80 (4,0) | | |
| 81 (5,0) | | |
| 82 (6,0) | | |
| 83 (7,0) | SPARE | |
| 84 (0,1) | TRANSMITTANCE SPECIFIC GRADE CORR. | |
| 85 (1,1) | | |
| 86 (2,1) | | |
| 87 (3,1) | | |
| 88 (4,1) | | |
| 89 (5,1) | | |
| 90 (6,1) | | |
| 91 (7,1) | SPARE | |
| OUTABL | | |
| 92 (0) | PRINTING OPACITY | (POPAC) |
| | Y REFL = ILLUM.A-.89 BACKING | (YAR89) |
| 94 (2) | TAPPI OPACITY | (TOPAC) |
| 95 (3) | X-TRI.STIMULUS | (XTRI) |
| 96 (4) | Y-TRISTIMULUS | (YTRI) |
| 97 (5) | Z.TRISTIMULUS | (ZTRI) |
| 98 (6) | HUNTER L | (LH) |
| 99 (7) | HUNTER A | (AH) |
| 100 (8) | HUNTER B | (BH) |
| 101 (9) | BRIGHTNESS WITH FLUOR. % INF. | |
| | BACKING | (BRRINF) |
| STABL | | |
| 102 (0) | SCATTER COEFFICIENT | (S) |
| 103 (1) | | |
| 104 (2) | | |
| 105 (3) | | |
| 106 (4) | | |
| 107 (5) | | |
| 108 (6) | | |
| 109 (7) | SPARE | |
| KTABL | | |
| 110 (0) | ABSORPTION COEFFICIENT | (K) |
| 111 (2) | | |
| 113 (3) | | |
| 114 (4) | | |
| 115 (5) | | |
| 116 (6) | | |
| 117 (7) | SPARE | |
| RSTABL | | |
| 118 (0,0) | STANDARDIZATION BACKING REFL REFERENCE (Rs) | |
| 119 (1,0) | | |
| 120 (2,0) | | |
| 121 (3,0) | | |
| 122 (4,0) | | |
| 123 (5,0) | | |
| 124 (6,0) | | |
| 125 (7,0) | SPARE | |
| 126 (0,1) | STANDARDIZATION DIFFUS. TRANS. REFERENCE (Ts) | |

Table 7-continued
FILE X (Process File For the Data Acquisition and Data Reduction Programs

| Label and Relative Location of File | Location Description of Stored Data | |
|---|---|---|
| 127 (1,1) | | |
| 128 (2,1) | | |
| 129 (3,1) | | |
| 130 (4,1) | | |
| 131 (5,1) | | |
| 132 (6,1) | | |
| 133 (7,1) | SPARE | |
| MPAR | | |
| 134 (0) | FLUOR SLOPE EMPIRICAL CONSTANT | |
| 135 (1) | $X_b$-FLUOR /Z-FLUOR. RATIO | FCON |
| 136 (2) | Br-FLUOR /Z-FLUOR RATIO | FCON |
| 137 (3) | RESET VALUE OF FILTER CYCLE INDEX | ICYCLE |
| 138 (4) | BASIS WT AVG. (FLOATING POINT) | BW |
| 139 (5) | EMPIRICAL OVERALL REFL. CORR. FACTOR | CORR |
| 140 (6) | EMPIRICAL OVERALL TRANS. CORR. FACTOR | CORR |

In referring to locations of FILE X in the program flow charts of FIGS. 8–20, the relative location of FILE X is indicated by the number in parenthesis. Thus FILE X(4) refers to relative location number four of FILE X as given in Table 7. FILE X(138) corresponds to MPAR(4) in Table 7, and both refer to relative location number one hundred and thirty eight. FILE X(four) is an alternative to FILE X(4), an is used in the text to avoid any possible confusion with drawing reference numerals.

The following general discussion of successive locations or groups of locations of FILE X, taken in numerical order, will serve as an introduction of the description of the program routines of FIGS. 8–20. Contemplated modifications of the programs and of FILE X will be discussed in a later section.

In location O of FILE X, the Status word includes a bit number 23 which is set to a logical one when conditions are met for making standardizing calculations. For example, the OMOD should be off sheet and the beta gauge with which the OMOD is mounted for scanning movement should be in its standardizing mode. The set condition of bit 23 is responded to by the program to bypass data smoothing and to store data in a special table STTABLE at locations 28–34 and 36–42 of Table 7. The condition of bit 23 is reset to logical zero when the filter wheel has indexed through seven positions or if the beta gauge completes standardization before the complete set of OMOD standardization data is collected.

Locations 1 and 2 of FILE X may store the PCW (process control word) addresses for Loops P and Q. Loop P is a subroutine for controlling the processing of reflectance data and Loop Q is concerned with the processing of transmittance data. These loops begin at FIG. 13 of Program Fourteen.

Location three of FILE X, contains the address of the DDC scanner file containing the position of the sensing head 10 along its path of traverse of the web. This position is monitored by the Scan-Only (DDC) routine of FIG. 7 and is stored in the scan system file identified by TAG one hundred twenty nine. A current value of sensing head position is transferred from the referenced DDC file into location three of FILE X periodically.

Location four of FILE X stores a SLOWDOWN COUNT index value which is used to cause a specified number of dummy readings at each filter wheel position to be made after each advance of the filter wheel to allow time for the OMOD electronics to reach steady state, and to allow for any transient error in synchronization between the DDC Scan-Only routine of FIG. 7 and the Data Reduction routine (Program Fourteen) of FIGS. 8-16 which runs at one second intervals under the control of the RTMOS Scheduler (a computer real time operating system of the General Electric Co.).

Location five of FILE X stores a SLOWDOWN INITIAL VALUE COUNT which is used when a processing cycle is being initiated.

Location six of FILE X of Table 7 stores an index value I which represents the estimated filter wheel position, based on the number of actuations of the filter wheel indexing solenoid, since the initial filter wheel position wherein reed switch 358, FIG. 6, is closed in response to the proximity of permanent magnet 243, FIGS. 3 and 6. In the computer program, the successive filter wheel positions are designated 0, 1, 2, 3, 4, 5 and 6, and result in spectral response distributions designated $B_R$ (brightness), $X_B$ (blue portion of the $E_c\bar{x}$ function), $X_R$ (red portion of the $E_c\bar{x}$ function), Z ($E_c\bar{z}$ function without fluorescence), $Y_C$ ($E_c\bar{y}$ function), $Y_A$($E_a\bar{y}$ function), and $Z_{FL}$($E_c\bar{z}$ function, with fluorescence).

Location seven of FILE X serves to store the address of the DDC file for basis weight average. TAG BOO, which is used by Program Fourteen to access the basis weight data and store it in location MPAR (4) in floating point format. This will be used by Program Forty-Two during the reduction of data.

Location eight of FILE X stores a value for the minimum onsheet head position. When the head position is less than such minimum value, a standardization cycle may be set in motion by Program Fourteen.

Location nine of FILE X contains the value of an initialization index K which is used to determine when all seven smoothed input values have been initialized to equal the latest unsmoothed input for each of the reflectance and transmittance channels.

Location ten of FILE X stores a filter wheel cycle completion index designated CYCLE that can be used to determine when a specified number of filter wheel cycles have been completed through the last filter wheel position (position six in the programming notation). This prevents the data reduction program (Program Forty-Two) of FIGS. 17-20 from running until a specified number of data sets have been collected since the last time it ran or the unit was standardized.

Figure 14:
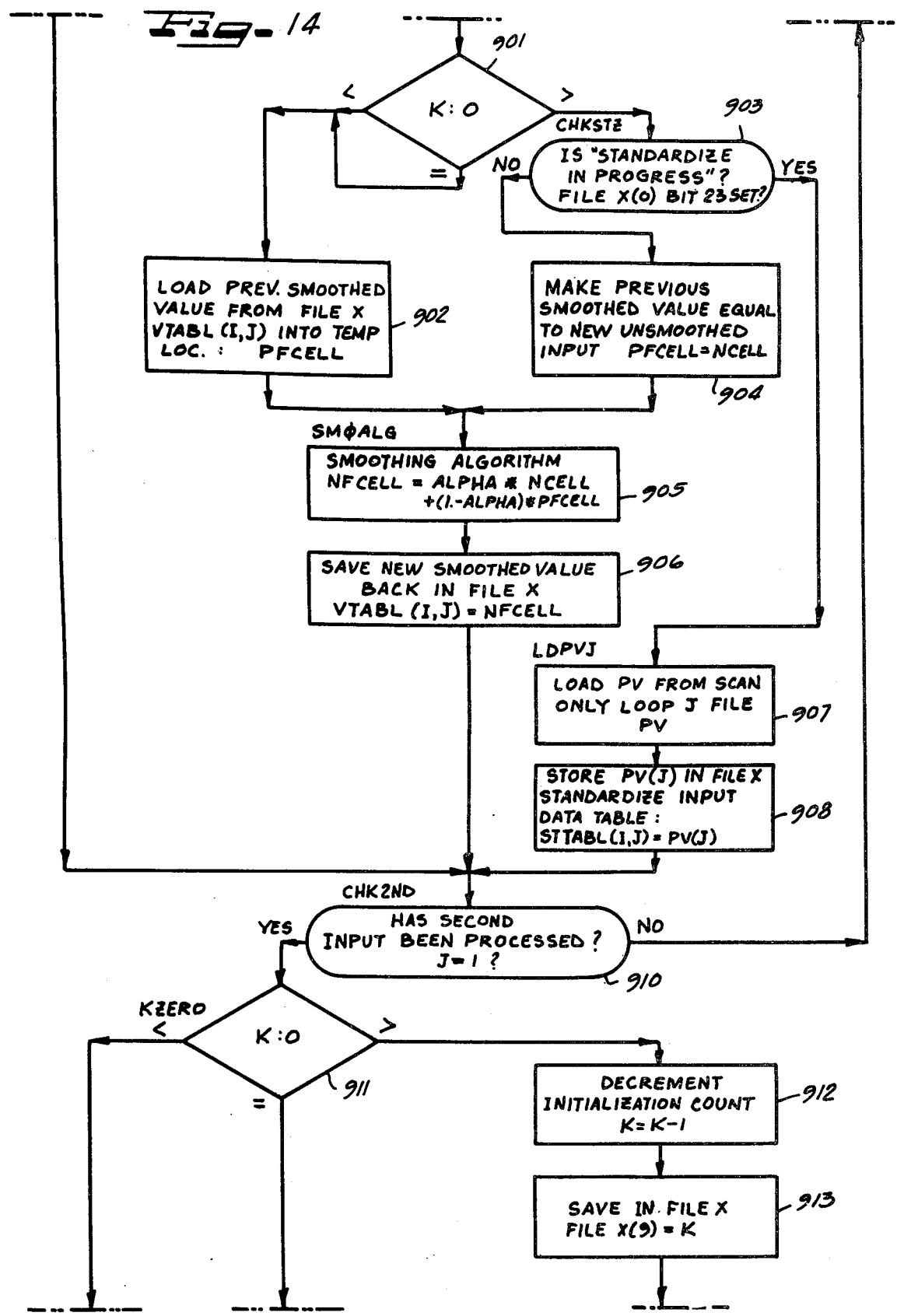

Location eleven of FILE X stores a smoothing constant ALPHA which is used in smoothing the input data from FIGS. 1-6 by Program Fourteen, as indicated in FIG. 14.

A temporary location index J is used to point to either the reflectance vector tables or the transmittance vector tables. J is equal to zero to indicate reflectance, and is equal to one to designate transmittance. Each of the tables such as CTABL of table 7 has a first set of locations (e.g. 12 through 18) which can become active while J is equal to zero and a second set of locations (e.g. 20 through 26) which can be selected when J is equal to one. Thus the sets of two numerals in parenthesis at locations 12 through 133 represent respectively the value of the filter wheel position index I and the J index value corresponding to the location.

The table CTABL at locations 12-18 and 20-26 of the process file of Table 7 is used to store a standardization correction factor C. The reflection values of the factor C for the respective filter wheel positions are stored in locations 12-18 and are active when J=0, and I=0, 1, 2, 3, 4, 5 and 6, respectively. Similarly the transmission values for the lower sensing head and the respective filter wheel positions are stored in locations 20-26, which are selected when J=1 and I=0, 1, 2, 3, 4, 5 and 6, respectively.

The table ST TABL, stores data from the OMOD system of FIGS. 1-6 in the standardization mode with the heads in the off-sheet position.

The table RG TABL stores the value RG, the nominal reflectance of the backing for the web in the off-sheet position, for the respective filter wheel positions, and also the value TD, the nominal transmittance of the diffusing window 135 in the off-sheet position. These values may be experimentally determined as previously explained and inserted into table RG TABL at start up of the system.

Table VTABL serves to store input data after it has been processed by Program Fourteen of FIGS. 8-16. The raw data is corrected on the basis of the most recent standardization values from table ST TABL and, multiplied by the correction factors C from table CTABL, and exponentially smoothed by means of the subroutine of FIG. 14 before being stored in the VTABL locations.

The SG TABL table of the process file of Table 7 stores the specific grade correction factors SGCF.

The OUTABL locations store the output quantities as computed under the control of the Data Reduction Program Forty Two of FIGS. 17-20.

The tables STABL and KTABL store the scatter coefficient S and the absorption coefficient K which together serve to characterize the paper web being monitored.

Optical Property Data Acquisition Subroutine of FIGS. 8-16 (Program Fourteen)

The subroutine of FIGS. 8-16 is referred to as Program Fourteen (or Program 14) and is designed to perform various data acquisition functions as indicated in the flow chart.

It is believed that the flow chart of FIGS. 8-16 will be self-explanatory given the foregoing comments concerning Table 7. The following Tables 8-16 are a tabulation of the blocks of the subroutine with supplementary comments to indicate the meaning of any abbreviations, or to paraphrase any possibly cryptic statements. (Arabic numerals within the blocks in FIGS. 8-20 do not refer to reference numerals of FIGS. 1-6. This is indicated in the following tabulation by spelling of such numerals so far as feasible.)

Table 8

| Supplementary Explanation of the Program Steps of FIG. 8 | |
|---|---|
| Program Step | Comment |
| 801 | Program Fourteen initial point at start up. |
| 802 | The timer location designated AUXTM +3 receives an intial value. (Equal to the present time). |
| 803 | The point of entry each time the timer |

Table 8-continued

Supplementary Explanation of the Program Steps of FIG. 8

| Program Step | Comment |
|---|---|
| | location AUX-TIME reaches a value L, i.e. every one second. |
| 804 | Load the starting address of File X into index register three. |
| 805 | Load PCW (process control word) addresses of loops P and Q from locations one and two of FILE X. (See Table 7.) |
| 806 | Are scan bits in both of the process control words referred to in block 805 set for off-scan |
| 807 | If decision at block 806 is no, calculate the next time for Program Fourteen to run DLYTIM (delay time) seconds from the present time. (The value of DLYTIM is nominally one second.) Add DLYTIM to the present value of AUXTM+3 to register a new time AUXTM+3. |
| 808 | Load value of SLOWDOWN COUNT from location four of FILE X into the temporary register SLODWN. |
| 809 | Decrement the count in SLODWN by one. |
| 810 | If answer to decision of block 806 is yes, turn Program Fourteen off and exit from the program. |

Table 9

Figure 9:
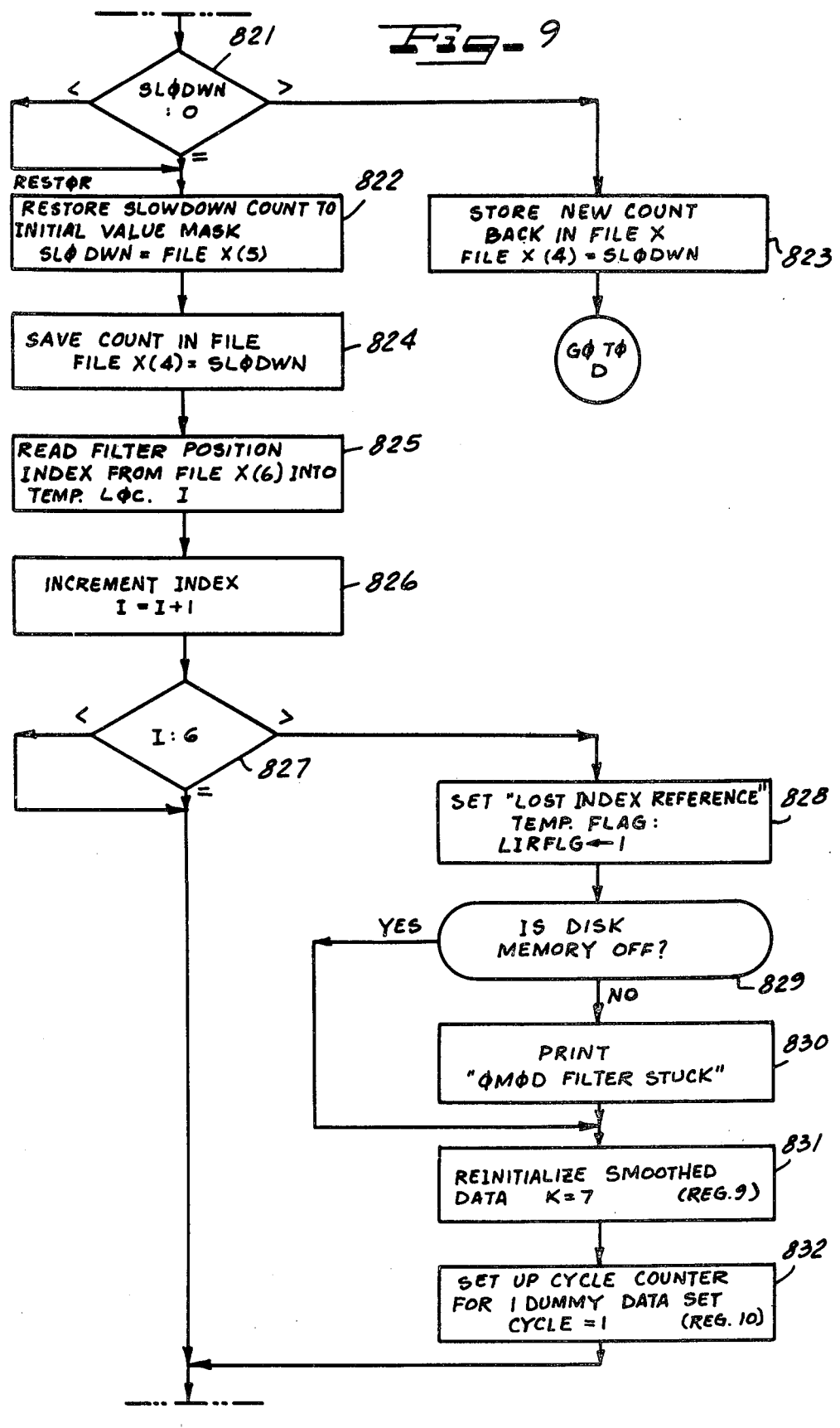

Supplementary Explanation of the Program Steps of FIG. 9

| Program Step | Comment |
|---|---|
| 821 | Compare the count value in SLODWN with zero, If SLODWN is equal to or less than xero, go to block 822. If SLOWDN is greater than zero, go to block 823. |
| 822 | Insert SLOW DOWN INITIAL VALUE COUNT from FILE X(five) into the SLODWN register. |
| 823 | Store the decremented count value in SLODWN in SLOW DOWN COUNT at FILE (X(four), and go to point D of the program, shown in FIG. 16. |
| 824 | Place the count transferred from FILE X(five) at block 822 into FILE X(four) labeled SLOW DOWN COUNT. |
| 825 | Read content of FILE X(six) into temporary location I. |
| 826 | Add one to temporary location I. |
| 827 | Compare I and six; if I equal to or less than six, go to LDDIDG, block 841 of FIG. 10; if I is greater than six, go to block 828. |
| 828 | Put a one in temporary flag location LIRFLG. |
| 829, 830 | If disk memory is operating print out that the indicated message. |
| 831 | Set the K value in location nine of FILE X to seven. |
| 832 | Set CYCLE value in locaton ten of FILE X to one, and go to LDDIDG, block 841, FIG. 10. |

Table 10

Figure 10:
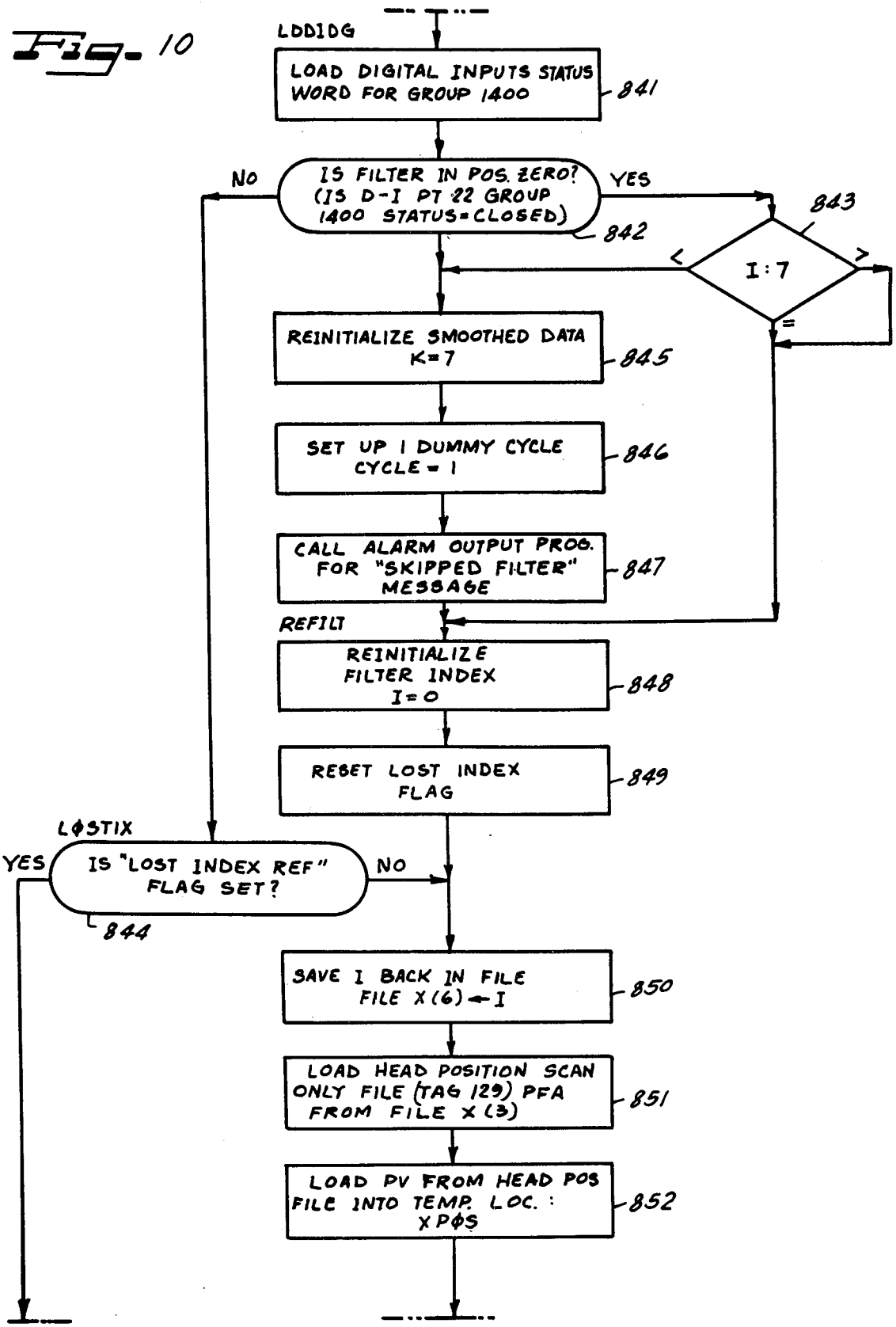

Supplementary Explanation of the Program Steps of FIG. 10

| Program Step | Comment |
|---|---|
| 841 | Load the contents of the memory location that indentifies the status of the digital input group (Group 1400) to which the zero position filter contacts 358, FIG. 6, are connected. |
| 842 | Is the filter wheel in position zero, i.e. the position shown in FIG. 3 This is determined from bit position twenty-two of the STATUS word loaded in step 841. If bit position twenty-two indicates that the contacts of reed switch 358, FIG. 6, are closed, then go to block 843. If the contacts are open, go to LOSTIX, block 844. |
| 843 | If value in temporary location I is less than seven, go to block 845. If I is equal to or greater than seven go to REFILT, block 848. |
| 844 | Is a value one in the temporary flag location LIRFLG (See block 828, FIG. 9.) |
| 845 | Set FILE X (nine) to seven. |
| 846 | Set FILE X (ten) to one. |
| 847 | If the filter wheel is indexing properly, the I value will be incremented by the step of block 826, FIG. 9, so that I will equal seven at block 843. Since I was less than seven, apparently the filter wheel has failed to index each time it was commanded to do so. Block 847 provides for the print out by means of an alarm output program under these conditions. |
| 848 | Set location six of FILE X to zero. |
| 849 | Set LIRFLG to zero. |
| 850 | Insert current value of I in FILE X (six). |
| 851 | Load the head traverse position File Address from FILE X(three). |
| 852 | Load the process variable (PV) of block 851 into the temporary location XPOS. |

Table 11

Figure 11:
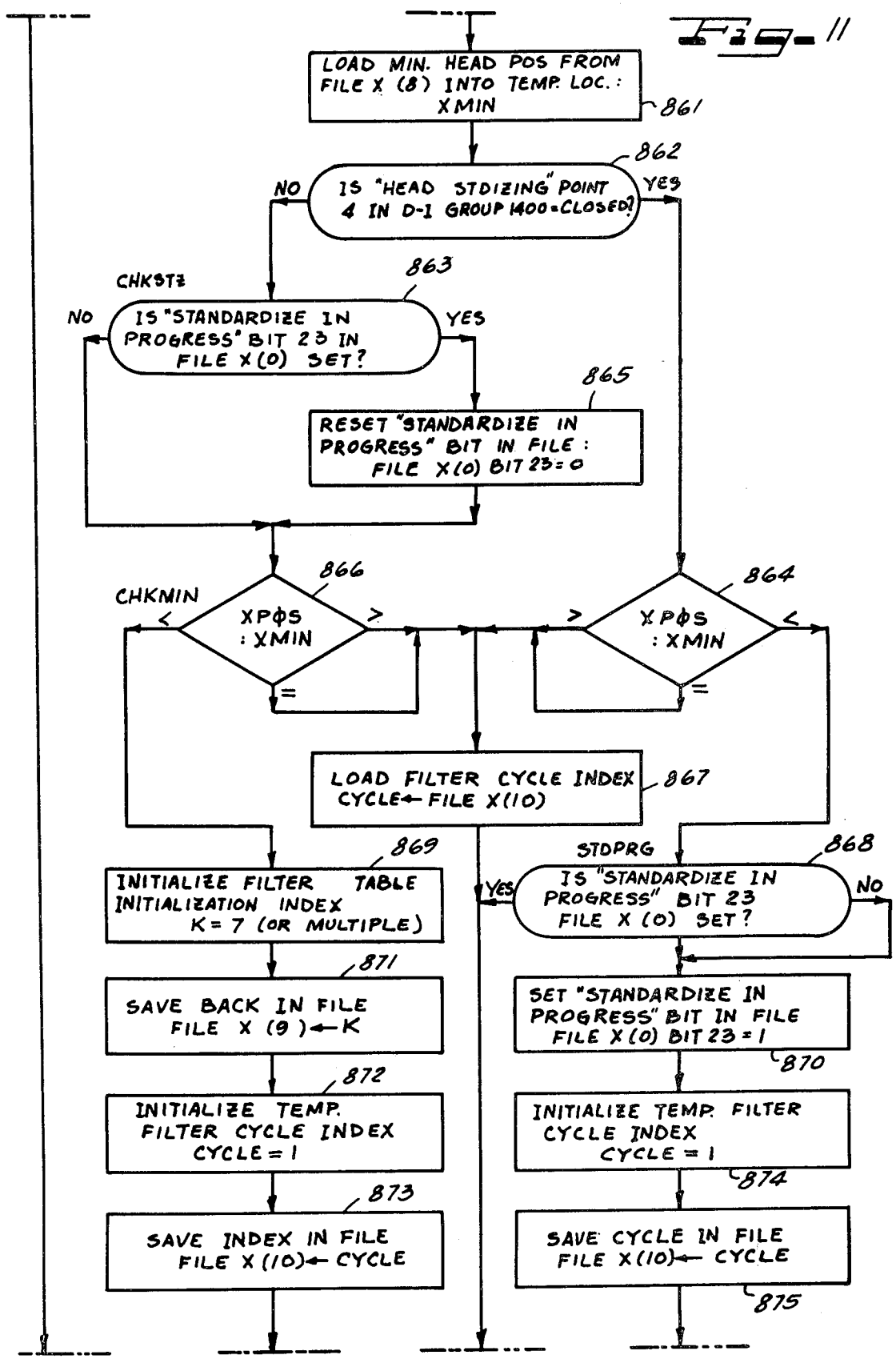

Supplementary Explanation of the Program Steps of FIG. 11

| Program Step | Comment |
|---|---|
| 861 | Load the content of FILE X(eight) into the temporary location XMIN. |
| 862 | Is the beta gauge in a standardizing mode as indicated by point four in the digital input status word for group fourteen hundredv. Point four refers to the bit four position of the status word. If the beta gauge is not in standardizing mode, go to CHKSTZ at block 863. If beta gauge is in standardizing mode, go to block 864. |
| 863 | Is the OMOD shown to be in standardizing mode by bit position twenty three of FILE X (zero). If the OMOD is being standardized, go to block 865. If standardization is not in progress go to block 866. |
| 864 | Compare the value of XPOS(See block 852 FIG. 10) with the value of XMIN (see block 861). If XPOS is equal to or greater than XMIN, go to block 867. If XPOS is less than XMIN, go to block 868. |
| 865 | Reset bit position twenty three of FILE X(zero) to zero. |
| 866 | Compare XPOS and XMIN. |
| 867 | Load content of FILE X(ten) into the temporary register CYCLE. |
| 868 | Is bit position twenty three of FILE |

Table 11-continued
Supplementary Explanation of the Program Steps of FIG. 11

Figure 12:
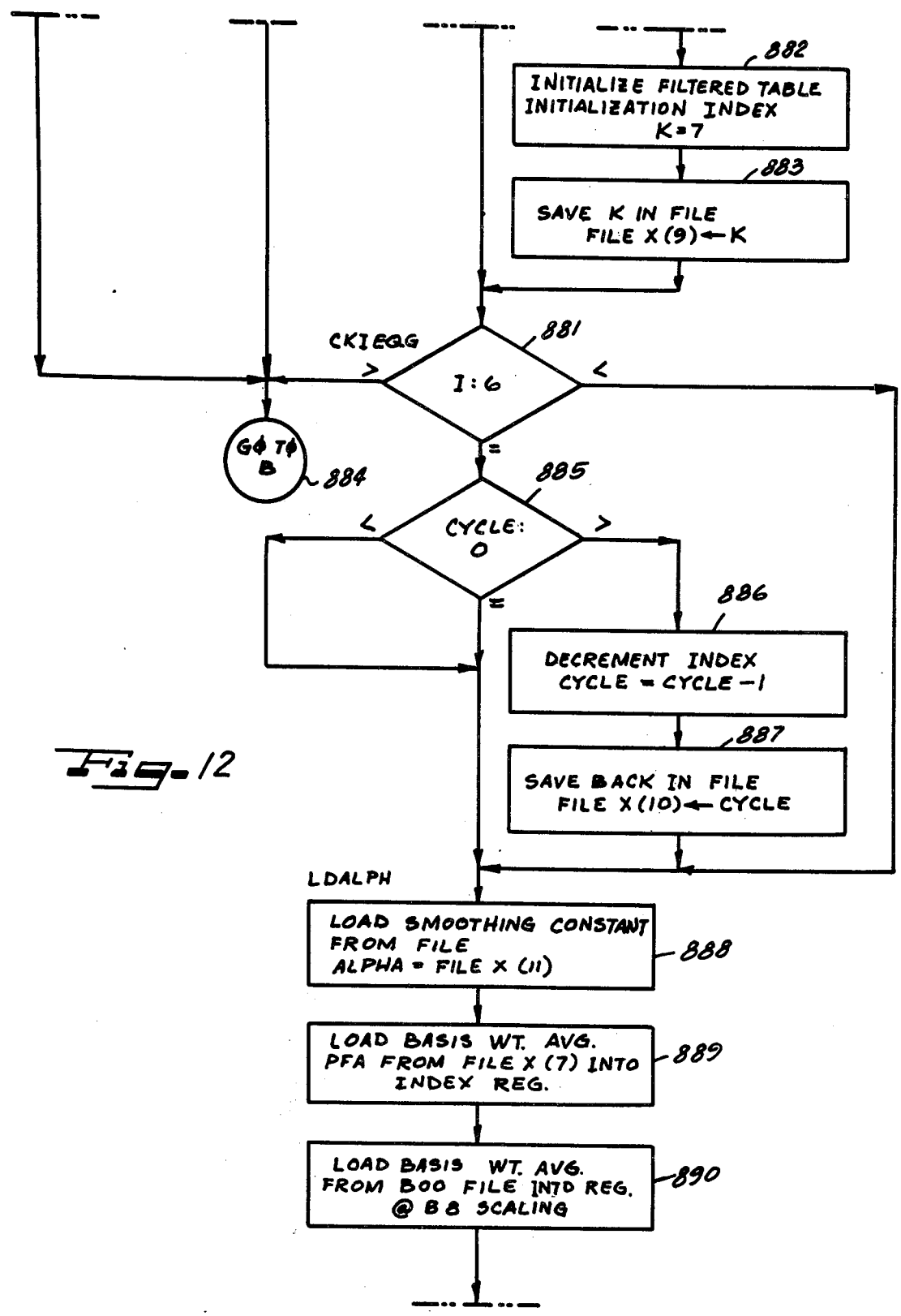

| Program Step | Comment |
|---|---|
| | X(zero set? If yes, go to comparison block 881, FIG. 12. If not, proceed with standardizaton beginning at block 870. |
| 869 | Set temporary register K to seven or a multiple of seven. |
| 870 | Set bit position twenty three of FILE X(zero) to the logical one state. |
| 871 | Put the value of K (see block 869) into FILE X(nine). |
| 872 | Set temporary register CYCLE to logical one state. |
| 873 | Place content of CYCLE in FILE X (ten). |
| 874 | Same as block 872. |
| 875 | Same as block 873. |

Table 12
Supplementary Explanation of the Program Steps of FIG. 12

| Program Step | Comment |
|---|---|
| 881 | Compare value in temporary register I with six. |
| 882 | Continuation from block 875, FIG. 11. Same comment as for block 869. |
| 883 | Same as block 871. |
| 884 | Go to BENTER location, FIG. 16, after an affirmative decision at block 844, FIG. 10; or after execution of step 873, FIG. 11; or if I is greater than six at block 881. |
| 885 | Compare CYCLE and zero. |
| 886 | Decrement CYCLE by one if CYCLE was greater than one at block 885. |
| 887 | Same as 873. |
| 888 | Load content of FILE X(eleven) into temporary register ALPHA. |
| 889 | Load content of FILE X(seven) into the index register (BOO File Address) |
| 890 | Load BOO process variable into A-register with fixed point scaling of B8. |

Figure 13:
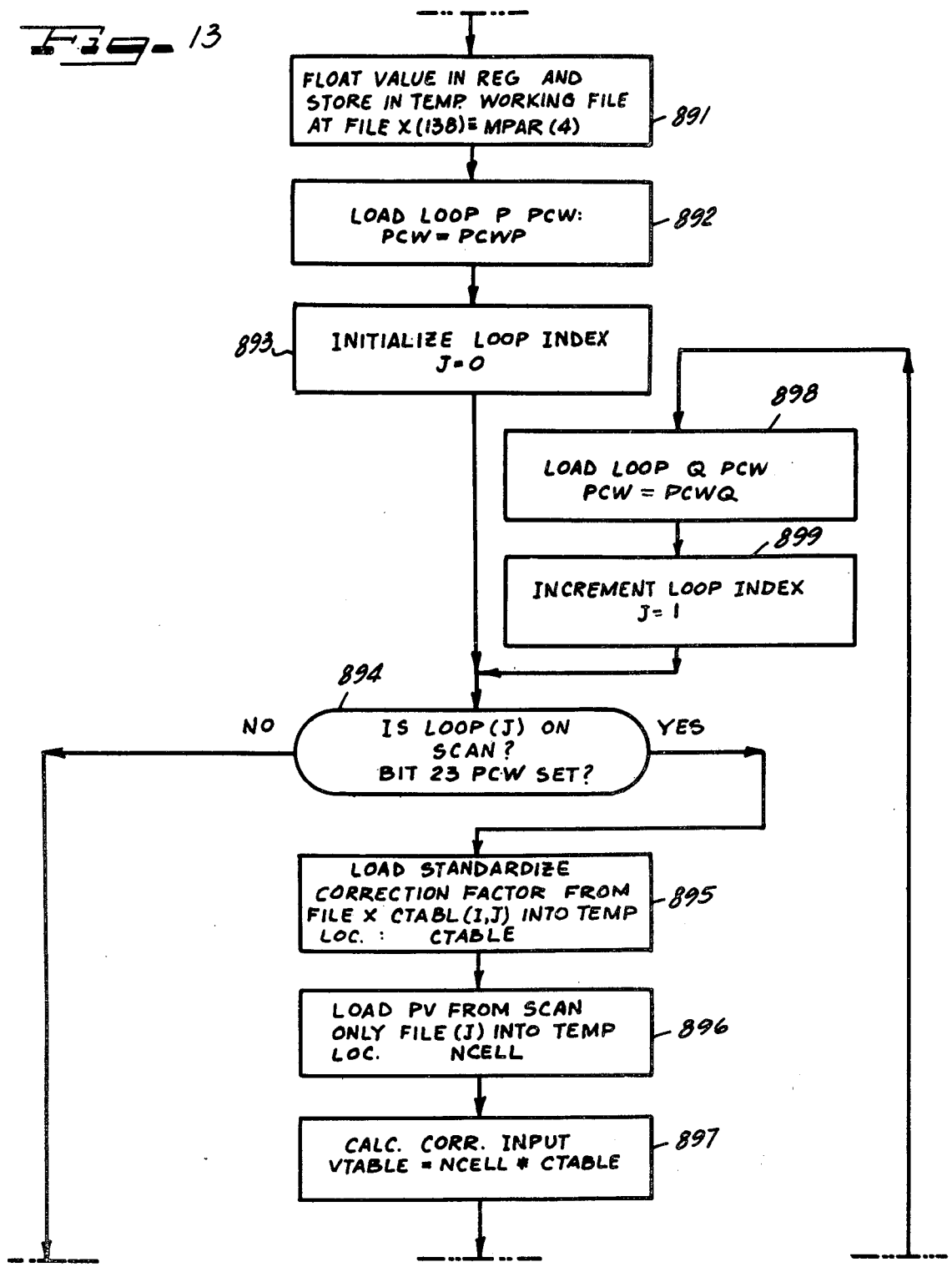

Table 13
Supplementary Explanation of the Program Steps of FIG. 13

| Program Step | Comment |
|---|---|
| 891 | Convert content of B8 SCALING (See block 890, FIG. 12) to floating point notation and store converted value in FILE X(one hundred thirty eight), which is also designated MPAR, location four in Table 7. |
| 892 | Load the process control word PCWP at the address given at FILE X(one) into the register PCW. |
| 893 | Set register J to zero. |
| 894 | Is bit position twenty three of the process control word (PCW) of LOOP (J) set? If not, go to block 910, FIG. 14. If yes, go to block 895. |
| 895 | Load the content of CTABL of FILE X for the location corresponding to the current values of I and J into temporary location CTABLE. |
| 896 | Load the process variable (PV) from the Scan Only File PF(J) into the temporary location NCELL. |
| 897 | Calculate the corrected input value by multiplying the content of NCELL by the content of CTABLE, and store in |

Table 13-continued
Supplementary Explanation of the Program Steps of FIG. 13

| Program Step | Comment |
|---|---|
| | the table VTABLE of FILE X(See Table 14) in the location corresponding to current values of I and J. Go to block 901, FIG. 14. |
| 898 | After a negative decision at block 910, FIG. 14, the loop P subroutine is initiated by loading the process control word PCWQ whose address is given at FILE X(two) into the temporary register PCW. |
| 899 | Increment the value stored in location J to one. |

Table 14
Supplementary Explanation of the Program Steps of FIG. 14

| Program Step | Comment |
|---|---|
| 901 | Compare the value in temporary location K with zero. If K is equal to or less than zero, go to block 902. If K is greater than zero, go to CHKSTZ, block 903. |
| 902 | Load content of current location of VTABL (I,J) from FILE X into the temporary location PFCELL. |
| 903 | Is bit twenty three of the status word in FILE X (zero) set |
| 904 | Transfer content of NCELL (see block 896, FIG. 13) into the temporary location PFCELL. |
| 905 | Apply the smoothing algorithm by calculating the sum of ALPHA times NCELL and (one minus ALPHA) times PFCELL, and store the result in NFCELL. |
| 906 | Transfer the content of NFCELL to the appropriate location of VTABL (I,J) in FILE X. (See Table 7.) |
| 907 | Load the PV from Scan Only LOOP J, i.e. Process FILE PF (J) into temporary register PV (J). |
| 908 | Store the content of PV (J) in table STTABL (I,J) of FILE X at a location corresponding to the current values of I and J. See Table 7. |
| 910 | Has loop Q been processed? If not, enter loop Q at block 898, FIG. 13. If the content of temporary location J is equal to one, go to block 911. |
| 911 | Compare the content of temporary location K with zero. If K is less than zero, go to the B entry location BENTER, FIG. 16. If K equals zero, go to block 921, FIG. 15. If K is greater than zero, go to block 912. |
| 912 | Decrement the count in K by one. |
| 913 | Store the content of K in FILE X(nine). Go to BENTER locaton in FIG. 16. |

Figure 15:
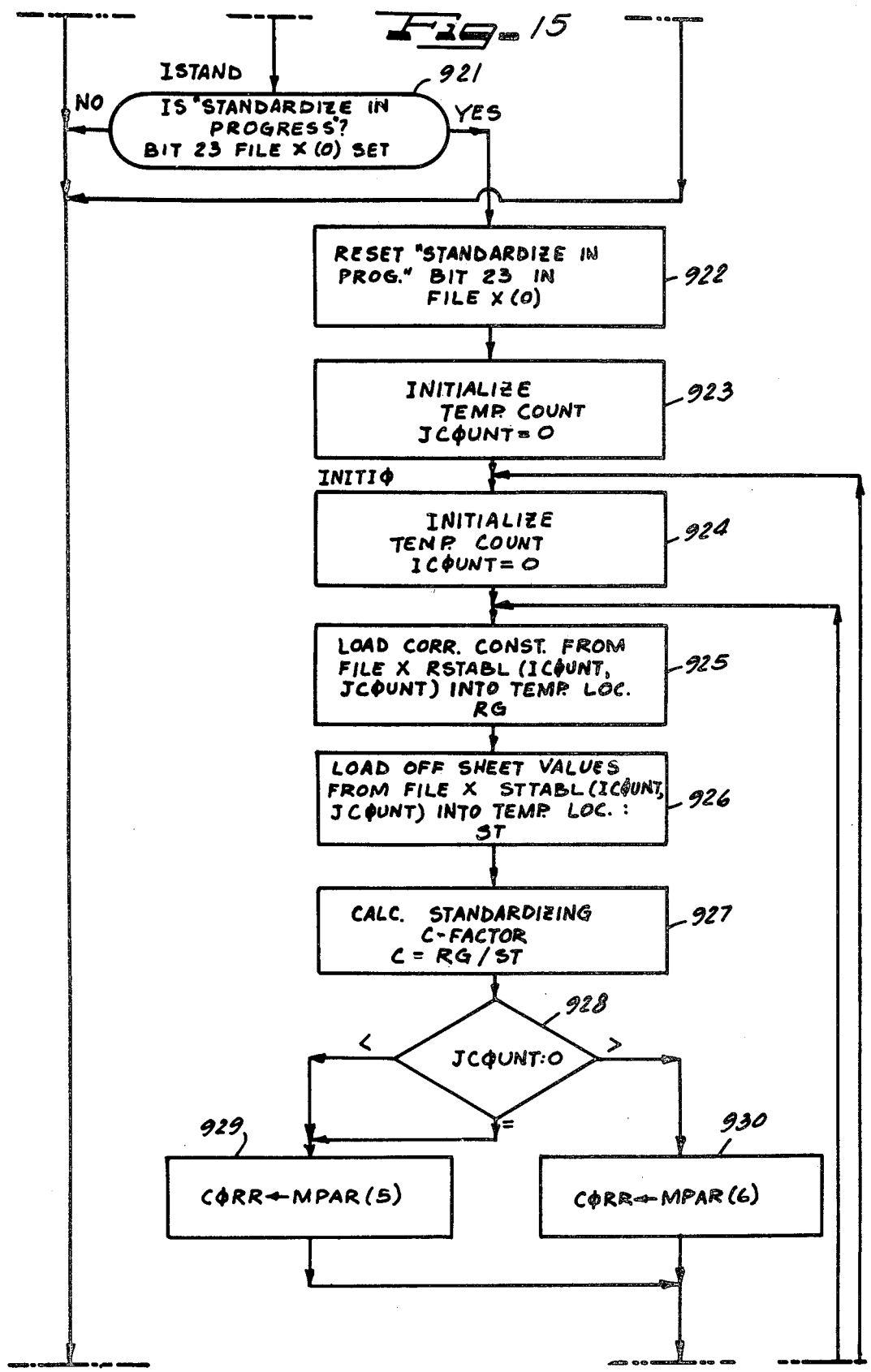

Table 15
Supplementary Explanation of the Program Steps of FIG. 15

Figure 16:
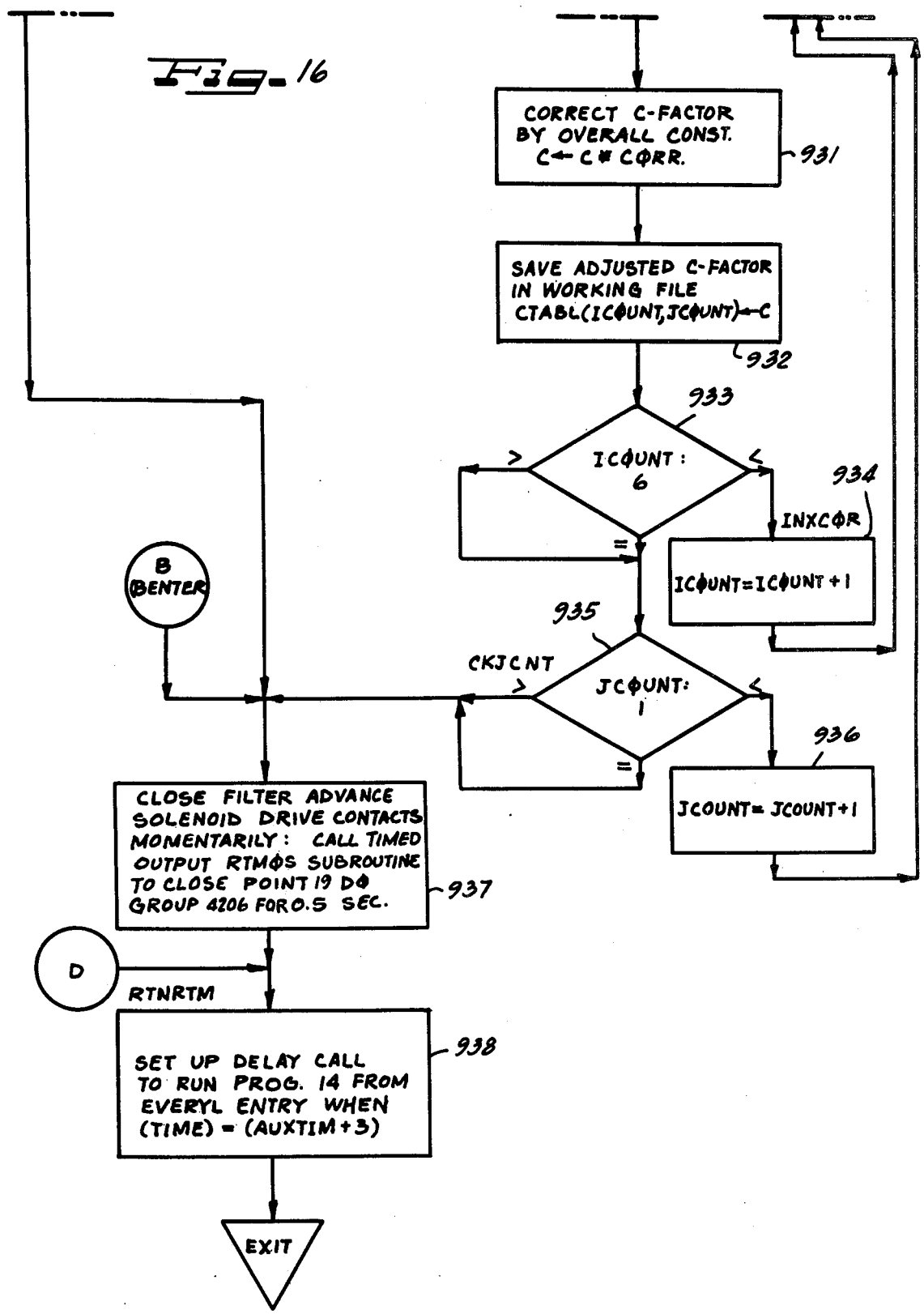

| Program Step | Comment |
|---|---|
| 921 | Is bit position twenty three of the STATUS word from FILE X(zero) set If not, go to BENTER location of FIG. 16. If affirmative, go to block 922. |
| 922 | Reset bit position twenty three of FILE X(zero). |
| 923 | Set temporary register J COUNT to zero. |

Table 15-continued

Supplementary Explanation of the Program Steps of FIG. 15

| Program Step | Comment |
| --- | --- |
| 924 | Set temporary register I COUNT to zero. |
| 925 | Load the correction constant from the appropriate location of RSTABL, Table 7, into the temporary location RG. |
| 926 | Load the standardization value from the appropriate location of STTABL, Table 7, into the temporary location ST. |
| 927 | Calculate the standardizing C factor by dividing RG by ST and store in temporary location C. |
| 928 | If J COUNT is less than or equal to zero, go to block 929; otherwise go to block 930. |
| 929 | Transfer the value stored at FILE X (one hundred thirty nine) to temporary location CORR. |
| 930 | Transfer the value stored at FILE X (one hundred forty) to temporary location CORR. |

Table 16

Supplementary Explanation of the Program Steps of FIG. 16

| Program Step | Comment |
| --- | --- |
| 931 | Multiply the value in temporary location C (see block 927) by the value in CORR and store the adjusted C factor in C. |
| 932 | Store value in C in FILE X at CTABL at current values of I COUNT and J COUNT. |
| 933 | Compare I COUNT to six. If I COUNT is less than six, go to block 934. |
| 934 | Increment I COUNT by one and reenter at block 925, FIG. 15. |
| 935 | Compare J COUNT and one. If less than one, go to block 936. |
| 936 | Increment J COUNT by one and reenter at block 924, FIG. 15. |
| 937 | The computer output contact at point nineteen of digital output (DO)Group forty two hundred and six (not shown) is closed by the computer in response to this program step to energize solenoid 240, FIGS. 3 and 6, from the plus 24 volt supply and conductors 505 and 506. |
| 938 | Program Fourteen reschedules itself to run again in approximately one second. |

Comments Regarding Program Fourteen

1. The values stored under RSTABL (118–133) will be identical to the values stored under RGTABL (44–59) and, therefore, the former table will be eliminated when the necessary program changes are also made. The RK and TK correction factor approach allows this simplification of the calculations.

2. Program Fourteen can be further revised to eliminate the need for the nominal diffusor transmittance, $T_d$, completely. Manipulation of the terms of the equations involved permits this elimination. Note referring to Table 4, S.0023, that TPDOTD, the ratio of TPD/TD, is equal to (TSP* TK)/TSD, eliminating the need to know the absolute value of TD. TD is the computer symbol representing $T_d$, the transmittance of the diffuser. Refer also to the paragraph following Table 2.

3. Program Fourteen also calls for the re-initialization of the algorithm which smooths the "raw" reflectance and transmittance after each standardization. It is presently considered that this re-initialization will not only be unnecessary, but would add to control problems. Consequently, this will likely be changed so that this smoothing goes on indefinitely after a run start-up (Note: Do not confuse the smoothing of the "raw" data from the paper with the correction factors acquired during standardization. The latter will not and likely should not be smoothed at all.)

4. Program Fourteen has not as yet been debugged. Debugging can only be accomplished after connecting the computer to the system of FIGS. 1-6 via an A to D converter. It is considered that such debugging is a routine matter well within the skill of the art. It may be noted that the OMOD is now on line as shown in FIGS. 1-6 and data collection has begun.

Summary of Operation of Program Fourteen

Program Fourteen is designed to perform various functions described as follows:

1. Sequentially read the reflectance and transmittance values stored in the Process File until both values for each of the seven OMOD filter positions are obtained.

It takes about two seconds from the time the filter wheel is advanced until the photocell readings reach a near equilibrium condition. Program Fourteen is, however, linked timewise to the DCC scan program and is programmed to run every second also. Consequently, any data acquired before the photocells reach a near equilibrium condition, will be liable to intolerable error. Program Fourteen solves this problem by processing data on a multisecond interval basis only, e.g., every 2, 3, 4, etc., seconds depending upon the choice of the value of the term SLOWDOWN which inserted in File X(five).

2. Check the OMOD to see if it is operating properly and issue alarms if it is not. "OMOD Filter Stuck" and "Skipped Filter" alarm messages were made available.

The upper OMOD head is designed with an extra reed switch 358, FIG. 6, which closes when the brightness filter is in the optical train pathway. (Previous description herein refers to the brightness filter as the first position; however, Program Fourteen refers to it as the zero position.) The computer program checks the status of this switch as being open or closed by means of Point 22-Group 1400. The filter index is initialized back to zero each time the status of Point 22-Group 1400 is closed. Discrepancies, should they occur between the expected filter index based on the incremented count and the actual filter position can be readily recognized by this program. This serves as the basis for the alarms previously mentioned.

3. Determine when and how often the optical property Data Reduction Program, No. Forty Two, (see FIGS. 17-20) is to be run. This is controlled by the value chosen for the term "CYCLE".

4. Read the OMOD head position and the average basis weight of the paper being produced and store for use in subsequent calculations or program logic tests. This information is readily available from a basis weight control program which has been in use for several years.

5. Correct the "raw" reflectance and transmittance data by multiplying each of the fourteen values by the appropriate correction factor. The values of these correction factors are updated by the last standardization sequence which occurred prior to their actual use (see 7 below).

6. Exponentially smooth each of the corrected reflectance and transmittance values and store for subsequent calculations.

Exponential smoothing requires a previous value to act upon; however, such previous value is not available for run startup, etc. An initialization technique involving an initialization index, k, is employed to solve this problem. The degree of smoothing is determined by the value chosen for $\alpha$ (ALPHA).

7. Initialize and control the automatic standardization of the OMOD.

The OMOD heads are mounted next to an Electronic Automation Inc. (EA) basis weight gauge in a piggyback fashion. This EA system utilizes an "O" frame to permit scanning the full web width. It is also designed to automatically retract the carriage upon which the basis weight gauge and OMOD are mounted, to an offsheet position at 1-hour intervals. Program Fourteen takes advantage of this schedule to standardize the OMOD at the same time that the basis weight gauge is being standardized. When offsheet, the very durable Lucalux backing 135, FIG. 3, is always in position to permit checks of its reflectance and transmittance. Due to its durability and inertness, the latter should remain unchanged for long periods of time. In addition, the moving web will insure its cleanliness prior to each stadardization occurrence. Consequently, this standardization procedure will allow for accurate updating of the correction factors for each filter position. In so doing, it compensates for any changes which may inadvertently occur in the light source, filters, photocells, lenses, electronic amplification, etc.

Two overall geometrical correction factors are also employed at this point of the program to adjust for any relative head spacing or alignment change that may also inadvertently occur. Experimental data has shown that the same geometrical correction can be used for each reflectance measurement. The values of these two factors are, however, not determined automatically, but must be determined by external means involving offline audit testing by comparing OMOD readings with those of off-line standard laboratory instruments before being fed into the proper computer storage. Initial values of these two factors will be unity; in which case, the relative head geometry will be assumed to be in standard condition and no geometrical correction factor required.

The alternative to using these geometrical correction factors is to realign and/or respace the heads when needed. In the case of minor adjustments, the former approach is clearly the more desirable where the heads are in an inaccessible location and functioning on a high-speed proper machine with little downtime available for such mechanical readjustments.

Program fourteen as presently devised, does not call for the exponential smoothing of the correction factors updated upon each standardization. This could be easily changed should on-line experience indicate that such smoothing is desirable.

8. Control the advance of the OMOD filter wheel 210, FIG. 4, to the next filter position at the desired time interval. This is accomplished by the computer 996, FIG. 6, directing the closure of a loop 505, 506, FIG. 6, which energizes the solenoid. The energized solenoid lifts the rachet arm 230, FIG. 3, clear of the lug against which it was previously braced. The filter wheel shaft is under a continuous torque, tending to rotate it at all times. Thus, it begins to rotate when freed of the holding ratchet arm; but it is stopped again at the next lug, since by then the solenoid attached to the ratchet arm is once again de-energized by computer command. The low torque motor 209, FIG. 6, designed to be stalled indefinitely without harm provides the necessary filter wheel torque.

9. Program fourteen reschedules itself to run again in approximately 1 second.

Optical Property Data Reduction Subroutine of FIGS. 17–20 (Program Forty Two)

The purpose of this program is to reduce the corrected reflectance and transmittance data into terms with which papermakers are familiar and upon which paper optical specifications are based; e.g., brightness, opacity, color and fluorescence. A description of this program follows.

The following Tables will serve to supplement the labels applied to the blocks of the flow chart illustrating this program.

Table 17

Figure 17:
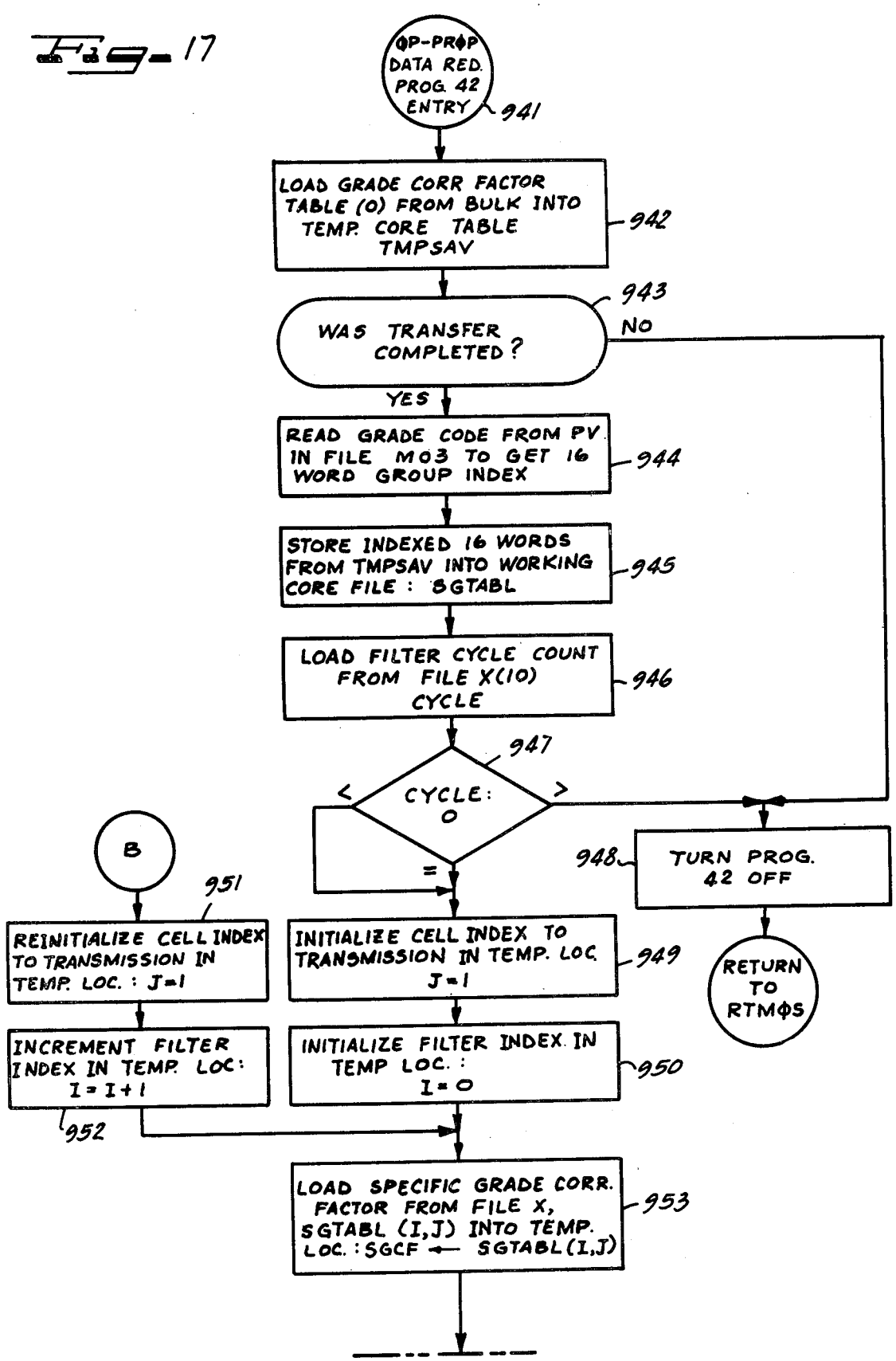

Supplementary Explanation of the Program Steps of FIG. 17

| Program Step | Comment |
|---|---|
| 941 | Entry to Program Forty Two |
| 942 | Load grade correction factor table from bulk storage into the temporary core storage table TMPSAV. |
| 943 | Was transfer to TMPSAV completed |
| 944 | Read the grade code from the process variable input file MO3 to obtain a sixteen word group index. |
| 945 | Transfer TMPSAV into the working core file SGTABL. |
| 946 | Load content of FILE X (ten) into CYCLE. This register is decremented during operation of Program Fourteen. |
| 947 | Compare CYCLE and zero. |
| 948 | If cycle is greater than zero, turn Program Forty Two off and return to RTMOS. |
| 949 | Set location J to one. |
| 950 | Set location I to zero. |
| 951 | On entry at B, set location J to one. |
| 952 | Increment the value in location I by one. |
| 953 | Load value from SGTABL of FILE X (See Table 7) for current values of I and J into SGCF. |

Table 18

Figure 18:
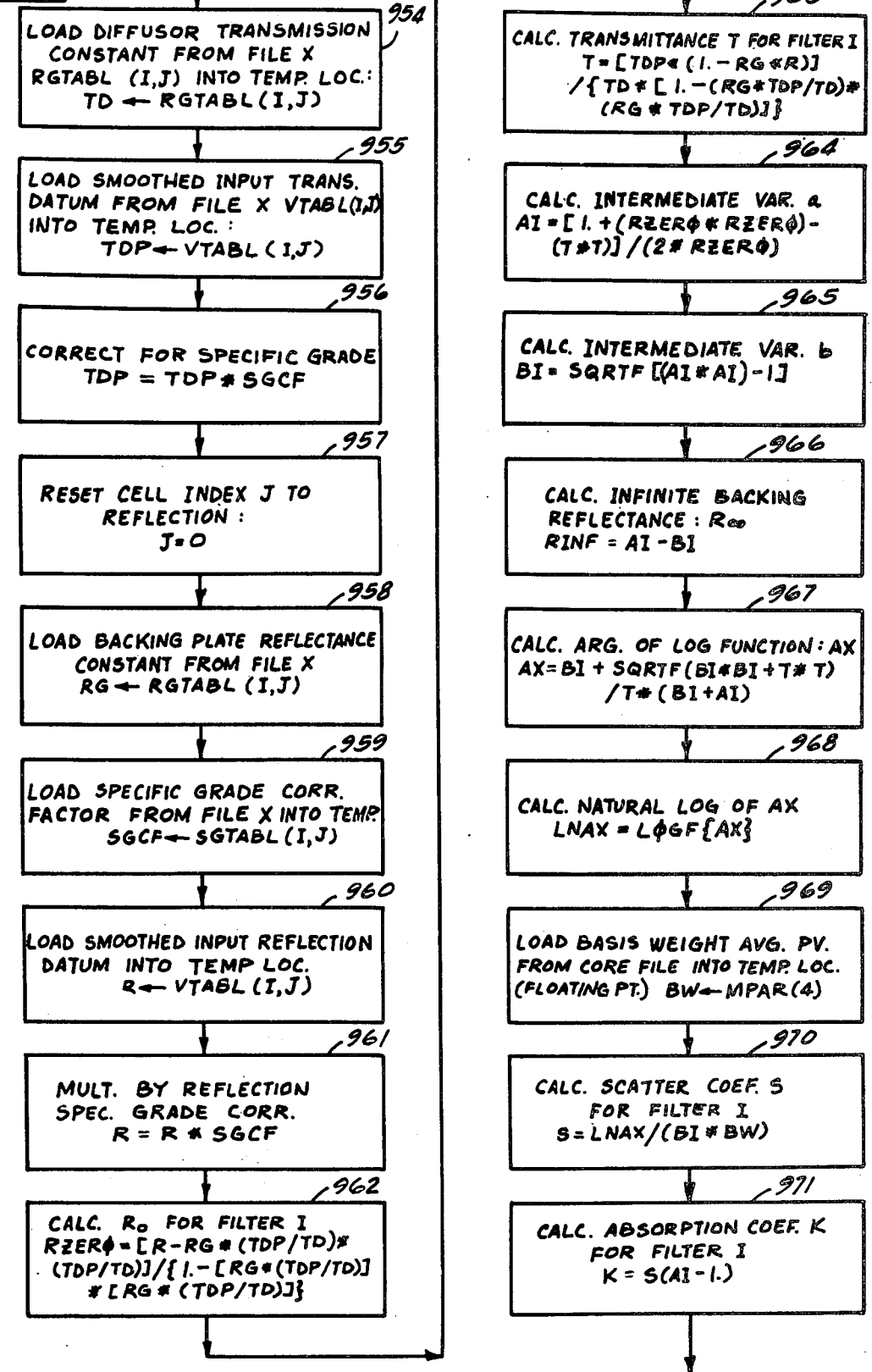

Supplementary Explanation of the Program Steps of FIG. 18

| Program Step | Comment |
|---|---|
| 954 | Load pertinent value from RGTABL into TD. |
| 955 | Load indexed content of VTABL into TDP. |
| 956 | Multiply by SGCF (See block 953, FIG. 17). |
| 957 | Set J to zero. |
| 958 | Load indexed value from RGTABL of FILE X into RG. |
| 959 | load desired value from SGTABL of FILE X into SGCF. |

Table 18-continued
Supplementary Explanation of the Program Steps of FIG. 18

| Program Step | Comment |
|---|---|
| 960 | Load indexed value from VTABL of FILE X into R. |
| 961 | Multiply R and SGCF and store product in R. |
| 962 | Calculate $R_o$ using the equation given in Table 6 in conventional form. |
| 963 | Calculate transmittance T using the equation of Table 6. |
| 964 | Calculate the value A/2 where A is given in Table 6. |
| 965 | See the equation for $R_{oo}$ in Table 6. |
| 966 | See the equation for $R_{oo}$ in Table 6. |
| 967–970 | The scattering coefficient S is also calculated using Kubelka-Munk Theory on the basis of the equation: $$S = \frac{1}{b \times \text{Basis Weight}} \times [\text{Arc Sinh}(b/T) - \text{Arc Sinh } b]$$ where $b = \sqrt{a^2 - 1}$ and $a = (1 + R_o^2 - T^2) / 2 R_o$ |
| 971 | The absorption coefficient K is found from the equation: $K = S(a - 1)$. |

Figure 19:
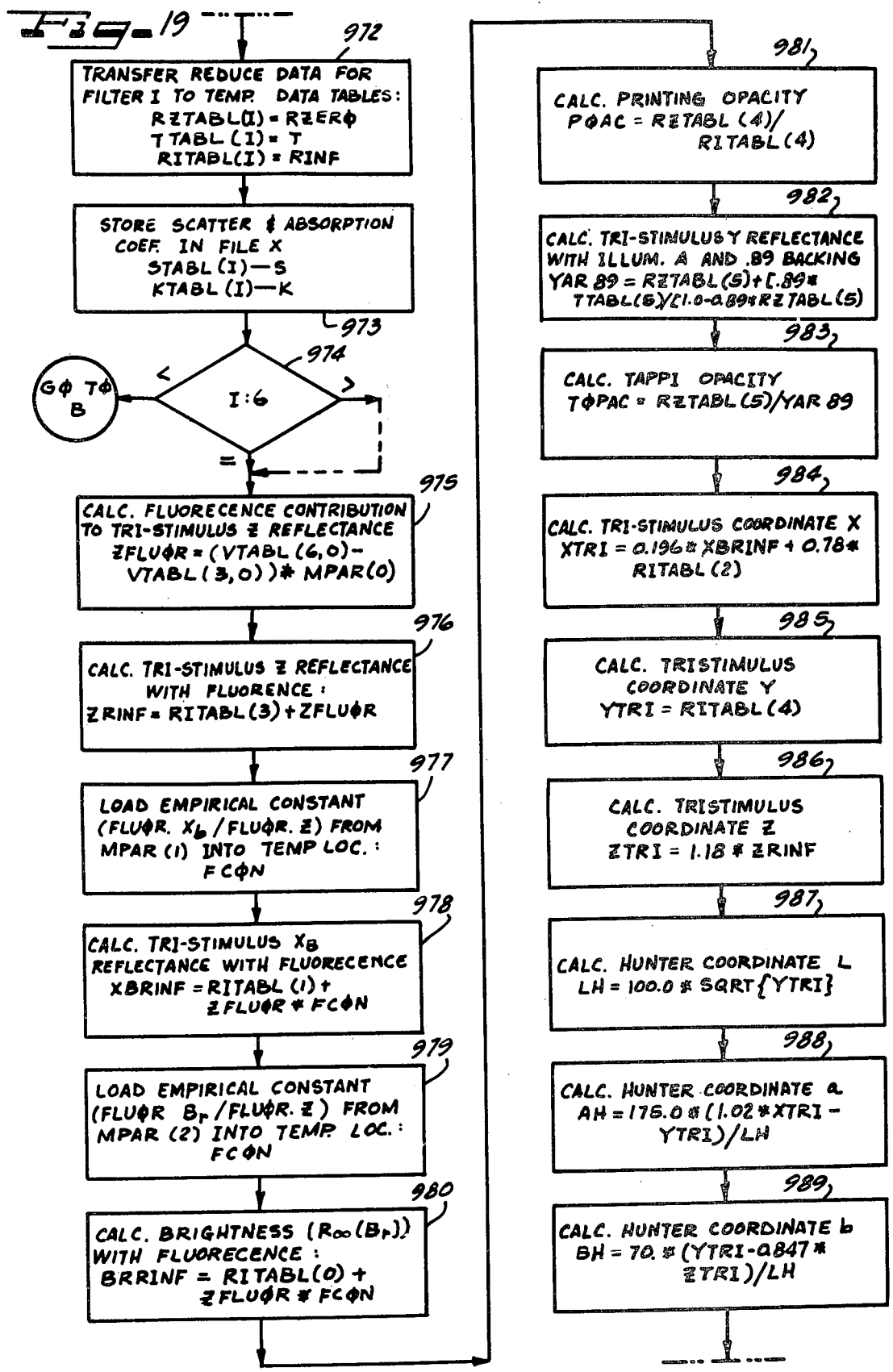

Table 19
Supplementary Explanation of the Program Steps of FIG. 19

| Program Step | Comment |
|---|---|
| 972 | Transfer the calculated data to the temporary data tables at the locations corresponding to the current value of I. |
| 973 | Store calculated scattering coefficient S and absorption coefficient K in FILE X. |
| 974 | Go to entry B at block 951, FIG. 17, to repeat the calculations for the other filter wheel positions if I is less than six. |
| 975 | See the calculation of $F_Z$ in the section of this specification entitled "Structure and Operation of a Prototype Optical Monitoring Device". |
| 976 | Calculate $R_{oo}$ including fluorescense contribution and store at ZRINF. |
| 977–978 | For example $F_{X(Blue)}$ may equal 1.204 $F_Z$ where $F_Z$ is found at step 975, and $R_{oo}(X_{Blue})$ plus $F_X$ (Blue) gives the desired value for BRINF. |
| 979–980 | For example $F_{Brightness}$ may equal 0.864 $F_Z$. Thus $R_{oo}$ (Brightness with fluorescense) plus $F_{Brightness}$ and this sum is stored at BRRINF. |
| 981 | Printing opacity R.89 is calculated by dividing $R_o$ by $R_{oo}$ (both from Yc filter wheel position). |
| 982–983 | For TAPPI opacity, obtain the ratio of $R_o$ to R.89 using the $Y_A$ filter wheel position. |
| 984 | The C.I.E. X tristimulus value is calculated as follows: $X = 0.196 R_{oo}(X_{Blue}) + .78 R_{oo}(X \text{ Red})$ |
| 985 | C.I.E. tristimulus value $Y = R_{oo}(Y_c)$ |
| 986 | C.I.E. tristimulus value $Z = 1.18 R_{oo}(Z)$ |
| 987 | Compare block 985. |
| 988 | See blocks 984, 985 and 987. |
| 989 | See blocks 985, 986 and 987. |

Table 20
Supplementary Explanation of the Program Steps of FIG. 20

| Program Step | Comment |
|---|---|
| 990 | See Table 7 for a showing of OUTABL. The data in OUTABL is available for print out in demand. |
| 991 | The reset value at FILE X (one hundred thirty seven) is placed at FILE X (ten). See Table 7. |
| 992 | Save File X in the permanent core table beginning at location 63200. |
| 993 | Turn Program Forty Two off and return to RTMOS. |

Comments Regarding Program Forty-Two

1. Although not indicated as yet, the output of the fluorescent contribution to TAPPI brightness will be part of the computer output when the programs are finalized.

2. Program Forty-Two has been checked out against a currently operating program used on a research Hewlett-Packard computer and both give the same results.

3. It is planned to study means of determining and using the Specific Grade Correction Factor other than that described in Program Forty-Two. It may be decided to apply such correction directly to $R_{oo}$ rather than to the smoothed values of $T_{pd}$ and $R_g$. The transmittance of the paper, T, may not need any Specific Grade Correction and could then be used along with the corrected $R_{oo}$ to compute the scattering and absorption coefficients s and k. The latter will be very useful and may represent preferred parameters for closed loop control.

Summary of Operation of Program Forty-Two

The purpose of this program is to reduce the corrected reflectance and transmittance data into terms with which papermakers are familiar and upon which paper optical specifications are based; e.g., brightness, opacity, color and fluorescence. A description of this program follows.

1. The data reduction steps of this program are performed only if the term "CYCLE" which is decremented in Program Fourteen, is zero or negative. Otherwise, this data reduction routine is by-passed completely.

2. The exponentially smoothed reflectance and transmittance data acquired by Program Fourteen are first corrected by multiplying each of the fourteen values by an appropriate Specific Grade Correction Factor (SGCF). With a few exceptions, the SGCF'S provide only small corrections, if any at all. The SGCF'S serve two purposes.
   a. They compensate for the small errors resulting from the use of the Kubelka-Munk or energy balance equations when the latter do not apply exactly.
   b. They allow the reduced data values to precisely correspond to any one of several possible off-line instruments. Existing off-line instruments do not agree among themselves. Thus, the choice of the off-line instrument for performing the audit testing will affect the values of the SGCF'S.

3. The next part of Program Forty-Two computes and stores the values of $R_o$, T, $R_{oo}$, S and K of the paper being measured for each of the first six of the seven OMOD filter positions. Kubelka-Munk and IPC derived energy balance equations are used for this purpose. Note that prior to these calculations, the reflectance values are those of the single ply of paper when backed by the Lucalux and were symbolized by $R_g$. Similarly, the former transmittance values were those of the single ply of paper in series with the Lucalux, now serving as a diffusing window. This was symbolized by $T_{pd}$.

The phenomenon of fluorescence is not accounted for by Kubelka-Munk theory. For this reason the OMOD optical geometry was chosen to exclude fluorescence by eliminating ultra violet (U.V.) light from the incident light beam of the first six filter positions. For reasons explained later, the seventh filter position permits the reflectance of the Z function with ultra violet energy present in the incident beam.

4. The degree of fluorescence as measured by the "Fluorescent Contribution" is determined next. Fluorescence occurs as a result of excitation of special dyes (optical brightness or fluorescent dyes) by ultra violet energy contained within the incident light beam(s). The "Fluorescent Contribution" is defined here to be the increase of the reflected light flux that occurs as a result of the existence of some standard quantity of ultra violet energy in the incident light beam.

Such U.V. energy is rapidly absorbed by the outer layers of most conventional papers. Consequently, fluorescence is primarily a characteristic of the surface of the paper being viewed. Thus, for practical purposes, the value of $[R_g$ (with fluor.)$-R_g$ (without fluor.)$]=[R_{oo}$ (with fluor.)$-R_{oo}$ (without fluor.)$]$ when the same incident light beam containing the same U.V. energy is used in both cases. The right side of this equation is by the definition above, the Fluorescent Contribution provided the standard quantity of U.V. light is employed in the incident beam. The left side of this equation is a quantity measureable on a single ply of the moving paper web. In the case of the OMOD a measure of the fluorescent contribution to the Z function reflectance is obtained from the term, $[R_g$ (Filter No. 7)- $R_g$ (Filter No. 4)]. The filter arrangement existing in the No. 7 OMOD filter position permits about twice the standard quantity of U.V. energy to strike the paper. (The U.V. energy in the incident beam of the Standard TAPPI Brightness Tester is considered to be the standard quantity here.) This increases the sensitivity of this measurement by two-fold. It also necessitates the use of a proportionality constant of approximately one-half to compute the value of the standard Fluorescent Contribution to the Z function reflectance.

The Fluorescent Contribution to the reflectance of the $X_B$ and Brightness functions can be computed directly from the Z function Fluorescent Contribution. The multiplication factors involved are constant for a given optical brightner and need to be changed only if the type of optical brightner is changed. The Fluorescent Contributor to the $Y_C$, $Y_A$ and $X_R$ functions can be ignored as being inconsequential for the typical optical brightner used in the paper industry today.

5. Defining equations are used to compute and store for accessible putout values of the following:
 a. Standard TAPPI Brightness
 b. Printing opacity based on illuminant C
 c. $R_{89}$ based on illuminant A
 d. TAPPI opacity based on illuminant A
 e. X Tristimulus value
 f. Y Tristimulus value
 g. Z Tristimulus value
 h. Hunter Coordinate, L
 i. Hunter Coordinate, a
 j. Hunter Coordinate, b
 k. Fluorescent Contribution to TAPPI Brightness Excerpts from a Paper Relating to the Present Invention The following are excerpts from a draft of a paper prepared for the American Paper Institute, which paper is dated January 10, 1974 and is believed to have been distributed in printed form to members of the American Paper Institute in February 1974. The draft was prepared by an author who is a joint contributor to the improvements described and claimed herein. The final paper in printed form was included as part of our application U.S. Ser. No. 438,993 as filed, and is incorporated herein by reference except as included in the following excerpts. The incorporated paper is identified as "REPORT NO. 58, TO: American Paper Institute Instrumentation Program", "SUBJECT: An Analysis of On-Machine Optical Instrumentation", DATE: Jan. 10, 1974" and is submitted by the Institute of Paper Chemistry, Appleton, Wisconsin.

The Institute of Paper Chemistry was retained to evaluate an early conception of an on-the-paper-machine optical monitoring device for simultaneous measurement of reflected and transmitted light, and to assist in the optimum implementation of such conception. Accordingly, a substantial portion of the work reported in the following excerpts appears to inure as part of the original conception.

The following discussion is presented as constituting a description bearing on the background of the joint invention and as clarifying and amplifying on the nature of such invention, even through the paper may also include subject matter which is based on work entirely independent of the project sponsored by the assignee of the present invention. Further, the paper will indicate the range of equivalents to the illustrated embodiment with respect to matters such as spectrum and geometry of illumination.

Summary

Various aspects of the on-machine measurement of the optical properties of paper for the control of opacity, standard brightness, and color have been examined. Whereas many optical property specifications are based on reflectances determined on opaque pads of paper, on-machine measurements are limited to the various optical values which can be determined on single thicknesses of a moving web. Thus, one must either control to the optical property which can be measured on-machine or strive to develop reliable correlations between the on-machine and off-machine measurements. The latter approach is more desirable. For this purpose, it is advantageous to adopt the design features of the off-machine testing apparatus to the fullest extent possible for on-machine use. Fortunately, the important factors in optical instrument design related to spectral characteristics, geometry, and photometric linearity can be translated to on-machine use with considerable exactness.

A large number of different approaches are possible in the measurement of optical properties of single sheets for purposes of control. Of these, however, distinctions can be made between single measurements, of reflectance, for example, and the measurement of two optical parameters for the same sampled area. The latter approach permits calculation of thick pad reflectivity values using appropriate theory with an essential independence of basis weight, whereas single reflectance data are functions of basis weight requiring empirical compensation. Although various possible pairs of optical measurements can be made on the same specimen area, among the most satisfactory for the use of theory are reflectance with black body backing and transmittance. The Kubelka-Munk theory, though not rigorously applicable in practice, has been shown to be rather successful in predicting thick pad reflectivity from such data in laboratory tests for white papers of reasonable homogeneity. It is less successful for deeply colored papers and for sheets of very low basis weight.

The sensitivity of spacing of white backings from paper specimens was measured with respect to the color of various commercial papers. At a central spacing of 0.32 inches, it was determined that a variation in spacing of about 0.020 inches is possible for most papers without noticeable color difference.

Optical measurements would be made on-machine on webs of varying moisture content and at elevated temperatures compared to a controlled laboratory testing environment. An experimental study of the effect of changing moisture content (R.H. range of 5 to 84%) on color showed small effects for most white papers, which were attributed to differences in surface structure. Somewhat larger effects were noted using directional illumination compared to diffuse illumination. The largest effects, for some colored papers, were attributed to changing spectral absorption characteristics of the dyestuff. Sheet moisture content effects on optical properties were judged to be within tolerable limits over a range corresponding to relative humidities between 5 and 50%.

The effect of temperature on the color of various commercial papers was studied over a range of 23° to 62° C. Important effects were found only for two colored papers. It was noted that significant elevations of specimen surface temperature can occur in optical apparatus employing high-intensity illumination.

Most other variables involving paper properties, machine operation, and mill environmental conditions are unlikely to be eliminated through instrument design or through the development of appropriate compensating factors. For these remaining factors, empirical correlations would be required to establish agreement between optical data or obtained on and off machine.

Introduction

Specifications for the various optical properties of paper are presently based on measurements made with laboratory instruments. Considerable standardization of optical instrumentation and testing methods have been developed, but new instruments and analytical methods are often introduced to the industry as well. Changes are welcome when they provide advantages in such areas as the utility of the measurement, improved accuracy, better agreement between laboratories, and in overall testing costs. The well-established advantages of industry-wide standardization in the measurement of the optical properties, however, must always receive serious consideration.

In recent years, the control of paper quality on the paper machine has grown in importance and, for optical properties, on-line control is a very practical objective.

Good control strategy requires that the properties of the sheet be determined rapidly on the moving web, but it is usually not possible to duplicate laboratory instrumentation for on-machine use. Whereas on-machine measurements are limited to such data as can be acquired on a single thickness of paper, optical properties such as brightness and color are determined on multiple thicknesses. Too often, optical instrumentation is developed for on-machine use with emphasis on the control function, but without serious consideration given to the further problem of conforming to off-machine optical property standards. The implied assumption is that a good reliable correlation will exist between the on-machine and off-machine optical measurements. Perhaps the most logical approach to the development of on-machine optical instrumentation is to design for maximum conformance with laboratory instrumentation in such factors as instrument geometry and spectral characteristics, to employ existing theory as far as possible to inter-relate single-sheet versus multiple-sheet optical measurements and to employ empirical correlations to the minimum extent required.

As on-machine optical instrumentation becomes more widely adopted, the advantages of continuously monitoring the optical properties of paper in real-time compared to the intermittent and few data which can be acquired by off-macine testing could lead to the use of specifications in the buying and selling of paper which are based on the on-machine instrumentation. Should this ever occur, it is particularly desirable that such on-machine specifications bear the highest possible degree of correlation with the off-machine specifications in current use.

In this report, many of the factors involved in the optical characterization of a moving web in a paper machine environment are discussed relative to the off-machine properties of brightness, color and opacity Optical Property Measurement and Specification
Brightness Papermaker's brightness, sometimes called G.E. brightness and now "standard brightness" was first established in the early 1930's as the particular reflectivity ($R_{oo}$) of paper determined with an instrument having a specified spectral response, specified geometry, and good photometric accuracy (1). At the same time, a system of calibration was developed whereby opal glass and paper standards are furnished periodically for each instrument.

In the early days, the scale was based on "smoked" magnesium oxide but, because of difficulty in arriving at a reproducible reflecting surface, a technique for measuring the absolute reflectance of magnesium oxide was developed (2). Thus, a total system (3) was made available so that this particular refectivity could be measured industry-wide with an accuracy of about ±0.3 reflectivity units. TAPPI standards T217 and T452 give the detailed specifications for the measurement of standard brightness for pulp and for paper and paperboard respectively. The following specifications are involved.

Spectral Response

The effective wavelength of an instrument for the measurement of standard brightness is 457 nm. Although the effective wavelength is the most important parameter describing the spectral response, wavelength bandwidth and shape of the function also influence the result and are specified. The standardized overall spectral response of the brightness instrument which includes the spectral power distribution of the light source, the spectral transmittance of the glass lenses and filters, and the spectral response of the phototube is given in Table I.

Table I

Spectral Response of an Instrument for the Measurement of Standard Brightness

| Wavelength, nm | Spectral Response Arbitrary Units |
|---|---|
| 400 | 1.0 |
| 405 | 2.9 |
| 410 | 6.7 |
| 415 | 12.1 |
| 420 | 18.2 |
| 425 | 25.8 |
| 430 | 34.5 |
| 435 | 44.9 |
| 440 | 57.6 |
| 445 | 70.0 |
| 450 | 82.5 |
| 455 | 94.1 |
| 460 | 100.0 |
| 465 | 99.3 |
| 470 | 88.7 |
| 475 | 72.5 |
| 480 | 53.1 |
| 485 | 34.0 |
| 490 | 20.3 |
| 495 | 11.1 |
| 500 | 5.6 |
| 505 | 2.2 |
| 510 | 0.3 |

The prescribed spectral response precludes use of a spectrophotometer employing a narrow bandwidth at 457 nm for the accurate measurement of standard brightness.

The spectral response function was chosen in the blue region of the spectrum for maximum sensitivity to changes in bleaching and the fading of paper with time. Once specified, however, the spectral response of different instruments must be maintained to close tolerances for reproducibility in measurement on an industry-wide basis.

When papers exhibit fluorescence, whether naturally or because of the addition of fluorescent dyes, the spectral power distribution of the light incident on the specimen must be specified. For standard brightness, the specified power distribution of the light incident on the specimen is given in Table II. Thus, adherence to the spectral specifications of Tables I and II permits the accurate determination of standard brightness of fluorescent as well as nonfluorescent papers.

Table II

| Wavelengths, nm | Spectral Power Distribution of the Light Incident on the Specimen Arbitrary Units |
|---|---|
| 320 | 0.0 |
| 330 | 0.7 |
| 340 | 9.7 |
| 360 | 9.7 |
| 380 | 17.1 |
| 400 | 26.0 |
| 420 | 37.2 |
| 440 | 50.3 |
| 460 | 64.1 |
| 480 | 80.0 |
| 500 | 100.0 |

In addition, the spectral transmittance of the filters and the phototube response are selected such that the instrument has negligible response to near-infrared radiant energy whether reflected from the specimen or as a result of speciment infrared fluorescence (4). It is important to note that some colored glass filters with essentially no transmittance in the red region of the spectrum will transmit substantially in the near infrared.

Geometry

The geometry employed for the measurement of brightness is illumination at 45° and normal viewing with the incident and reflected beam cone half-angles specified at 11.5° and 22.5° respectively. The angles of illumination and viewing are critical as paper surfaces are not ideal diffusers, and the numerical values obtained are a function of the particular geometry employed. Paper surfaces also exhibit directional effects. The light reflected when the specimen is illuminated in the "machine direction" is generally less than if the specimen is illuminated in the "across-machine direction". The brightness measurement is usually performed with the specimen illuminated in the "machine direction" and on the felt or top side. A sufficient number of sheets are required to form an opaque pad.

In the more translucent papers, an appreciable penetration of light into the sample occurs. As a result of internal light scattering, the illuminated area may differ significantly from the area of reflectance or light emergence. When this condition exists, the relative dimensions of the areas illuminated and viewed, the distribution of light on the illuminated spot, the alignment of the illuminated and viewed areas and their shapes can influence the result. In the instrument employed for the brightness measurement, the viewed area and the size and position of the illuminated spot are adjusted to prescribed standards. Conformance with the standard is ensured through use of the calibration standards. Properly adjusted, the instrument can be used to measure standard brightness of strongly translucent as well as opaque material.

Photometry

The photometric accuracy of an instrument for the measurement of brightness should be better than 0.1 point on a 0–100 scale (5). The overall error introduced through discrepancies in spectral response, geometry and the base of standardization must total less than 0.3 point.

Tappi Opacity

Opacity has long been defined in the paper industry as 100 times the ratio of the diffuse reflectance of a single sheet backed with a black body to its diffuse reflectance backed by a white body having an effective absolute reflectance of 0.89. An instrument designed and built in the early 1930's and has formed the basis of a system for determining TAPPI Opacity (6).

Spectral Response

The overall spectral response of the instrument including the spectral power distribution of the light source, spectral transmittance of the glass lenses and filter, spectral reflectivity of the integrating cavity lining and spectral response of the photocell is that the $E_a\bar{y}$ function (visibility function, Illuminant A) of the CIE system (7). The effective wavelength is 572 nm and the function extends over the entire visible spectrum. The specified broad-band spectral function makes the use of narrow-band instruments inappropriate for the measurement of opacity even though the effective wavelength is proper.

Fluorescent dyes, known in industry as optical brighteners, have a rather small, if not negligible, influence on opacity as the spectral response of the instrument in the usual fluorescent region (blue) of the spectrum is quite low. Also, the fluorescent radiation from a single sheet probably would not be too different when backed by a black or white body.

The spectral reflectivity of the integrating cavity lining does influence the overall spectral response of the instrument (3) and, because it is difficult to maintain a constant lining reflectance, a system for checking and maintaining the lining reflectance is essential to good accuracy.

Geometry

The geometry employed for the measurement of opacity is illumination at 20° and diffuse viewing. The photodetector receives light that is both diffusely and specularly reflected from the specimen and, because there is no baffle, the photodetector also views the light directly reflected from the specimen. The ratio of diffusely to directly reflected light depends upon the level of reflectance of the integrating cavity lining (physical dimensions also are influencing factors but remain constant) and, as this ratio changes, significant changes in measured opacity can occur (8).

The illuminated area is about 10 mm in diameter with a specimen aperture of about 14.3 mm in diameter. If translucent papers or standards are to be evaluated or used, the ratio of the viewed to the illuminated area is important (8). The state of focus and alignment of the optical system particularly influences the values obtained for translucent materials.

Stray light caused by a dirty or misaligned optical system can be a source of error. The optical system should be cleaned and aligned such that the difference in scale reading with the black body over the specimen opening when the light is blocked off before entering the cavity and with the light passing through the cavity into the black body should not be over 0.5 (0–100 scale). The reflectance of the black body should not be more than about 0.1%. The instrument scale is adjusted to read zero when the stray light is included.

Photometry

The photometric accuracy of different original instruments, employing a photocell-galvanometer system, varied from near perfect linearity to deviations as much as several points, depending upon the components. More recently, with the addition of solid state amplifiers and digital readouts, the photometric accuracy can be better than 0.1 (0–100 scale).

Calibration Standardization

In the measurement of the ratio $R_o/R_{0.89}$, it is necessary that the white body have an effective reflectance of 0.89. The instrument is equipped with a rotatable tube, one end of which contains a black cavity and the other the white body. A sheet of paper is placed over the specimen opening and, alternately, the black and white bodies are brought into position. The usual white body consists of a plug of appropriately surfaced magnesium carbonate within a protective glass cover. Changing the spacing between the surface of the magnesium carbonate and the specimen permits adjustment of the effective reflectance of the white body. There are two generally accepted means for arriving at the proper white body effective reflectance. One is to employ properly calibrated opal glass standards. While convenient, unless the instrument is properly adjusted with respect to translucency effects, substantial error can result. As constucted originally, the specimen supporting surface often departed from the intended plane. Thus, while the paper could follow a particular contour, the rigid glass standards will not, resulting in further error. After correcting these potential defects, it is possible to use opal glass standards and take advantage of their great convenience.

A second more basic method consists of determining $R_o$ and $R_{oo}$ for a particular paper specimen on the absolute scale and, through use of the relationship sometimes known as the "balance of energy" equation (9) or the Kubekla-Munk theory (10, 11, 12), to calculate $R_{0.89}$ for that specimen. The white body can then be adjusted so that this value is obtained instrumentally. Care should be exercised so that all reflectances are obtained on an identical area of the specimen. Charts are available (13) relating the reflectances $R_o$, $R_{oo}$ and $R_{0.89}$ or an appropriately programmed computer can be used to calculate the $R_{0.89}$ value.

Paper opacity standards calibrated for use with the opacimeter are now also available. These are convenient to use and will eliminate some of the difficulties associated with the opal glass calibration standards.

Magnesium oxide powder with an assigned absolute reflectance value is also available for use in calibrating the opacimeter for the measurement of reflectance on the absolute scale.

Printing Opacity

While the choice of spectral response for the measurement of opacity was excellent, the choice of the ratio $R_o/R_{0.89}$ as opposed to $R_o/R_{oo}$ was not. Printing opacity ($R_o/R_{oo}$) more nearly relates to the end use of the product and would eliminate the problem of adjusting the white body (14). The fact that a single sheet is required for the measurement of TAPPI Opacity whereas an opaque pad is required for printing opacity appears to be a factor in the reluctance of the industry to change. It is more convenient to determine the opacity of the single sheet using the white body.

COLOR

Spectrophotometers and filter colorimeters are the two main classes of instruments employed in the measurement of color. The spectrophotometer provides basic reflectivity information as a function of wavelength over the entire visible spectrum. The reflectivity ($R_{oo}$), obtained on the thick pads of paper, with the values based on the absolute scale is basic to color measurement. The reflectivity curve contains the essential information regarding the color of the object, but considerable computation is required to derive the desired colorimetric specifications.

Spectral

In the numerical specification of color, it is necessary to specify the spectral characterisitics of the illuminant and the spectral response of the observer. The CIE system (7) gives the spectral power distribution for various illuminants and the spectral response of the standard observer. Illuminant C has been used almost exclusively in the past in the specification of color, however, the use of Illuminant $D_{6500}$ (15) is now being considered. The specifications for Illuminant $D_{6500}$ include the ultraviolet region of the spectrum. The ultraviolet region for Illuminant C was not specified.

For color definition in the CIE system, the psychophysical response of the "standard observer" to the spectral distribution of light reflected from a specimen (as provided by the spectral power distribution of the illuminant and the spectral reflectivity curve) is matched by a combination of three standard stimuli, each of appropriate power. The relative levels for the three separate stimuli are the tristimulus values which together constitute the chromaticity of a color. It is more useful to compute the fraction each stimulus has to their sum since only two of the three fractions need be specified for chromaticity definition. It then becomes possible to restate the chromaticity of the measured color, for a given illuminant, in terms of "dominant wavelength" and "purity". To complete this specification of color, the luminous reflectance of the specimen is provided directly in the CIE system by the tristimulus value "Y".

Geometry

Four illumination and viewing conditions are recommended for use in the CIE system. These include illumination at 45° and viewing normal to the surface (0°), normal illumination with 45° viewing, diffuse illumination with normal viewing and normal illumination with diffuse viewing. Various advantages and disadvantages relate to each of these geometries from the viewpoint of best representing visual estimates of color. Generally, the geometry employed for visual inspection is more nearly 45°-0° or 0°-45°. Thus, an instrument equipped with this geometry would be expected to agree more closely with visual estimates than an instrument equipped with diffuse—normal geometry. It can be clearly demonstrated that a colorimetric evaluation using an instrument equipped with diffuse-normal geometry does not correlate closely with visual estimates for certain surfaces. Also, it is difficult to maintain a constant integrating cavity lining reflectance for long periods. The diffuse-normal geometry, however, is less sensitive to surface roughness and will give more reproducible results when specimens having an irregular surface are evaluated.

Control of the sizes, shapes and relative positions of the illuminated and viewed areas is also required for proper accounting of specimen translucency effects.

Photometry

Photometric accuracy of better than 0.1 point (0-100 scale) is desired.

Filter Colorimeters

Though the spectrophotometric approach to color measurement is the most basic and rigorous, its greater cost and computational demands have led to the development of filter colorimetry. One approach involves the use of suitable lamp, filters and photodetector combinations chosen to match the spectral functions of the CIE system ($\bar{x}$, $\bar{y}$, $\bar{z}$). Thus, the instrument output may be in the form of the tristimulus values of the CIE system. Although the $\bar{y}$ and $\bar{z}$ functions can be matched quite well, the double peak of the $\bar{x}$ function precludes the use of a single filter-photocell combination. Recourse is made either to the computation of the blue contribution to the $\bar{x}$ function from the $\bar{z}$ function (three-filter colorimeter) (16) or to the use of two filters with properly weighted combined output (four-filter colorimeter) for the $\bar{x}$ function. The latter gives a more accurate measure of the X tristimulus value particularly for specimens having spectral reflectivity curves with a steep slope through the blue region of the Spectrum. For color matching, particularly in control applications, the three or four-filter colorimeter may prove useful for many colors of commercial interest. However, it is subject to many limitations such as basic accuracy and the fact that colorimetric data are obtained for a single illuminant. For instance, the match may be metameric and under another illuminant there could be a serious mismatch.

Another form of colorimeter involves the use of a larger number of narrow-band filters with transmittance peaks distributed across the visible spectrum. If the filter transmittances are confined to sufficiently narrow ranges of wavelength and an adequate number are used, one may approach the utility of an abridged spectrophotometer. For many purposes of control, the abridged spectrophotometer can have important advantages over the three or four-filter colorimeter.

If a specimen exhibits fluorescence, the best spectrophotometer or filter colorimeter design utilizes illuminants with broad spectral power distribution, including appropriate intensities in the ultraviolet, with viewing through a monochromator for the spectrophotometer and through appropriate filters for the colorimeter. Thus, the fluorescent radiation will be excited in accordance with the spectral power distribution of the illuminant and the photodetector will view the reflected light and fluorescent radiation properly.

On-Machine Measurement of Optical Properties

The optical information which can be acquired on the moving web of a paper machine is limited essentially to that which can be obtained using a single sheet. Reflectances can be obtained for various conditions of illumination of the single sheet and for different backings. The backing can be black body or established at various reflectance levels. Ordinarily the backing would consist of ceramic or glass placed either at a specific distance from the sheet surface or in contact with the sheet. In addition to such reflectivity measurements as can be obtained, it is often possible to obtain useful transmittance information (except for very opaque sheets). Of course, where the transmittance is very low, the reflectance of a single sheet will approach the true $R_{\infty}$ value.

Optical specifications which properly apply to thick pad reflectances, $R_{\infty}$, are not readily abandoned in favor of specifications based on single sheet reflectances. Hence, the question of correlation of such on-machine data as can be obtained with actual experimentally determined $R_{\infty}$ data is of interest. The most useful approach is to utilize to the fullest possible extent the existing theory which permits calculation of $R_{\infty}$ from on-machine optical data. To the extent that such calculated values are not in agreement with the experimental data, empirical correlations could then be applied to bridge the remaining gap. Such an approach is more desirable than is dependence on empirical correlations alone especially if the calculated result is in close agreement with off-machine determinations.

The equations, based on the Kubelka-Munk theory, which interrelate various reflection and transmittance measurements are of principal interest in obtaining estimates of the reflectivity, $R_{\infty}$, from on-machine measurements. It is always necessary to obtain two different optical parameters preferably on the same areas of single sheets for the calculation of $R_{oo}$ using these equations. The two measurements can take many forms. For example, the reflectance of paper with black body backing ($R_o$) along with transmittance (T) is both appropriate and experimentally desirable. It is also possible to employ any two reflectances, obtained with different backings, but this introduces problems, particularly with the backing reflectance color. Through the appropriate measurement of two optical parameters, it is also possible to characterize papers in terms of their scattering and absorption powers—not possible with single reflectance measurements.

The theoretical relationship between $R_{oo}$, $R_o$ and T is given in equations 1 and 2. This relationship would be applied as far as possible for various desired spectral power distributions, such as are employed in standard brightness, TAPPI Opacity, and the various spectral functions associated with color measurement.

$$a = (1 + R_o^2 - T^2)/R_o \quad (1)$$

$$R_{oo} = (a/2) - \sqrt{(a/2)^2 - 1} \quad (2)$$

Where the $R_{oo}$ values are determined with the appropriate filters, the tristimulus values (Illuminant C) can be calculated as shown.

$$X(\text{blue}) = 0.1973 \, R_{oo} \quad (3)$$

$$X(\text{red}) = 0.7832 \, R_{oo} \quad (4)$$

$$X = X(\text{red}) + X(\text{blue}) \quad (5)$$

$$Y = R_{oo} \quad (6)$$

$$Z = 1.1812 \, R_{oo} \quad (7)$$

TAPPI Opacity can be calculated using equations 8 and 9 where R' is equal to 0.89.

$$R_{R'} = R_o + R'T^2/1 - R_oR' \quad (8)$$

$$C_{0.89} = 100 \, R_o/R_{R'} \quad (9)$$

Although it has often been demonstrated that the "balance of energy" equations and the Kubelka-Munk theory are very useful in interrelating the optical properties of paper determined under many different conditions of geometry and spectral power distributions, it is important to recall that some of the conditions required by theory are not met in practice. Among these, the specimen should be illuminated and viewed with diffuse light, monochromatic light should be employed and the optical properties of the material should conform to the requirement that the absorption and scattering of light be independent of each other and occur at numerous discrete sites spaced randomly throughout the substance. All reflectance and transmittance values should be determined on the absolute basis. The fact that these conditions are seldom met requires experimental testing of the theory for each intended use.

Experimental data were acquired to test the validity of this use of the theory for a number of "white" as well as more strongly colored papers. The extent of agreement which might be expected between the calculated reflectivity, $R_{oo}$, using equations 1 and 2 and experimentally determined $R_o$ and T values, and actually measured $R_{oo}$ values was examined for two different optical systems. Neither system would likely be used in making optical measurements on moving webs, but both serve the purpose of testing the relationships in actual use situations.

In the first set of experiments, handsheets were prepared from bleached hardwood pulp, refined to 450 ml C.S.F., at basis weights of 32, 64, 96 and 127 g/m². The optical properties of these samples were determined using the General Electric Recording Spectrophotometer with "reversed" optics (GERS-RF). The specimen was illuminated diffusely with the spectral power distribution of a tungsten filament source modified by the integrating cavity lining. Viewing of the specimen was at 6° to the normal. Four filters were interposed separately in the reflected beam to give the spectral response for the overall system of the $E_c\bar{x}$, $E_c\bar{y}$ and the $E_c\bar{z}$ functions of the CIE system. Two filters were utilized to obtain the $E_c\bar{x}$ function. The $R_{oo}$ values, calculated from the measured $R_o$ and T values using equations (1) and (2) are compared with the $R_{oo}$ values measured directly with the GERS-RF. The data given in Table III at the tenth page of the incorporated paper (Report No. 58 dated Jan. 10, 1974) are averages for five different specimens at each basis weight.

At the three highest basis weights, the agreement is excellent. For the lightest basis weight, the agreement is not quite as good. This is seen in the calculated color differences (17) between the computed and directly measured values given in Table IV of the incorporated paper. The tristimulus values were determined from the calculated and measured $R_{oo}$ values and the color differences ($\Delta E$), related to the difference in the tristimulus values, were obtained. A $\Delta E$ value of about one indicates, in our experience, that a just perceptible color difference exists under ideal conditions of viewing.

The lack of agreement for the lightweight sheets could be attributed in part to the much larger variability in the computed $R_{oo}$ values (not shown). Averaging of computed $R_{oo}$ value should not be employed when substantial differences in basis weight exist. Also, the discrepancies caused by the use of diffuse-6° rather than diffuse-diffuse geometry would be more pronounced at the lower basis weights.

A second experiment was conducted using five commercial, essentially nonfluorescent papers of widely different characteristics. In this case, spectral reflectivity curves were obtained for an opaque pad and for a single sheet using the conventional General Electric Recording Spectrophotometer (GERS) employing monochromatic illumination at 6° to normal and diffuse viewing. The spectral transmittance curves were also obtained with the GERS. Through integration of the product of the spectral reflectivity of transmittance curves and the CIE tristimulus functions using the IPC Mechanical Integrator (18), the tristimulus values were determined (Table V of the incorporated paper). The calculated and measured tristimulus values are in good agreement for the white and blue bond paper with rather poor agreement for the pink bond paper. The color differences based on the differences in the calculated and measured tristimulus values are given in Table IV.

Table IV

Color Differences ($\Delta E$) Related to the Differences Between the Calculated and Measured Tristimulus Values for Five Commercial Papers

| Commerical Papers | $\Delta E$ |
|---|---|
| White Bond | 0.6 |
| Tracing Paper | 1.6 |

Table IV-continued

Color Differences (ΔE) Related to the Differences
Between the Calculated and Measured Tristimulus Values
for Five Commercial Papers

| Commerical Papers | ΔE |
|---|---|
| Pink Bond | 8.9 |
| Coated Paper | 2.1 |
| Blue Bond | 0.9 |

Where the color differences are very large, it is probably attributable to the broad bandwidth of the spectral functions used to determine the tristimulus values and the substantial changes in reflectance with wavelength for the more highly colored papers. This can lead to error in the calculation of $R_{\infty}$ from $R_o$ and T. Such error would likely be eliminated if a reflectivity ($R_{\infty}$) curve were first calculated from the curves for $R_o$ and T (appropriate number of points should be used to give an accurate $R_{\infty}$ curve) before the integration leading to the tristimulus values is performed. But, of course, ths is not the means by which data are likely to be obtained and treated in an on-machine color measurement system, at least at present. The results indicate that, for many papers, the theoretical relationships will give excellent estimates of $R_{\infty}$ from $R_o$ and T acquired for single sheets. Where the discrepancies are greater than desirable, it is probable that useful empirical relationships may be established.

The estimation of $R_{\infty}$ from measurements of black body backed reflectance and transmittance of single sheets using theoretical relationships is subject to less error than are estimates obtained using two reflectances obtained with different backing reflectances, for example. A further approach to the design of on-machine color measuring instrumentation involves reflectances determined on single sheets backed by a body having a selected reflectance. Obviously, such reflectances will be equal to $R_{\infty}$ for any paper only if the effective reflectance of the backing is also equal to $R_{\infty}$ for that paper. Also, the backing will not ordinarily have the color of the paper. Hence, recourse must be made to empirical relationships between the measured reflectance values and the color of the samples as would be determined directly using opaque pads. Further, since it is often desirable to employ a spacing of some magnitude between the moving web and the backing surface, variations in the spacing which would likely occur in practice would be another source of discrepancy.

The following experiments were conducted to explore the differences in the color of paper when backed by a translucent opal glass and an opaque, enameled plaque. The spectral reflectivity curves for both backings was determined with the GERS and are given in the first figure at page eleven of the incorporated paper. It should be noted that these reflectivity curves cannot be used to determine the effective reflectances of the backings when employed against paper and, particularly for the translucent opal glass would be at different levels if determined with different geometry. Reflectance data on the paper specimens were obtained with both GERS-RF and with the Automatic Color-Brightness Tester (ACBT). The latter employs 45° illumination and normal viewing. Both instruments were equipped with appropriate filters so that the tristimulus values could be determined from four reflectance measurements (Illuminant C). Six commercial papers were evaluated with the white body backings at different spacings from the sheet.

$R_{\infty}$ values were measured experimentally for each sample and used as a standard against which the values determined with different spacings of the white body backing were compared. Reflectance values were obtained with the white body in contact with the paper and at spacings of 0.16, 0.32, and 0.64 cm from the sheet. Reflectance data were also obtained with a black body backing which represents infinite spacing between the white body and the sheet.

The data collected with the ACBT for the two backings are given in Tables VII and VIII of the incorporated paper. Data collected with the GERS-RF are presented in Tables IX and X of the incorporated paper. The color differences between the standard and the evaluations as single sheets under different backing conditions are presented in terms of the ΔE values. A description of the papers follows.

| Sample | Description |
|---|---|
| T | Tracing paper |
| N | Newsprint |
| C | Coated |
| R | Bond, red |
| W | Bond, white, $TiO_2$ filler |
| B | Bond, blue |

Assuming that a ΔE of 1.0 represents a just noticeable color difference for all samples under ideal conditions of viewing, an estimate of the change in spacing (centered about the spacing of 0.32 cm) between the sheet and backing which would result in this color difference is presented in Table XI of the incorporated paper. The magnitude of the effect of the change in spacing on the measured color is, of course, much less with highly opaque papers than with more transparent papers. It appears that a change in spacing of about 0.05 cm (0.02 inch) centered at 0.32 - cm spacing could be tolerated for many papers.

Web Factors which Influence the Measurement of Optical Properties

Basis Weight and Sheet Formation Variability

Basis weight variability, of which sheet formation represents a rapidly varying form, is a matter of interest in the on-machine measurement of optical properties. All optical properties are basis weight dependent in some degree. The dependence may arise because of changes in sheet structure with basis weight or may be a consequence of the simple change in mass per unit area for constant sheet structure. Thus, whereas the reflectance of a thick pad of paper may prove to be relatively independent of basis weight, the reflectance of a single sheet with black body or other designated backing and transmittance are expected to show basis weight effects. If the basis weight is known, it is possible to apply first-approximation corrections for departures in basis weight from a target value. However, such corrections would be different for different papers, would need to be developed experimentally and would best be applied to the longer-range basis weight variations.

Rapid changes in basis weight on the scale involved in sheet formation effects will result in rapidly changing optical properties as the moving sheet is scanned by an instrument in fixed position. The true time-varying signal might well be averaged by the on-machine instrument unlike the arithmetic averaging of the same optical property values determined statically off-machine. Whether the two averages are significantly different would depend both on the nature of the time-varying signal and the time-response characteristics of the on-machine instrument.

Where two optical measurements are made simultaneously at one position on a moving web, each would be averaged instrumentally. Values of $R_{\infty}$ calculated from such averages may differ from an average of $R_{\infty}$ values calculated from various pairs of optical values (for example, $R_o$ and T). Though such an error would be small for small basis weight variations, it could be of importance for some papers.

If sets of data are acquired on moving webs by interposing different filters in time sequence, for example, the particular values within a set would be obtained on different areas of the web and each could relate to a slightly different basis weight. Obviously if such values are affected by basis weight, the optical property described by the set (color, for example) would be in error if the basis weight were not constant. One could in such an instance, resort to the repetitive collection of sets of values with an averaging of the art results over a longer time period. It would be desirable to avoid the collection of data such that any particular value within a set is always obtained at the same unique web position or time cycle.

Fiber Orientation

Machine-made papers usually have some degree of fiber orientation which causes a difference in reflectance if the sheet is illuminated in the "in-machine" or "across-machine" direction. Generally, the reflectance is lower when the specimen is illuminated in the "in-machine" direction. Fiber orientation is usually less pronounced on the felt side; hence, optical data are usually obtained on that side. Standard brightness is measured on the felt side and the "in-machine" direction. On-machine measurements can of course, be performed in the same way.

Polarization of light occurs to some extent when a paper surface is illuminated at an angle such as 45° and the extent of polarization depends upon the kind of surface and to some degree upon fiber orientation. For this reason, the on-machine instrumentation should have the same response to polarized light as the off-machine instrument.

Two-Sidedness

Most papers have different spectral reflectivities for the felt and wire sides with the effect being more pronounced for very light basis weights and for coated papers. This affects the relationship between $R_o$, T and $R_{\infty}$ causing an error in the calculation of $R_{\infty}$. This effect is not large if the measurements of $R_o$, T, and $R_{\infty}$ are all made with the same side of the sheet facing the light beam on the on-machine as well as the off-machine instrument.

Moisture Content

In on-machine testing of paper, the moisture content may be at a level different from that employed in off-machine testing. Also, the intensity of the light incident on the specimen in some off-machine colorimeters is of a sufficiently high level to cause an appreciable change in temperature moisture content of the specimen during the course of performing a reflectance measurement.

Reflectance data have been obtained for "white" and dyed paper samples using the GERS and the ACBT, as these instruments employ a very low level of illumination thus minimizing departure from established laboratory environmental conditions. The GERS employs 6°-diffuse geometry with the specular component partially included and the ACBT employs 45°-0° geometry with the specular component excluded. Using both systems, one should be able to deduce if the change in reflectance of the specimen is due to changes in absorption, scattering, or surface structure. Changes in absorption and scattering would influence the data from both instruments in about the same way whereas changes in the specimen surface would influence the data differently. Changes in absorption could be more pronounced in selected portions of the spectrum whereas changes in scattering or surface should have a minor dependence on wavelength.

In the case of the GERS, air at different levels of relative humidity was passed throught the integrating cavity. Thus, the area of the specimen measured by the instrument was exposed to the conditions air while the measurement was being performed. The same was true for the ACBT except that the air was passed through the cylindrical opening in the instrument directly beneath the specimen opening.

* * *

[portion of text omitted]

* * *

The data show small changes for the "white" papers while the dyed papers and the newsprint show more significant changes. The effects were generally greater with the ACBT than with the GERS suggesting that changes in surface characteristics with changing relative humidity is principally involved. It is interesting to note that the reflectance of the red paper increased at 450 nm with increasing moisture content and decreased at 550 and 500 nm. This effect was noted with both instrument and is probably attributable to changes in light absorption.

Colorimetric data obtained with the ACBT at the several levels of relative humidity are given in Table XIII. The E value represents the color difference between the first determination at 5% relative humidity and the subsequent results. Several samples show a E value greater than one with sample "H" over two.

Sample A (fluorescent) has a reflectance of 85.0% for the GERS at 400 nm and 55.8 for the ACBT. This large difference is related to the erroneous evaluation of the fluorescent component by the GERS.

It appears that reflectance of paper, especially dyed papers, is significantly affected by changes in moisture content. Indications for the smaples tested are that changes in moisture content resulting from exposure to levels of relative humidity from 5 to 50% represent a reasonable limiting range for good accuracy.

Temperature

The web temperature would be higher for on-machine than off-machine testing. A study was performed to determine the effects of changing temperature on the reflectance of paper. The same paper samples (different specimens) evaluated in the moisture study were evaluated at four different temperatures. The GERS and the ACBT were employed because of their low level of illumination. Temperature at the surface of the specimen in the area exposed to the incident beam was determined with a 0.004-inch diameter wire chromel-alumel thermocouple. The junction was placed in contact with the paper surface. It is understood that differences in the absorption characteristics of the thermocouple and paper preclude the assumption that the paper surface and the junction temperature are the same when exposed to the incident radiation. However, when the temperature measurements were made, paper sample B was placed over the specimen opening in every case so that the relationship between junction and paper temperature should be fairly consistent for the different instruments.

* * *

[portion of text omitted]

* * *

A reasonable upper limit on temperature, as indicated by these data would be about 40° C. If on-machine measurements are made at higher temperatures, the potential effects of temperature may need to be considered for comparison with off-machine optical data.

Fluorescence

Widespread use of fluorescent dyes has made the matter of fluorescence an important factor in the measurement of optical properties of paper. The fluorescent "whitening" agents used in the paper industry generally absorb strongly in the violet and ultraviolet regions of the spectrum and emit light as somewhat longer wavelengths in the violet and in the blue regions of the spectrum. For fluorescent dyes, in general, the region of absorption may extend from the short wavelengths (ultraviolet) to the region where light is emitted by the dye. Actually, there may be some overlapping of the absorption and emittance regions.

In the case of the fluorescent "whitening" agents, the ultraviolet light needed to excite dye is largely absorbed in the surface layers of the sheet. Thus, with fluorescence present, reflectance would be most influenced whereas transmittance would be only minimally affected. This has a pronounced effect on the calculation of $R_{oo}$ from $R_o$ and T.

Properly designed instrumentation should be employed where fluorescence is a factor (19).

Web Position

In all optical instruments, the position of the web must be fixed at the appropriate design point. In the calibration of an instrument with paper or other material, a web position will be indicated. The moving web should, of course, be at the calibration position. This is best accomplished by ensuring that the web is in contact with a reference surface. Through establishing such contact, it is possible to have the optical instrumentation on one side of the web properly placed with respect to web position. The other side, however, must be maintained at the proper spacing. Changes in instrument to web distance can introduce errors of significant magnitude. Two options are available; the apparatus to web spacing may be fixed, or the spacing may be measured and corrections of the results made for changes from the desired spacing. The former method is preferred whenever possible.

Web flutter is obviously undesirable. If web flutter, exists web position is not known. Similarly, vibration of the optical apparatus may influence the results.

Web Speed

Potential effects due to web speed depend on the nature of the time constants of the optical instruments. For a time varying signal, with linear photometric response of the instrument, and with slow response, an appropriate arithmetic average value might be expected. However, if the time varying signal is not symmetrical about the mean value, the instrument may not indicate the mean correctly whereas the off-machine instrument could. Thus, the reading could be speed dependent under some conditions of sheet variability and instrument design.

Calendering

All optical properties of paper are affected by calendering of the sheet. Hence, on-line measurements of final paper properties must be made after calendering. In the usual application of optical apparatus between the calender and the reel, the measurements would be obtained only a fraction of a second after the sheet leaves the calender. It seems likely that the sheet would be undergoing compression recovery during this period and for some time after calendering with the result that changes in the sheet thickness and surface smoothness would occur between the time the on-line optical measurements are made and some later time when off-machine optical measurements are made. The possible importance of such effects is not known. The fact that they may occur is recognized as one of the possible factors leading to lack of agreement between on-line and off-machine measured optical properties.

Stray Light

It is usually possible to design optical instrumentation with proper shielding from stray light. Obviously, such shielding is required, since appreciable error may occur if stray light is permitted to enter the measurement zone.

Dust and Dirt

All on-machine optical instrumentation should be designed to eliminate or minimize dust or dirt accumulations. Some contamination cannot be avoided and compensation for its effect must be developed through frequent calibration of the on-machine apparatus.

Instrument Temperature

The optical as well as electronic components of optical devices are temperature sensitive. Best design involves control of instrument temperature to values above the ambient temperature of the machine room with the web in running position. Compensation for temperature is also possible, but less desirable.

Literature Cited

1. Van den Akker, J. A., Nolan, Phillip, and Wink, W. A., The Physical Basis of Standardization of Brightness Measurement, Paper Trade Journal, 114, No. 5: 34–40 (Jan 29, 1942).

2. Van den Akker, J. A., Dearth, L. R. and Shillcox, W. M., Evaluation of Absolute Reflectance for Standardization Purposes, J. Opt. Soc. Am., Vol 56, No. 2, 250–252, February 1966. D. G. Goebel, B. P. Caldwell and H. K. Hammond, Ill., Use of an Auxiliary Sphere with a Spectrophotometer to Obtain Absolute Reflectance, J. Opt. Soc. Am., 56, 783 (1966).

3. Van der Akker, J. A., Standard Brightness, Color and Spectrophotometry with Emphasis on Recent Information, Tappi Vol. 48, No. 12 (December, 1965).
4. Report No. 8 of the American Paper and Pulp Association. Parts I and II. Adaptability of the G. E. Reflection Meter as a Color Analyzer. Part III. The Effect of Infrared Fluorescence Radiation upon "Brightness" Measurements obtained with the G. E. Reflection Meter. Instrumentation Studies XIII. Paper Trade Journal 104, No. 18:47-53; No. 19:51-63; No. 20:45-49 (May 6, 13, 20, 1937).
5. Hofert, H. J., and Loof, H., Calibration of the Photometric Scale of a Reflectance Photometer, Zeitschrift fur Instrumentenkunde, Bol. 72 (1964) No. 5.
6. Davis, M. N., A simple and Reliable Photo-Opacity Tester, Tech. Assoc. (TAPPI) Papers, Ser. 16, 16,277 (1933).
7. Hardy, A. C., Handbook of Colorimetry, The Technology Press, Massachusetts Institute of Technology, Cambridge, Mass. (1936).
8. Report No. 22TO: American Paper Institute Instrumentation Program, Part VI. Comparison of TAPPI and Printing Opacity Determined with Five Instruments, May 8, 1971.
9. Stokes, G. G. On the Intensity of the Light Reflected from or Transmitted through a Pile of Plates. Proc. Roy. Soc. London, 11, 545 (1860-1862).
10. Kubelka, P., and Munk, F., A. Tech. Physik 12:593-601 (1931).
11. Kubelka, P., New Contributions to the Optics of Intensely Light-Scattering Materials. JOSA, Vol. 38, No. 5 (May, 1948); errata, ibid, 38, 1067 (1948); ibid, 44, 330 (1954).
12. Van der Akker, J. A., Tappi 32, No. 11:498-501 (November, 1949).
13. Reflectance-Opacity Chart for White Backing of 0.89. (Judd, 1937).
14. Van der Akker, J. A., Tappi 50, No. 5:41A (May, 1967).
15. Official Recommendations of the International Commission on Illumination Publication CIE No. (E-1.3.1) 1971.
16. Van der Akker, J. A., Chromaticity Limitations of the Best Physically Realizable Three-Filter Photoelectric Colorimeter. J. Opt. Soc. Am. 27, No. 12:401-407 (December, 1937).
17. McAdam, David L. "Color Measurement and Tolerances." Official Digest (Federation of Societies for Paint Technology). 38, 1487-1531 (1965). Chickering, JOSA, 57, 537 (1967).
18. Van der Akker, J. A. A Mechanical Integrator for Evaluating the Integral of the Product of Two Functions and its Application to the Computation of I.C.I. Color Specifications from Spectrophotometric Curves. J. Opt. Soc. Am. 29, No. 9:364-369 (September, 1939).
19. Grum, F. Instrumentation in Fluorescence Measurement, Journal of Color and Appearance, Vol. 1, No. 5:18-27 (April/May, 1972).

* * *

[The section entitled "Captions for the Figures" and FIGS. 1-7 of drawings are omitted]

* * *

General Discussion of the Disclosure of FIGS. 1-20

A basic conception of the on-machine system of FIGS. 1-20 is crucially concerned with the art of paper manufacture wherein numerous grades and weights of paper are to be manufactured, and wherein access to the paper web for measurement of paper optical properties during the manufacturing process is restricted to a section between the calendering stack and the reel. The environment at this location has been detailed in the preceding section. By measuring two essentially independent optical parameters, for example measuring both the reflectance and transmittance with respect to incident light of the necessary spectral distribution, it is possible to calculate paper optical properties on the basis of existing theory with an essential independence of basis weight. The feasibility and effectiveness of this approach is confirmed in the preceding section.

Closely related to the foregoing is the conception of utilizing as nearly as practicable the optical response characteristics and geometry of existing instruments used in the paper industry, so as to achieve as close a correlation as possible with present off-line measurements of color and brightness, for example. Also of substantial significance is the conception of providing a rugged and compact temperature-stabilized instrument capable of reliable and accurate on-machine measurement of color, brightness and opacity.

The reduction to practice of these basic conceptions has included several sponsored projects at the Institute of Paper Chemistry as reflected by the preceding section and has included laboratory testing of a prototype device for accuracy and reliability on a wide range of paper samples, with careful comparison being made with corresponding measurements using standard laboratory instruments. Details of the life testing of the prototype unit over a ten-month period and the adaption of the device to reliable and stable operation on the paper machine have been included herein to document the practical implementation of the on-machine system. Because of the critical need for rapid calculation of paper optical properties in an on-machine device, the necessary computer programming has been developed and is fully disclosed herein.

An important aspect of the disclosure relates to the measurement of the basis weight of the moving paper web concurrently with the simultaneous measurement of reflectance and transmittance values for essentially a common region of the web. Using the calculated value of infinite reflectance $R_{oo}$ (including the grade correction factor) and the value of transmittance T, for example, for the same sample region, along with a concurrently obtained, average value for basis weight, essentially accurate values of scattering coefficient s and the absorption coefficient k are obtained. Such coefficients will exhibit essential independence of any variations in the basis weight of the paper sheet material under these circumstances.

The measurement of both a reflectance and a transmittance value for a common sample region has an advantage over the measurement of two reflectance parameters under conditions such as found in the paper manufacturing process since the transmittance measurement is relatively insensitive to misalignment or tilting of the optical axis 515 of the backing assembly or lower sensing head 12, FIG. 3, relative to the optical axis 15 of the sensing head 11. This advantage is especially important for sheet material of relatively high opacity where two reflectance parameters would tend to be relatively close in value.

Generally the results of laboratory tests discussed herein are expected to be applicable to the on-line system. Thus the spread between values of $R_{oo}FC$ (See Table 3) obtained by the illustrated on-line system and the corresponding values of $AR_{oo}FC$ taken as standard should not differ by more than about plus or minus two points on a scale of zero to one hundred, prior to any grade correction, for a wide range of paper sheet materials of different color and basis weight.

The samples for which such accuracy was obtained in the laboratory included a range of basis weights of from 60 grams per square meter to 178 grams per square meter for white paper. Without the use of a correction factor, calculated $R_{oo}$ values which fell within two points of the measured value included samples of paper colored white (several tints), green, blue, canary, russett, ivory, gray and buff. Colors including pink, gold, salmon, and cherry required a significant correction factor for the $X_R$, $Y_C$, and $Y_A$ functions. All of the calculated $R_{oo}$ values involving the $X_B$ and Z functions fell within 0.77 units of the measured value on a scale of zero to 100, again without the use of any correction factor and regardless of color or basis weight.

The term quantitative measure of paper optical properties as used in the claims refers to output quantities of a numerical nature such as supplied by the on-line digital computer system 966, FIG. 6, programmed as explained herein with reference to FIGS. 7-20. Examples of such quantities are those indicated in block 990, FIG. 20; these quantities are identified with the corresponding conventional paper optical properties in Table 21.

The term on-machine optical monitoring device is intended generically and refers to the device 10, FIGS. 1 and 2, and other comparable devices for sensing two essentially independent optical response parameters such that a paper optical property is characterized prior to use of any correction factors with substantially improved accuracy in comparison to any characterization (prior to correction factors) of such paper optical property from either of such optical response parameters taken by itself. Such a monitoring device may be used as an aid to manual control of the paper making process or may be used as part of a closed loop automatic control system. Thus "monitoring" does not exclude active control in response to the output signals from the monitoring device.

Within the scope of the present subject matter, one or more of the following paper optical properties may be sensed: brightness, color, fluorescence, and/or opacity. Control of brightness and fluorescence offers a very substantial potential for cost reduction in the production of a significant range of paper types. Color control, on the other hand, may have important consequences regarding flexibility of manufacture, product uniformity, and grade change flexibility.

The value of on-line opacity control has already been demonstrated to a large degree in a prior closed loop analog opacity controller. In this installation, the average opacity across the web is controlled almost exactly at any given desired value. In previous manually controlled operations, the PKT (Pigmentary Potassium Titanate $K_2O6T_iO_2$ by du Pont) flow was set to some value chosen by the beater engineer and usually held to such value for the duration of the run of a given grade and weight. In the meantime, the paper opacity varied up and down, depending on process conditions at the time. Since the installation of the analog opacity controller, the opacity set point is adjusted rather than the PKT flow, thus holding opacity constant at the desired level. Instead of opacity, the PKT flow now varies up and down to compensate for other presently unavoidable process upsets resulting from variations in broke richness, PKT solids, dye usage, save-all efficiency, and other machine retention conditions. For a complete discussion of the installation of the analog opacity controller, reference is made to F. P. Lodzinski article "Experience With a Transmittance-Type On-Line Opacimeter for Monitoring and Controlling Opacity", Tappi, The Journal of The Technical Association of The Pulp and Paper Industry, Vol. 56, No. 2, Feb. 1973. This article of February, 1973 is incorporated herein by reference.

To assist in indicating the scope of the present joint invention, the substance of excerpts from an early conception record by one of the present inventors are set forth in the following paragraphs, headed "Proposed Instrument Design". The proposed design can be provided with a common backing window member conforming with window 135, and as thus modified is presented as an alternative embodiment of the joint invention.

Proposed Instrument Design:

An instrument made up of two scanning sensing heads, one above and one below the moving paper web, and a dedicated computer with appropriate couplers for input and output, is envisioned. The bottom head would receive light transmitted through the sheet and subsequently analyzed for its X, Y, and Z tristimulus components. It would also contain a backing of some specified effective reflectance (possibly a black body of zero, or near zero, reflectance) located just ahead or behind (machine direction) of the transmitted light receptor compartment(s).

The upper head could contain the light source, as well as a reflected light receptor. The latter occurs after reflection from the moving web at a point just above the backing, on the bottom head and would also be analyzed for its X, Y, and Z tristimulus components. Both light receivers and, for that matter, the light source itself could be integrating cavities of a type. This would be one way to insure the uniform distribution of emitted, transmitted, and reflected light in the X-direction in addition to providing identical samples of light going to each photoelectric cell installed with filters within the cavities themselves. Thermostatically controlled heaters or coolers would likely be desirable for temperature control. The flux of the light source could be monitored or controlled by a third partial, or full, set of filter-photocell combinations. The availability of both the transmitted (T) and reflected ($R_g$) light signals described above allows for precise computation of the reflectance with an infinite backing ($R_{oo}$). It is the latter, $R_{oo}$ value, which is required to characterize color, brightness, and an index of fluorescence. In addition, it would eliminate the need for any grade corrections in measuring either printing of TAPPI opacity, both of which could be made available if desired.

A small, rather low-cost, dedicated computer with appropriate interface equipment, could be used to receive all signals, compute all pertinent optical properties, and determine the signal for direct, closed loop control of:

a. 2-5 separate conventional dye additions;
b. fluorescent dye feed to the size press; and
c. PKT, $TiO_2$, or other slurry flow;

so that brightness, opacity, color (L, a,b) and fluorescence could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads to optical measurements and flow feeds with which paper manufacturers are familiar. The combined mathematical technology above is also sufficient for adequate decoupling of this otherwise complicated information so that overlapped control is avoided.

Use of a dedicated computer would eliminate most of the electronics now associated with optical measuring equipment. It could also be used to integrate results across the web and simplify and/or maintain calibration. The package would lend itself to rather universal application and minimize the time and effort on the part of the purchaser.

The key feature of this proposed instrument, which distinguishes it from existing on-line optical testers, is that it calls for the measurement of both transmitted and reflected light without undue complications. This, in turn, can cause a great deal of improvements regarding sensitivity, accuracy, flexibility, and thoroughness of a continuous optical property measuring device.

The following Table will serve to identify the computer symbols used in FIGS. 17-20 with the corresponding conventional symbols and terminology used in the text.

Table 21
Indentification of Computer Symbols Used in FIGS. 17-20

| Computer Symbol | Conventional Symbol | Conventional Term for Symbol |
|---|---|---|
| SGCF | GC(Table 3) | specific grade correction factor |
| RG | RD(Table 3) | Nominal reflectance of the diffuser window 135 |
| TD | $T_d$ | Nominal transmittance of the diffuser window 135 |
| RZERO (RZTABL) | $R_0$(Table 3) | reflectance with black body backing for each filter wheel position I equals zero through five. |
| T (TTABL) | T(Table 3) | Transmittance with black body backing for each filter wheel position I equals zero through five. |
| RINF (RITABL) | $R_\infty$ (Table 3) | infinite backing reflectance for filter wheel positions 1 equals zero to five. |
| S (STABL) | S | scatter coefficient for each filter wheel position I equals zero through five. |
| K | K | absorption |

Table 21-continued
Indentification of Computer Symbols Used in FIGS. 17-20

| Computer Symbol | Conventional Symbol | Conventional Term for Symbol |
|---|---|---|
| (KTABL) | | coefficient for each filter wheel position I equals zero through five. |
| ZFLUOR | — | fluorescent contribution to tristimulus Z reflectance |
| ZRINF | — | tristimulus Z infinite backing reflectance with fluorescence |
| XBRINF | — | tristimulus $X_B$ infinite backing reflectance with fluorescence |
| BRRINF | — | TAPPI brightness (see Table I in the first section of this Topic for spectral distribution of the first filter wheel position) |
| POPAC | $R_0/R_\infty$ | printing opacity |
| YAR89 | $R_0.89$ | tristimulus Y reflectance with .89 backing |
| TOPAC | $R_0/R_0.89$ | TAPPI opacity |
| XTRI | X | C.I.E. tristimulus coordinate X |
| YTRI | Y | C.I.E. tristimulus coordinate Y |
| ZTRI | Z | C.I.E. tristimulus coordinate Z |
| LH | L | Hunter coordinate L |
| AH, BH | a,b | Hunter coordinates a, b. |

Discussion of Further or Anticipated Modifications and Further Information Relative to the Preferred Embodiment Changes Made to the On-machine System of FIGS. 1-6.

1. Light source lamp terminals were connected to test tip jacks so that lamp voltage (at the lamp) can now be quickly measured without opening the case.

2. An easily removable doorway was cut from the top of the upper head case so that the photocell and amplifier gain circuits are much more accessible now. The photocell can now be easily removed and its 3/16" diameter aperture viewed directly from above without removing the case. This permits a quick check to see whether the two heads are properly aligned. The diffuser 276, FIG. 3, in the photocell aperture will be uniformly lighted when alignment is correct. Non-uniform illumination of this diffuser is quite apparent when the heads are improperly aligned.

3. A temperature sensitive resistor is located in the upper head adjacent to the photocell. Conductors are connected to lugs on the power supply panel so that such resistance measurements are easy to acquire. An empirically prepared chart is used to convert the resistance to temperature. Thus, an upper head temperature can be monitored from the remote power supply panel. (This temperature measuring device has been on the OMOD since it was first constructed.)

4. The upper head weighs 20 lbs. and the lower head 9¾ lbs. The weight of the mounting brackets are 7 and 5 lbs., respectively. (The compact size and light weight of these heads is an important advantage when it comes to providing means of installing and traversing across the web).

5. The reason we choose the 45°-0° geometry is because this geometry is used in the standard TAPPI brightness measurement. There is no standard TAPPI color test geometry at this time. It is considered that the 45°-0° geometry with the light plane in the machine direction is the proper geometry for color measurement as well. The reason for this is that most of our paper products where brightness and color are important are eventually used for written communications purposes. Consequently, they are viewed on a table top or desk with the human eye and light source approximating the 45°-0° geometry as employed in the OMOD. Moreover, the grain direction of the paper (grain long 8½ × 11 letterhead for example) is such that this directional effect is also simulated by the OMOD. Diffuse viewing is impossible by the human eye and diffuse illumination is quite unlikely in most offices or places of paper use.

Anticipated Computer Program Changes

1. We plan to test each individual reading of transmittance and reflectance (T and R) and compare it to the previously smoothed values. The latest individual readings will not be used to update the smoothed average whenever a difference between the two is greater than X %. The value of X will remain flexible, but likely in the neighborhood of 5-10%. This subprogram will reject and flag bad data since the paper optical properties could hardly change faster than this between readings. An exception is the very beginning of a run; however, the heads are not put on sheet until the operation has settled down somewhat anyway. Only the startup of a run will need to be manual or feed forward as far as color, brightness, and opacity control is concerned.

2. Initialization of the smoothing algorithm of R and T will be made to occur only when a grade change occurs; i.e., whenever a new set of specific grade correction factors are entered into the computer memory. There should not be any need for re-initialization for any other reason. Even basis weight changes occur gradually enough to permit the use of the previously stored smoothed averages without serious difficulty. We may, however, consider the use of an operator command to re-initialize such algorithms if found desirable.

3. For the No. 6 paper machine (shown in FIGS. 1 and 2), the OMOD heads will be pushed completely off the web on the front side to allow the basis weight gauge (mounted side of the OMOD) to measure right up to the front edge. The program will, therefore, need to be modified to reject data acquired whenever this occurs. Since the head position will be known, from the basis weight profile monitoring system, such data can be left unused whenever the position "Y" or greater is reached.

It turns out that this particular situation provides a convenient means of servicing the OMOD. The traversing mechanism can be stopped when the OMOD heads are pushed beyond the web edge where they are quite accessible for examination, checking of standardization, etc.

Current Program Listing

GE-PAC 4020 Program Listing Characteristics

The following program listings are considered to be in conformity with the flow charts of FIGS. 8–20. The listing is provided by the General Electric PAC 4020 process control computer, and the following general discussion explains the GE-PAC 4020 program listing characteristics.

I. The first page contains the following unique information:
  A. Line 1-control statement, with time of day and activity.
  B. Lines 2 and 3 contain program identification numbers.

II. The remaining information is broken into three parts as follows:
  A. The three left-most columns of numbers consist of assembler-generated machine coding:
    1. The first column of numbers consists of the octal location, relative to the beginning of the program.
    2. The second column of numbers consists of the contents of the octal location in absolute form-the first two numbers signify the operation code; the third number signifies the index register, if any; and the remaining five numbers signify the absolute operand of the instruction.
    3. The third column of numbers consists of the contents of the octal location in relative form-it is identical to (2), except the five right-most numbers signify the relative operand from the location of the instruction.
  B. The next eighty columns correspond to the symbolic instructions from which the assembler generated the machine coding.
    1. Statements beginning with an asterick or "C" are comments only, with respectively a 6 or 7 in column seventy.
    2. Other statements are divided as follows: label, if any; symbolic operation code; symbolic operand, if any; index register preceded by a comma, if any; comment, if any; and 6, 7 or 1 in column seventy.
    3. The 6 in column seventy indicates a programmer-defined assembly language statement. The 7 in column seventy indicates a programmer-defined Fortran language statement. The 1 in column seventy indicates an assembler-defined assembly language statement, such as symbolic coding generated from a programmer-defined Fortran statement.
  C. The right-most column contains the line sequence number of the printout.

Program Listing For Program Fourteen (FIGS. 8–16)

The following listing is presented to illustrate the extent of the programming effort to implement the flow charts of FIGS. 8–16. It will be observed that the implementation of these flow charts together with the changes previously indicated herein and any necessary debugging is within the routine skill of the art.

```
101014 COMPILE
        814030060   814030060              IDN 000000                                                                       1
        814030060   814030060                                                                                               1
                                            CTABL EQL 12                                                                    6
                                            STTABL EQL 28                                                                   6
                                            RGTABL EQL 44                                                                   6
                                            VTABL  EQL 60                                                                   6
                                            SGTABL EQL 76                                                                   6
                                            OUTABL EQL 92                                                                   6
                                            STABL  EQL 102                                                                  6
                                            KTABL  EQL 110                                                                  6
                                            RSTABL EQL 118                                                                  6
                                            MPAR   EQL 134                                                                  6

*PROG 14                                                                         6

*TURNED ON INITALLY BY TYPER-THEREAFTER ON 1 SEC. BY AUXTIMER =5                 6
 000000  00002100    00002100              E014  LDA TIME                                                                   6
 000001  32002707    32002707                    STA AUXTM+3                                                                6

*LOAD FILEX STARTING ADDR. INTO INDEX REGISTER                                   6
 000002  16300414    16340412              EVERYL LDX FILEX,3                                                               6

*LOAD PCH ADD OF LOOPS P+Q FROM P.F. X4>P REFLECT.CELL X5>Q TRANS.               6
 000003  00300001    00300001                    LDA 1,3                                                                    6
 000004  32000004    32000004                    STA 4              P                                                       6
 000005  00300002    00300002                    LDA 2,3                                                                    6
 000006  32000005    32000005                    STA 5              Q                                                       6

*LOAD PCW:S OF LOOPS P+Q + CHECK IF OFF SCAN                                     6
 000007  00400000    00400000                    LDA 0,4            P                                                       6
 000010  05004727    05004727                    TOD 23                                                                     6
 000011  30000647    30040636                    BTR TRNOFF                                                                 6
 000012  00500000    00500000                    LDA 0,5                                                                    6
 000013  05004727    05004727                    TOD 23                                                                     6
 000014  30000647    30040633                    BTR TRNOFF                                                                 6

*SET UP AUXTIMER TO RE-RUN IN 1 SECOND                                           6
 000015  25030000    25030000                    IAI                                                                        6
 000016  00002707    00002707                    LDA AUXTM+3                                                                6
 000017  11000406    11040367                    ADD DLYTIM                                                                 6
 000020  32002707    32002707                    STA AUXTM+3                                                                6
 000021  25020000    25020000                    PAI                                                                        6

*LOAD SLOWDOWN CTR.FROM X3 DECRIMENT IT BY ONE                                   6
 000022  00300004    00300004                    LDA 4,3                                                                    6
 000023  31002025    31002025                    SUB ONE                                                                    6
 000024  66000027    66040003                    BZE RESTOR                                                                 6

*STORE NEW COUNT BACK IN FILE X + RTN.TO RTMOS                                   6

000025  32300004    32300004                    STA 4,3                                                                    6
 000026  14000375    14040347                    BRU RTNRTM                                                                 6

*RESTORE                                                                         6

*RESTOR SLOWDOWN COUNT TO INITAL VALUE                                           6
 000027  00300005    00300005              RESTOR LDA 5,3                                                                   6
 000030  32300004    32300004                    STA 4,3                                                                    6

*READ FILTER POSITION INDEX FROM FILE + INDEX BY 1                               6
 000031  00300006    00300006                    LDA 6,3                                                                    6
 000032  60000001    60000001                    AKA 1                                                                      6
 000033  32300006    32300006                    STA 6,3                                                                    6

*IS INC >OR LESS THAN 6                                                          6
 000034  50000007    50000007                    SKA 7                                                                      6
 000035  05004727    05004727                    TOD 23                                                                     6
 000036  34000066    34040030                    BTS LDDIDG         YES                                                     6

*SET LOST INDEX REFERENCE TEMP FLAG                                              6
 000037  40000001    40000001                    LDK 1                                                                      6
 000040  32000413    32040353                    STA LIRFLG                                                                 6

*OUTPUT AN ALARM FOR STUCK FILTER                                                6

*TEST IF DISK IS DOWN                                                            6
 000041  00002777    00002777                    LDA DISCOF                                                                 6
 000042  05004700    05004700                    TOD 0                                                                      6
 000043  34000061    34040016                    BTS NOALRM                                                                 6
```

```
                                    *PRINT MSG.                                                6
                                        PRINT 10                                               7
000044  40000051  40040005              LDK $10                                                1
000045  45004330  45004330              MAQ                                                    1
000046  33000561  33000561              SPB SPRINT                                             1
000047  33000564  33000564              SPB SHLOUT                                             1

10  FORMAT ($ OMOD FILTER STUCK$)                         7
000050  14000061  14040011              BRU SM0                                                1
000051  40220000  40220000          $10 CON 0,40220000                                         1
000052  10047515  10047515              CON A,3, OM                                            1
000053  23642040  23642040              CON A,3,OD                                             1
000054  21444514  21444514              CON A,3,FIL                                            1
000055  25042522  25042522              CON A,3,TER                                            1
000056  10051524  10051524              CON A,3, ST                                            1
000057  25241513  25241513              CON A,3,UCK                                            1
000060  60077770  60077770              CON 0,60077770                                         1

000061  300000000 300000000        SM0 BSS 0                                                   1
000061  16300414  16340333         NOALRM LDX FILEX,3.                                         6

*REINITILIZE SMOOTHED DATA K>7                             6
000062  40000007  40000007              LDK 7                                                  6
000063  32300011  32300011              STA 9,3                                                6

*SET UP CYCLE COUNTER FOR 1 DUMMY DATA SET                 6
000064  40000001  40000001              LDK 1                                                  6
000065  32300012  32300012              STA 10,3                                               6

*LOAD DIGITAL INPUT STATUS WORK FOR GROUP /1400            6
000066  25051400  25051400              LDDIDG IN /1400                                        6

*IS FILTER IN POSITION ZERO:                               6
000067  05004726  05004726              TOD 22                                                 6
000070  30000123  30040033              BTR LOSTIX                                             6

*I>7 !                                                     6
000071  00300006  00300006              LDA 6,3                                                6
000072  50000007  50000007              SKA 7                                                  6
000073  05004727  05004727              TOD 23                                                 6
000074  30000120  30040024              BTR REFILT                                             6

*REINITILIZE SMOOTHED DATA K>7                             6
000075  40000007  40000007              LDK 7                                                  6
000076  32300011  32300011              STA 9,3                                                6

*SET UP DUMMY CYCLE >1                                     6
000077  40000001  40000001              LDK 1                                                  6
000100  32300012  32300012              STA 10,3                                               6

*OUTPUT SKIPPED FILTER MSG                                 6
                                        PRINT 20                                               7
000101  40000106  40040005              LDK $20                                                1
000102  45004330  45004330              MAQ                                                    1
000103  33000561  33000561              SPB SPRINT                                             1
000104  33000564  33000564              SPB SHLOUT                                             1

20  FORMAT ($ OMOD SKIPPED FILTER $)                      7
000105  14000117  14040012              BRU SM1                                                1
000106  40250000  40250000          $20 CON 0,40250000                                         1
000107  10047515  10047515              CON A,3, OM                                            1
000110  23642040  23642040              CON A,3,OD                                             1
000111  24645511  24645511              CON A,3,SKI                                            1
000112  24050105  24050105              CON A,3,PPE                                            1
000113  21020106  21020106              CON A,3,D F                                            1
000114  22246124  22246124              CON A,3,ILT                                            1
000115  21251040  21251040              CON A,3,ER                                             1

000116  60077767  60077767              CON 0,60077767                                         1
                                        CONTINUE                                               7
000117  300000000 300000000        SM1 BSS 0                                                   1
000117  16300414  16340275             LDX FILEX,3                                             6

*REINITILIZE FILTER INDEX >0                               6
000120  77300006  77300006         REFILT STZ 6,3                                              6
```

```
                                        *RESET LOST INDEX FLAG                              6
000121   77000413   77040272                STZ LIRFLG                                      6
000122   14000125   14040003                BRU SAVEIB                                      6
                                        *IS LOST INDEX FLAG SET                             6
000123   00000413   00040270             LOSTIX LDA LIRFLG                                  6
000124   67000372   67040246                BNZ BENTER          YES                         6

*NO-LOAD HEAD POSITION SCAN ONLY FILE ADD (129) FROM FILE INTO X7   6
000125   00300003   00300003             SAVEIB LDA 3,3                                     6
000126   32000007   32000007                STA 7                                           6

*IS HEAD STZ BIT 4 GROUP 1400 CLOSED!               6
000127   25051400   25051400                IN /1400                                        6
000130   05004704   05004704                TOD 4                                           6
000131   30000246   30040115                BTR CHKSTZ                                      6

*IS HPOS LESS THAN MIN.POS.                         6
000132   00700001   00700001                LDA 1,7                                         6
000133   31300010   31300010                SUB 8,3                                         6
000134   05004727   05004727                TOD 23                                          6
000135   34000154   34040017                BTS STDPRG                                      6

*IS STANDARDIZE IN PROG SET                         6
000136   00300000   00300000                LDA 0,3                                         6
000137   05004727   05004727                TOD 23                                          6
000140   30000143   30040003                BTR CHKMIN          NO                          6

*RESET STDZ IN PROGRESS                             6
000141   05046027   05046027                SBK 23                                          6
000142   32300000   32300000                STA 0,3                                         6

*IS HPOS LESS THAN MIN.POS.                         6
000143   00700001   00700001             CHKMIN LDA 1,7                                     6
000144   31300010   31300010                SUB 8,3                                         6
000145   05004727   05004727                TOD 23                                          6
000146   30000165   30040017                BTR CKIEO6                                      6

*INITILIZE FILTERED TABLE INITIALIZATION INDEX K>7 IN FILE X   6
000147   40000007   40000007                LDK 7                                           6
000150   32300011   32300011                STA 9,3                                         6

*INITILIZE TEMP FILTER CYCLE  CYCLE>1 SAVE IN FILE X   6
000151   40000001   40000001                LDK 1                                           6
000152   32300012   32300012                STA 10,3                                        6
000153   14000372   14040217                BRU BENTER                                      6

*IS STANDARDIZE IN PROGRESS BIT 23 SET!             6
000154   00300000   00300000             STDPRG LDA 0,3                                     6
000155   05004727   05004727                TOD 23                                          6
000156   34000165   34040007                BTS CKIEO6          YES                         6

*NO-SET STDZ IN PROGRESS                            6
000157   05046027   05046027                SBK 23                                          6
000160   32300000   32300000                STA 0,3                                         6

*INITILIZE TEMP. FILTER CYCLE INDEX TO 1 IN FILE X  6
000161   40000001   40000001                LDK 1                                           6
000162   32300012   32300012                STA 10,3                                        6

*INITILIZE FILTERED TABLE INITIALIZATION INDEX K>7  6
000163   40000007   40000007                LDK 7                                           6
000164   32300011   32300011                STA 9,3                                         6

*IS THE INITILIZATION INDEX GREATER THAN 6 !        6
000165   00300011   00300011             CKIEO6 LDA 9,3                                     6
000166   50000006   50000006                SKA 6                                           6
000167   05004727   05004727                TOD 23                                          6
000170   30000372   30040202                BTR BENTER                                      6

*NO-IS IT EQUAL TO 6                                6
000171   67000200   67040007                BNZ LDALPH                                      6

*IS THE CYCLE 0!OR MINUS                            6
000172   00300012   00300012                LDA 10,3                                        6
000173   66000200   66040005                BZE LDALPH                                      6
000174   05004727   05004727                TOD 23                                          6
000175   34000200   34040003                BTS LDALPH                                      6

*NO-DECRIMENT CYCLE INDEX + SAVE BACK IN FILEX      6
000176   50000001   50000001                SKA 1                                           6
000177   32300012   32300012                STA 10,3                                        6

*LOAD SMOOTHING CONSTANT FROM FILE                  6
000200   00300013   00300013             LDALPH LDA 11,3                                    6
000201   32000656   32040455                STA ALPHA                                       6

*LOAD BASIS WT. FILE ADD + PUT FLOATED PV IN FILEX<122   6
000202   00300007   00300007                LDA 7,3                                         6
```

| | | | | |
|---|---|---|---|---|
| 000203 | 32000006 | 32000006 | STA 6 | 6 |
| 000204 | 00600002 | 00600002 | LDA 2,6 | 6 |
| 000205 | 74020010 | 74020010 | FLO 8 | 6 |
| 000206 | 32300172 | 32300172 | STA 122,3 | 6 |

*INITILIZE LOOP INDEX J>0                                6

| | | | | |
|---|---|---|---|---|
| 000207 | 77000412 | 77040203 | STZ JINX | 6 |

*IS LOOP J ON SCAN                                       6

| | | | | |
|---|---|---|---|---|
| 000210 | 00400000 | 00400000 | LOOPJ LDA 0,4 | 6 |
| 000211 | 05004727 | 05004727 | TOD 23 | 6 |
| 000212 | 30000275 | 30040063 | BTR CHK2ND | 6 |

*YES-LOAD STDZ. CORRECTION FACTOR FROM FILEX INTO C      6

| | | | | |
|---|---|---|---|---|
| 000213 | 00000412 | 00040177 | LDA JINX | 6 |
| 000214 | 11000003 | 11000003 | ADD 3 | 6 |
| 000215 | 32000006 | 32000006 | STA 6 | 6 |
| 000216 | 00600014 | 00600014 | LDA CTABL,6 | 6 |
| 000217 | 32000654 | 32040435 | STA CTABLE | 6 |

*LOAD PV FROM SCAN ONLY FILE(J)                          6

| | | | | |
|---|---|---|---|---|
| 000220 | 00400001 | 00400001 | LDA 1,4 | 6 |
| 000221 | 32000007 | 32000007 | STA 7 | 6 |
| 000222 | 00700001 | 00700001 | LDA 1,7 | 6 |

*CONVERT TO ENGINEERING UNITS B1                         6

| | | | | |
|---|---|---|---|---|
| 000223 | 31000410 | 31040165 | SUB EIGHTH | 6 |
| 000224 | 45004414 | 45004414 | DRA 12 | 6 |
| 000225 | 65000407 | 65040162 | DVD THRTY2 | 6 |
| 000226 | 00000010 | 00000010 | LDA /10 | 6 |
| 000227 | 74020001 | 74020001 | FLO 1 | 6 |
| 000230 | 32000653 | 32040423 | STA NCELL | 6 |

REAL NCELL,NFCELL                                 7

CCALC CORRECT INPUT                                      7

NCELL=NCELL*CTABLE                                7

| | | | | |
|---|---|---|---|---|
| 000231 | 00000653 | 00040422 | LDA NCELL | 1 |
| 000232 | 72000654 | 72040422 | FMP CTABLE | 1 |
| 000233 | 32000653 | 32040420 | STA NCELL | 1 |

CONTINUE                                          7

| | | | | |
|---|---|---|---|---|
| 000234 | 16300414 | 16340160 | LDX FILEX,3 | 6 |
| 000235 | 00000412 | 00040155 | LDA JINX | 6 |
| 000236 | 11000003 | 11000003 | ADD 3 | 6 |
| 000237 | 32000006 | 32000006 | STA 6 | 6 |

*K GREATER THAN ZERO                                     6

| | | | | |
|---|---|---|---|---|
| 000240 | 00300011 | 00300011 | LDA 9,3 | 6 |
| 000241 | 66000243 | 66040002 | BZE LDPREV | 6 |
| 000242 | 76000246 | 76040004 | BNM CHKSTZ | 6 |

*LD.PREV SMOOTHED VALUE FROM FILEX INTO TEMP PFCELL      6

| | | | | |
|---|---|---|---|---|
| 000243 | 00600074 | 00600074 | LDPREV LDA VTABL,6 | 6 |
| 000244 | 32000657 | 32040413 | STA PFCELL | 6 |
| 000245 | 14000253 | 14040006 | BRU SMOALG | 6 |

*IS STANDARDIZE IN PROGRESS BIT SET                      6

| | | | | |
|---|---|---|---|---|
| 000246 | 00300000 | 00300000 | CHKSTZ LDA 0,3 | 6 |
| 000247 | 05004727 | 05004727 | TOD 23 | 6 |
| 000250 | 34000272 | 34040022 | BTS LDPVJ | 6 |

*NO-MAKE PREV. SMOOTHED VALUE EQUAL TO NEW UNSMOOTHED INPUT  6

| | | | | |
|---|---|---|---|---|
| 000251 | 00000653 | 00040402 | LDA NCELL | 6 |
| 000252 | 32000657 | 32040405 | STA PFCELL | 6 |

*SMOOTHING ALGORITHM                                     6

| | | | | |
|---|---|---|---|---|
| 000253 | 300000000 | 300000000 | SMOALG BSS 0 | 6 |

NFCELL=ALPHA*NCELL+(1.-ALPHA)*PFCELL              7

| | | | | |
|---|---|---|---|---|
| 000253 | 00000656 | 00040403 | LDA ALPHA | 1 |
| 000254 | 72000653 | 72040377 | FMP NCELL | 1 |
| 000255 | 32000652 | 32040375 | STA STEMP | 1 |
| 000256 | 00000651 | 00040373 | LDA SFLCON | 1 |
| 000257 | 71000656 | 71040377 | FSU ALPHA | 1 |
| 000260 | 72000657 | 72040377 | FMP PFCELL | 1 |
| 000261 | 70000652 | 70040371 | FAD STEMP | 1 |
| 000262 | 32000655 | 32040373 | STA NFCELL | 1 |

CONTINUE                                          7

| | | | | |
|---|---|---|---|---|
| 000263 | 16300414 | 16340131 | LDX FILEX,3 | 6 |
| 000264 | 00000412 | 00040126 | LDA JINX | 6 |

| | | | | | |
|---|---|---|---|---|---|
| 000265 | 11000003 | 11000003 | | ADD 3 | 6 |
| 000266 | 32000006 | 32000006 | | STA 6 | 6 |

*SAVE NEW SMOOTHED VALUE BACK IN FILEX

| | | | | | |
|---|---|---|---|---|---|
| 000267 | 00000655 | 00040366 | | LDA NFCELL | 6 |
| 000270 | 32600074 | 32600074 | | STA VTABL,6 | 6 |
| 000271 | 14000275 | 14040004 | | BRU CHK2ND | 6 |

*LOAD PV FROM SCAN ONLY LOOP J FILE STORE IN FILEX STTABL(I,J)

| | | | | | |
|---|---|---|---|---|---|
| 000272 | 00700002 | 00700002 | LDPVJ | LDA 2,7 | 6 |
| 000273 | 74020001 | 74020001 | | FLO 1 | 6 |
| 000274 | 32600034 | 32600034 | | STA STTABL,6 | 6 |

*HAS SECOND INPUT BEEN PROCESSED

| | | | | | |
|---|---|---|---|---|---|
| 000275 | 00000412 | 00040115 | CHK2ND | LDA JINX | 6 |
| 000276 | 67000304 | 67040006 | | BNZ KZERO | 6 |

*LOAD LOOP Q PCH PUT IN X4 + SET J INDEX TO ONE +RELOOP

| | | | | | |
|---|---|---|---|---|---|
| 000277 | 00300002 | 00300002 | | LDA 2,3 | 6 |
| 000300 | 32000004 | 32000004 | | STA 4 | 6 |
| 000301 | 40000001 | 40000001 | | LDK 1 | 6 |
| 000302 | 32000412 | 32040110 | | STA JINX | 6 |
| 000303 | 14000210 | 14077705 | | BRU LOOPJ | 6 |

*IS K > TO ZERO

| | | | | | |
|---|---|---|---|---|---|
| 000304 | 00300011 | 00300011 | KZERO | LDA 9,3 | 6 |
| 000305 | 66000313 | 66040006 | | BZE ISTAND | 6 |

*NO-IS IT LESS THAN 0

| | | | | | |
|---|---|---|---|---|---|
| 000306 | 05004727 | 05004727 | | TOD 23 | 6 |
| 000307 | 34000372 | 34040063 | | BTS BENTER | 6 |

*NO-DECRIMENT INITILIZATION COUNT + SAVE IN FILE X

| | | | | | |
|---|---|---|---|---|---|
| 000310 | 50000001 | 50000001 | | SKA 1 | 6 |
| 000311 | 32300011 | 32300011 | | STA 9,3 | 6 |
| 000312 | 14000372 | 14040060 | | BRU BENTER | 6 |

*IS STANDARDIZE IN PROG SET

| | | | | | |
|---|---|---|---|---|---|
| 000313 | 00300000 | 00300000 | ISTAND | LDA 0,3 | 6 |
| 000314 | 05004727 | 05004727 | | TOD 23 | 6 |
| 000315 | 30000372 | 30040055 | | BTR BENTER | 6 |

*RESET STDZ BIT + SAVE IN FILEX

| | | | | | |
|---|---|---|---|---|---|
| 000316 | 05045027 | 05045027 | | RBK 23 | 6 |
| 000317 | 32300000 | 32300000 | | STA 0,3 | 6 |

*INITILIZE TEMP JCOUNT 0

| | | | | | |
|---|---|---|---|---|---|
| 000320 | 77000411 | 77040071 | | STZ JCOUNT | 6 |

*INITILIZE TEMP.COUNT ICOUNT>0

| | | | | | |
|---|---|---|---|---|---|
| 000321 | 77002660 | 77002660 | INITIO | STZ ICOUNT | 6 |

*LOAD CORR.CONST.FROM FILEX STTABL(ICOUNT,JCOUNT) INTO TEMP RG

| | | | | | |
|---|---|---|---|---|---|
| 000322 | 00000411 | 00040067 | LDCORR | LDA JCOUNT | 6 |
| 000323 | 11002660 | 11002660 | | ADD ICOUNT | 6 |
| 000324 | 11000003 | 11000003 | | ADD 3 | 6 |
| 000325 | 32000004 | 32000004 | | STA 4 | 6 |
| 000326 | 00400166 | 00400166 | | LDA RSTABL,4 | 6 |
| 000327 | 32000661 | 32040332 | | STA RG | 6 |

*LOAD OFF SHEET VALUES FROM FILEX STTABL(ICOUNT,JCOUNT)INTO TEMP ST

| | | | | | |
|---|---|---|---|---|---|
| 000330 | 00400034 | 00400034 | | LDA STTABL,4 | 6 |
| 000331 | 32000662 | 32040331 | | STA ST | 6 |

*CALC CORR. FACTOR

C=RG/ST

| | | | | | |
|---|---|---|---|---|---|
| 000332 | 00000661 | 00040327 | | LDA RG | 7 |
| 000333 | 73000662 | 73040327 | | FDV ST | 1 |
| 000334 | 32000660 | 32040324 | | STA C | 1 |

| | | | | | |
|---|---|---|---|---|---|
| | | | | CONTINUE | 7 |

* IF REFL.(JCOUNT>0) MULT CTABL(I,J) BY EMPIRICAL CORR. CONSTANT IN 6

* MPAR<5, IF TRANSMITTANCE (JCOUNT>1), MULT. BY MPAR<6.

| | | | | | |
|---|---|---|---|---|---|
| 000335 | 00000411 | 00040054 | | LDA JCOUNT | 6 |
| 000336 | 31002026 | 31002026 | | SUB TWO | 6 |
| 000337 | 05004727 | 05004727 | | TOD 23 | 6 |
| 000340 | 30000375 | 30040035 | | BTR RTNRTM | 6 |
| 000341 | 00000411 | 00040050 | | LDA JCOUNT | 6 |
| 000342 | 32000004 | 32000004 | | STA 4 | 6 |

```
000343  04400417  04440054              XEC CORCAL,4                                            6
000344  32000663  32040317              STA CORR                                                6

C=C*CORR                                                 7
000345  00000660  00040313              LDA C                                                   1
000346  72000663  72040315              FMP CORR                                                 1
000347  32000660  32040311              STA C                                                   1

CONTINUE                                                 7
000350  16300414  16340044              LDX FILEX,3                                             6
000351  00000411  00040040              LDA JCOUNT                                              6
000352  11002660  11002660              ADD ICOUNT                                              6
000353  32000004  32000004              STA 4                                                   6

*SAVE CORR FACTOR IN FILEX CTABL(ICOUNT,JCOUNT)>C         6
000354  00000660  00040304              LDA C                                                   6
000355  32400014  32400014              STA CTABL,4                                             6

*IS ICOUNT LESS THAN SIX!                                 6
000356  00002660  00002660              LDA ICOUNT                                              6
000357  50000005  50000005              SKA 5                                                   6
000360  05004727  05004727              TOD 23                                                  6
000361  30000365  30040004              BTR CKJCNT                                              6

*INX,ICOUNT BY 1                                          6
000362  60000001  60000001              AKA 1                                                   6
000363  32002660  32002660              STA ICOUNT                                              6
000364  14000322  14077736              BRU LDCORR                                              6

*IS JCOUNT GREATER THAN ZERO                              6
000365  00000411  00040024      CKJCNT  LDA JCOUNT                                              6
000366  67000372  67040004              BNZ BENTER                                              6
000367  60000001  60000001              AKA 1                                                   6
000370  32000411  32040021              STA JCOUNT                                              6
000371  14000321  14077730              BRU INITIO                                              6

*CLOSE FILTER ADVANCE SOLENOID DRIVE CONTACTS MOMENTARILY 6

*CALL TIMED OUTPUT RTMOS TIMED OUTPUT FOR .5 SEC.         6
000372  00000416  00040024      BENTER  LDA AREG                                                6
000373  42000415  42040022              LDQ TIMEQ                                               6
000374  33000445  33000445              SPB MORC04                                              6

*SET UP FOR AUXTIME TURNON IN ONE SEC.                    6
000375  00002707  00002707      RTNRTM  LDA AUXTM+3                                             6
000376  31002100  31002100              SUB TIME                                                6
000377  05004527  05004527              SOD 23                                                  6
000400  34000002  34077402              BTS EVERYL                                              6
000401  05046027  05046027              SBK 23                                                  6
000402  32000404  32040002              STA *+2                                                 6
000403  33000401  33000401              SPB DELC01                                              6
000404  300000001 300000001             BSS 1                                                   6
000405  14000002  14077375              BRU EVERYL                                              6
000406  00000020  00000020      DLYTIM  CON G.SECND*4                                           6
                                        DISCOF EQL /2777      TEMP-T1L-RE-ASSEMBLY              6
000407  00006200  00006200      THRIY2  CON D,3200                                              6
000410  06200000  06200000      EIGHTH  CON D,800B12                                            6
000411  00000000  00000000      JCOUNT  CON 0,0                                                 6
000412  00000000  00000000      JINX    CON 0,0                                                 6
000413  00000000  00000000      LIRFLG  CON 0,0                                                 6
000414  00063200  00063200      FILEX   CON 0,63200                                             6
000415  00017000  00017000      TIMEQ   CON D,30B15                                             6
000416  00000000  00000000      AREG    CON 0,0                                                 6
000417  00000213  00000213      CORCAL  LDA MPAR+5                                              6
000420  00000214  00000214              LDA MPAR+6                                              6
000421  300000226 300000226     FILEX1  BSS 150                                                 6
000647  33000404  33000404      TRNOFF  SPB OFFC01            TURN PROG OFF                     6
000650  10000000  10077130              PRG 0,1,0,E014,0                                        6

END                                                      7
000651  300000000 300000000             BSS 0                                                   1
000651  300000000 300000000     $FXCON  BSS 0                                                   1
000651  20600000  20600000      $FLCON  CON 0,20600000                                          1
000652  300000000 300000000     $STBRU  BSS 0                                                   1
000652  300000001 300000001     $TEMP   BSS 1                                                   1
000653  300000001 300000001     NCELL   BSS 1                                                   1
000654  300000001 300000001     CTABLE  BSS 1                                                   1
000655  300000001 300000001     NFCELL  BSS 1                                                   1
000656  300000001 300000001     ALPHA   BSS 1                                                   1
000657  300000001 300000001     PFCELL  BSS 1                                                   1
000660  300000001 300000001     C       BSS 1                                                   1
000661  300000001 300000001     RG      BSS 1                                                   1
000662  300000001 300000001     ST      BSS 1                                                   1
000663  300000001 300000001     CORR    BSS 1                                                   1

*                                                        1

*PROGRAM END.    0 FORTRAN ERRORS                         1
```

```
          •00000000   •00000000          END                                                    1
                                              0 ASSEMBLY ERRORS.
                                         000664 PROGRAM OCTAL SIZE.
                                         000314 EQL TABLE OCTAL SIZE.

103756 COMPILE
       814030060    814030060           IDN 000000                                              1
       814030060    814030060                                                                   1
                                        EQUIVALENCE(POPAC,OUTABL(1)),(YAR89,OUTABL(2)),(CYCLE,  7
                                       1FILEX (11)),(BH,   MPAR(5)),                            7
                                       1(TOPAC,OUTABL(3)),(XTRI,OUTABL(4)),(YTRI,OUTABL(5)),    7
                                       2(ZTRI,OUTABL(6)),(LH,OUTABL(7)),(AH,OUTABL(8)),         7
                                       3(BH,OUTABL(9)),(BRRINF,OUTABL(10))                      7
                                        INTEGER CYCLE                                           7
                                        REAL K,LNAX,KTABL,MPAR,LH                               7
                                        NX = 0                                                  7
000000    00001527    00041527          LDA SFXCON                                              1
000001    32001560    32041557          STA NX                                                  1
                                        DIMENSION TMPSAV (128)                                  7
                                        DIMENSION FILEX(0/11)                                   7
                                        DIMENSION RZTABL(0/7),TTABL(0/7),RITABL(0/7)            7
                                        DIMENSION STABL(0/7),KTABL(0/7),MPAR(0/6)               7
                                       1,STTABL(0/7,0/1),RGTABL(0/7,0/1),VTABL(0/7,0/1),SGTABL(0/7,0/1)7
                                       2,OUTABL(0/9),RSTABL(0/7,0/1)                            7
                                        GO TO 5                                                 7
000002    14000071    14040067          BRU $5                                                  1
                                      C GET TABLE OF SPECIFIC GRADE CORR. FACTORS FROM BULK TABLE. 7
                                        CALL GET TABLE (NX,TMPSAV,IRR)                          7
000003    33000514    33000514          SPB GETTAB                                              1
000004    07301560    07341554          LXK NX,3                                                1
000005    07301606    07341601          LXK TMPSAV,3                                            1
000006    07301561    07341553          LXK IRR,3                                               1
                                        IF (IRR) 11,20,11                                       7
000007    00001561    00041552          LDA IRR                                                 1
000010    05004727    05004727          TOD 23                                                  1
000011    34000015    34040004          BTS $11                                                 1
000012    05004670    05004670          TZE                                                     1

000013    34000032    34040017          BTS $20                                                 1
000014    14000015    14040001          BRU $11                                                 1
```

```
                                     11    PRINT (1)31
000015   40000023   40040006        $11    LDK $31                                                      7
000016   45004330   45004330               MAQ                                                          1
000017   00001530   00041511               LDA SFXCON+1                                                 1
000020   33000561   33000561               SPB $PRINT                                                   1
000021   33000564   33000564               SPB $HLOUT                                                   1
                                                                                                        1

31    FORMAT ($ OMOD DT $)                                        7
000022   14000030   14040006               BRU $MO                                                      1
000023   40110000   40110000        $31    CON 0,40110000                                               1
000024   10047515   10047515               CON A,3, OM                                                  1
000025   23642040   23642040               CON A,3,OD                                                   1
000026   21052040   21052040               CON A,3,DT                                                   1
000027   60077773   60077773               CON 0,60077773                                               1

STOP                                                         7
000030   33000405   33000405        $MO    SPB OFFC02                                                   1
000031   10000000   10000000               PRG 0,1,0,0,0                                                1

20    CONTINUE                                                     7
000032   300000000  300000000       $20    BSS 0                                                        1

C COPY PERM. CORE FILE AT /63200 INTO PROG. WORKING AREA AT FILEX1  7
000032   16301526   16341474               LDX FILADD,3                                                 6
000033   40000226   40000226               LDK 150                                                      6
000034   32000005   32000005               STA 5                                                        6
000035   00002023   00002023               LDA ZERO                                                     6
000036   32000004   32000004               STA 4                                                        6
000037   00300000   00300000        NOTDON LDA 0,3                                                      6
000040   32401102   32441042               STA FILEX1,4                                                 6
000041   26300001   26300001               INX 1,3                                                      6
000042   26400001   26400001               INX 1,4                                                      6
000043   06000005   06000005               DMT 5                                                        6
000044   34000037   34077773               BTS NOTDON                                                   6

*GET INC TO CONSTANT TABLE FROM OPERATOR ENTERED MOD.FILE          6
000045   16401331   16441264               LDX MOD,4                                                    6
000046   00400001   00400001               LDA 1,4                                                      6
000047   50000010   50000010               SKA 8              TEST FOR GRADE INCREMENT IN LIMITS        6
000050   05004727   05004727               TOD 23                                                       6
000051   30000054   30040003               BTR *+3                                                      6
000052   05000000   05000000               LDZ                                                          6
000053   14000055   14040002               BRU *+2                                                      6
000054   00400001   00400001               LDA 1,4                                                      6

*MULTIPLY BY 16 TO GET INCRIMENT                                   6
000055   05014047   05014047               SRA 7                                                        6

000056   32000004   32000004               STA 4                                                        6

C OVERLAY SPECIFIC GRADE CORR. FACTOR TABLE IN WORKING AREA        7

C AT FILEX1<76 WITH 16 WORD TABLE SELECTED BY OPERATOR ENTERED NO. 7
000057   00025177   00025177               LDA FIFTEN                                                   6
000060   32000003   32000003               STA 3                                                        6
000061   00002023   00002023               LDA ZERO                                                     6
000062   32000005   32000005               STA 5                                                        6
000063   00401606   00441523        RELOOP LDA TMPSAV,4                                                 6
000064   32501216   32541132               STA SGTABL,5                                                 6
000065   26400001   26400001               INX 1,4                                                      6
000066   26500001   26500001               INX 1,5                                                      6
000067   06000003   06000003               DMT 3                                                        6
000070   34000063   34077773               BTS RELOOP                                                   6

5     CONTINUE                                                     7
000071   300000000  300000000       $5     BSS 0                                                        1

C CHECK IF CYCLE(NO. OF FILTER WHEEL REV. REQUIRED FOR NEW CALC.)  7
                                     CHAS BEEN COUNTED DOWN TO ZERO BY PROG. 14.                       7
                                           IF(CYCLE)110,10,120                                          7
000071   00001114   00041023               LDA CYCLE                                                    1
000072   05004727   05004727               TOD 23                                                       1
000073   34000077   34040004               BTS $10                                                      1
000074   05004670   05004670               TZE                                                          1
000075   34000077   34040002               BTS $10                                                      1
000076   14001100   14041002               BRU $120                                                     1

C SET UP J>1 TO INDEX TRANS. PARAMETERS.                           7
                                     10    J=1                                                          7
000077   00001530   00041431        $10    LDA SFXCON+1                                                 7
000100   32001562   32041462               STA J                                                        1
```

Program Listing For Program Forty-Two (FIGS. 17-20)

The following listing is presented to illustrate the extent of the programming effort to implement the flow charts of FIGS. 17-20. It will be observed that the implementation of these flow charts together with the changes previously indicated herein and any necessary debugging is within the routine skill of the art.

```
                                            I=0                                                            7
000101    00001527    00041426              LDA $FXCON                                                     1
000102    32001563    32041461              STA I                                                          1

C LOAD TRANSMITTANCE SPECIFIC GRADE CORR. FOR ITH FILTER.              7

15   SGCF=SGTABL(I,J)                                              7
000103    00001562    00041457          $15 LDA J                                                          1
000104    45004330    45004330              MAQ                                                            1
000105    11001563    11041456              ADD I                                                          1
000106    55001531    55041423              MPY $FXCON+2                                                   1
000107    45006467    45006467              DLA 23                                                         1
000110    32001555    32041445              STA STEMP                                                      1

000111    16301555    16341444              LDX STEMP,3                                                    1
000112    00301216    00341104              LDA SGTABL,3                                                   1
000113    32001564    32041451              STA SGCF                                                       1

C LOAD DIFFUSOR TRANS. CONST. FROM RGTABL FOR ITH FILTER INTO TD.      7

TD=RGTABL(I,J)                                                 7
000114    00001562    00041446              LDA J                                                          1
000115    45004330    45004330              MAQ                                                            1
000116    11001563    11041445              ADD I                                                          1
000117    55001531    55041412              MPY $FXCON+2                                                   1
000120    45006467    45006467              DLA 23                                                         1
000121    32001555    32041434              STA STEMP                                                      1
000122    16401555    16441433              LDX STEMP,4                                                    1
000123    00401156    00441033              LDA RGTABL,4                                                   1
000124    32001565    32041441              STA TD                                                         1

C LOAD SMOOTHED AND STANDARDIZE CORRECTED TRANS. RATIO INTO TDP.       7

TDP=VTABL(I,J)                                                 7
000125    00001562    00041435              LDA J                                                          1
000126    45004330    45004330              MAQ                                                            1
000127    11001563    11041434              ADD I                                                          1
000130    55001531    55041401              MPY $FXCON+2                                                   1
000131    45006467    45006467              DLA 23                                                         1
000132    32001555    32041423              STA STEMP                                                      1
000133    16501555    16541422              LDX STEMP,5                                                    1
000134    00501176    00541042              LDA VTABL,5                                                    1
000135    32001566    32041431              STA TDP                                                        1

C CORRECT TDP FOR SPECIFIC GRADE.                                      7

TDP=TDP*SGCF                                                   7
000136    00001566    00041430              LDA TDP                                                        1
000137    72001564    72041425              FMP SGCF                                                       1
000140    32001566    32041426              STA TDP                                                        1

C SET UP J>0 FOR REFLECTANCE PARAMETERS.                               7

J=0                                                            7
000141    00001527    00041366              LDA $FXCON                                                     1
000142    32001562    32041420              STA J                                                          1

C LOAD BACKING PLATE REFLECTANCE FROM RGTABL INTO RG FOR ITH FILTER.   7

RG=RGTABL(I,J)                                                 7
000143    00001562    00041417              LDA J                                                          1
000144    45004330    45004330              MAQ                                                            1
000145    11001563    11041416              ADD I                                                          1
000146    55001531    55041363              MPY $FXCON+2                                                   1
```

```
000147  45006467  45006467         DLA 23
000150  32001555  32041405         STA STEMP
000151  16601555  16641404         LDX STEMP,6
000152  00601156  00641004         LDA RGTABL,6
000153  32001567  32041414         STA RG

C LOAD REFLECTANCE SPECIFIC GRADE CORR. FACTOR FOR ITH FILTER.

SGCF=SGTABL(I,J)
000154  00001562  00041406         LDA J
000155  45004330  45004330         MAQ
000156  11001563  11041405         ADD I
000157  55001531  55041352         MPY $FXCON+2
000160  45006467  45006467         DLA 23
000161  32001555  32041374         STA STEMP
000162  16301555  16341373         LDX STEMP,3
000163  00301216  00341033         LDA SGTABL,3
000164  32001564  32041400         STA SGCF

C LOAD SMOOTHED AND STANDARDIZE CORRECTED REFLEC. RATIO INTO R.

R=VTABL(I,J)
000165  00001562  00041375         LDA J
000166  45004330  45004330         MAQ
000167  11001563  11041374         ADD I
000170  55001531  55041341         MPY $FXCON+2
000171  45006467  45006467         DLA 23
000172  32001555  32041363         STA STEMP
000173  16401555  16441362         LDX STEMP,4
000174  00401176  00441002         LDA VTABL,4
000175  32001570  32041373         STA R

C CORRECT R FOR SPECIFIC GRADE.

R=R*SGCF
000176  00001570  00041372         LDA R
000177  72001564  72041365         FMP SGCF
000200  32001570  32041370         STA R

C CALC. RZERO FOR ITH FILTER.

RZERO=(R-RG*(TDP/TD)**2)/(1.-(RG*TDP/TD)**2)
000201  00001566  00041365         LDA TDP
000202  73001565  73041363         FDV TD
000203  32001555  32041352         STA STEMP
000204  00001567  00041363         LDA RG
000205  72001566  72041361         FMP TDP
000206  73001565  73041357         FDV TD
000207  32001556  32041347         STA STEMP+1
000210  00001532  00041322         LDA $FXCON+3
000211  74020027  74020027         FLO 23
000212  33002036  33041624         SPB XXXEXP
000213  00001556  00041343         LDA STEMP+1
000214  71001542  71041326         FSU $FLCON
000215  32001557  32041342         STA STEMP+2
000216  00001532  00041314         LDA $FXCON+3
000217  74020027  74020027         FLO 23
000220  33002036  33041616         SPB XXXEXP
000221  00001555  00041334         LDA STEMP
000222  72001567  72041345         FMP RG
000223  71001570  71041345         FSU R
000224  73001557  73041333         FDV STEMP+2
000225  32001571  32041344         STA RZERO

C CALC. TRANSMITTANCE T FOR ITH FILTER.

T=(TDP*(1.-RG*R))/(TD*(1.-(RG*TDP/TD)**2))
000226  00001567  00041341         LDA RG
000227  72001566  72041337         FMP TDP
000230  73001565  73041335         FDV TD
000231  32001555  32041324         STA STEMP
000232  00001532  00041300         LDA $FXCON+3
000233  74020027  74020027         FLO 23
000234  33002036  33041602         SPB XXXEXP
000235  00001555  00041320         LDA STEMP
000236  71001542  71041304         FSU $FLCON
000237  72001565  72041326         FMP TD
000240  32001556  32041316         STA STEMP+1
000241  00001567  00041326         LDA RG
000242  72001570  72041326         FMP R
000243  71001542  71041277         FSU $FLCON
000244  72001566  72041322         FMP TDP
000245  73001556  73041311         FDV STEMP+1
000246  32001572  32041324         STA T

C CALC. INTERM. VARIABLE AI

AI=(1.0*RZERO**2-T**2)/(2.0*RZERO)
000247  00001543  00041274         LDA $FLCON+1
000250  72001571  72041321         FMP RZERO
000251  32001555  32041304         STA STEMP
000252  00001532  00041260         LDA $FXCON+3
000253  74020027  74020027         FLO 23
000254  33002036  33041662         SPB XXXEXP
000255  00001571  00041314         LDA RZERO
000256  70001542  70041264         FAD $FLCON
000257  32001556  32041277         STA STEMP+1
000260  00001532  00041252         LDA $FXCON+3
```

| | | | | |
|---|---|---|---|---|
| 000261 | 74020027 | 74020027 | FLO 23 | 1 |
| 000262 | 33002036 | 33041554 | SPB XXXEXP | 1 |

| | | | | |
|---|---|---|---|---|
| 000263 | 00001572 | 00041307 | LDA T | 1 |
| 000264 | 71001556 | 71041272 | FSU STEMP+1 | 1 |
| 000265 | 73001555 | 73041270 | FDV STEMP | 1 |
| 000266 | 05004670 | 05004670 | TZE | 1 |
| 000267 | 34000271 | 34040002 | BTS *+2 | 1 |
| 000270 | 05047027 | 05047027 | CBK 23 | 1 |
| 000271 | 32001573 | 32041302 | STA AI | 1 |

C CALC. INTERM. VARIABLE BI  7

BI=SQRTF(AI**2-1)  7

| | | | | |
|---|---|---|---|---|
| 000272 | 00001532 | 00041240 | LDA SFXCON+3 | 1 |
| 000273 | 74020027 | 74020027 | FLO 23 | 1 |
| 000274 | 33002036 | 33041542 | SPB XXXEXP | 1 |
| 000275 | 00001573 | 00041276 | LDA AI | 1 |
| 000276 | 32001555 | 32041257 | STA STEMP | 1 |
| 000277 | 00001530 | 00041231 | LDA SFXCON+1 | 1 |
| 000300 | 74020027 | 74020027 | FLO 23 | 1 |
| 000301 | 71001555 | 71041254 | FSU STEMP | 1 |
| 000302 | 05004670 | 05004670 | TZE | 1 |
| 000303 | 34000305 | 34040002 | BTS *+2 | 1 |
| 000304 | 05047027 | 05047027 | CBK 23 | 1 |
| 000305 | 33002037 | 33041532 | SPB SQRTF | 1 |
| 000306 | 32001574 | 32041266 | STA BI | 1 |

C CALC. REFLECTANCE WITH INFINITE BACKING RINF>AI-BI  7

RINF=AI-BI  7

| | | | | |
|---|---|---|---|---|
| 000307 | 00001573 | 00041264 | LDA AI | 1 |
| 000310 | 71001574 | 71041264 | FSU BI | 1 |
| 000311 | 32001575 | 32041264 | STA RINF | 1 |

C CALC. ARG. OF LOG FUNCTION, AX  7

AX=(BI+SQRTF(BI*BI+T*T))/(T*(BI+AI))  7

| | | | | |
|---|---|---|---|---|
| 000312 | 00001574 | 00041262 | LDA BI | 1 |
| 000313 | 72001574 | 72041261 | FMP BI | 1 |
| 000314 | 32001555 | 32041241 | STA STEMP | 1 |
| 000315 | 00001572 | 00041255 | LDA T | 1 |
| 000316 | 72001572 | 72041254 | FMP T | 1 |
| 000317 | 70001555 | 70041236 | FAD STEMP | 1 |
| 000320 | 33002037 | 33041517 | SPB SQRTF | 1 |
| 000321 | 32001556 | 32041235 | STA STEMP+1 | 1 |
| 000322 | 00001574 | 00041252 | LDA BI | 1 |
| 000323 | 70001573 | 70041250 | FAD AI | 1 |
| 000324 | 72001572 | 72041246 | FMP T | 1 |
| 000325 | 32001557 | 32041232 | STA STEMP+2 | 1 |
| 000326 | 00001574 | 00041246 | LDA BI | 1 |
| 000327 | 70001556 | 70041227 | FAD STEMP+1 | 1 |
| 000330 | 73001557 | 73041227 | FDV STEMP+2 | 1 |
| 000331 | 32001576 | 32041245 | STA AX | 1 |

C CALC. NAT. LOG OF AX  7

LNAX=LOGF(AX)  7

| | | | | |
|---|---|---|---|---|
| 000332 | 00001576 | 00041244 | LDA AX | 1 |

| | | | | |
|---|---|---|---|---|
| 000333 | 33002040 | 33041505 | SPB LOGF | 1 |
| 000334 | 32001577 | 32041243 | STA LNAX | 1 |
| 000335 | 16601111 | 16640554 | LDX FILEX1+7,6 | 6 |
| 000336 | 00600001 | 00600001 | LDA 1,6 | 6 |
| 000337 | 74020010 | 74020010 | FLO 8 | 6 |
| 000340 | 32001314 | 32040754 | STA BW | 6 |

C CALC. SCATTER COEF S PER LB. BASIS WT.  7

S=LNAX/(BI*BW)  7

| | | | | |
|---|---|---|---|---|
| 000341 | 00001574 | 00041233 | LDA BI | 1 |
| 000342 | 72001314 | 72040752 | FMP BW | 1 |
| 000343 | 32001555 | 32041212 | STA STEMP | 1 |
| 000344 | 00001577 | 00041233 | LDA LNAX | 1 |
| 000345 | 73001555 | 73041210 | FDV STEMP | 1 |
| 000346 | 32001600 | 32041232 | STA S | 1 |

C CALC. ABSORPTION COEF. K PER LB. BASIS WT.  7

K=S*(AI-1.)  7

| | | | | |
|---|---|---|---|---|
| 000347 | 00001573 | 00041224 | LDA AI | 1 |
| 000350 | 71001542 | 71041172 | FSU SFLCON | 1 |
| 000351 | 72001600 | 72041227 | FMP S | 1 |
| 000352 | 32001601 | 32041227 | STA K | 1 |

C SAVE RZERO, T, RINF IN TEMPORARY ARRAYS.  7

RZTABL(I)=RZERO  7

| | | | | |
|---|---|---|---|---|
| 000353 | 00001571 | 00041216 | LDA RZERO | 1 |
| 000354 | 16501563 | 16541207 | LDX I,5 | 1 |
| 000355 | 32502006 | 32541431 | STA RZTABL,5 | 1 |

TTABL(I)=T  7

| | | | | |
|---|---|---|---|---|
| 000356 | 00001572 | 00041214 | LDA T | 1 |
| 000357 | 32502016 | 32541437 | STA TTABL,5 | 1 |

RITABL(I)=RINF  7

| | | | | |
|---|---|---|---|---|
| 000360 | 00001575 | 00041215 | LDA RINF | 1 |
| 000361 | 32502026 | 32541445 | STA RITABL,5 | 1 |

C SAVE S AND K IN FILEX1 TABLES  7

STABL(I)=S  7

| | | | | |
|---|---|---|---|---|
| 000362 | 00001600 | 00041216 | LDA S | 1 |
| 000363 | 32501250 | 32540665 | STA STABL,5 | 1 |

KTABL(I)=K  7

| | | | | |
|---|---|---|---|---|
| 000364 | 00001601 | 00041215 | LDA K | 1 |
| 000365 | 32501260 | 32540673 | STA KTABL,5 | 1 |

IF(I-6)30,60,60  7

| | | | | |
|---|---|---|---|---|
| 000366 | 00001563 | 00041175 | LDA I | 1 |
| 000367 | 31001533 | 31041144 | SUB SFXCON+4 | 1 |
| 000370 | 05004727 | 05004727 | TOD 23 | 1 |
| 000371 | 34000375 | 34040004 | BTS $30 | 1 |
| 000372 | 05004670 | 05004670 | TZE | 1 |
| 000373 | 34000403 | 34040010 | BTS $60 | 1 |
| 000374 | 14000403 | 14040007 | BRU $60 | 1 |

30  J=1  7

| | | | | |
|---|---|---|---|---|
| 000375 | 00001530 | 00041133 | $30 LDA SFXCON+1 | 1 |
| 000376 | 32001562 | 32041164 | STA J | 1 |

I=I+1  7

| | | | | |
|---|---|---|---|---|
| 000377 | 00001563 | 00041164 | LDA I | 1 |
| 000400 | 11001530 | 11041130 | ADD SFXCON+1 | 1 |
| 000401 | 32001563 | 32041162 | STA I | 1 |

GO TO 15  7

| | | | | |
|---|---|---|---|---|
| 000402 | 14000103 | 14077501 | BRU $15 | 1 |

C CALC DIFF. IN Z REFLECT. WITH AND WITHOUT FLUOR * MULT. BY IMP.CON. 7

60  ZFLUOR=(VTABL(6,0)-VTABL(3,0))*MPAR(0)  7

| | | | | |
|---|---|---|---|---|
| 000403 | 00001204 | 00040601 | $60 LDA VTABL+6 | 1 |
| 000404 | 71001201 | 71040575 | FSU VTABL+3 | 1 |
| 000405 | 72001310 | 72040703 | FMP MPAR | 1 |
| 000406 | 32001602 | 32041174 | STA ZFLUOR | 1 |

C ADD DIFF. TO RINF FOR Z FILTER WITHOUT FLUOR. TO GET Z WITH FLUOR. 7

ZRINF=RITABL(3)+ZFLUOR  7

| | | | | |
|---|---|---|---|---|
| 000407 | 00002031 | 00041422 | LDA RITABL+3 | 1 |

```
000410  70001602  70041172           FAD ZFLUOR                                                          1
000411  32001603  32041172           STA ZRINF                                                           1
                          C CALC. TRI STIM. XSUBB REFLECTANCE WITH FLUORECENCE BY ADDING                 7
                          C EMPIRICAL FRACT OF CHANGE IN Z REFL INPUTS DUE TO FLUOR                      7
                                  XBRINF=RITABL(1)+ZFLUOR*MPAR(1)                                        7
000412  00001602  00041170           LDA ZFLUOR                                                          1
000413  72001311  72040676           FMP MPAR+1                                                          1
000414  70002027  70041413           FAD RITABL+1                                                        1
```

```
                          C CALC. TAPPI OPACITY                                                          7
                                  TOPAC=RZTABL(5)/YAR89                                                  7
000442  00002013  00041351           LDA RZTABL+5                                                        1
000443  73001237  73040574           FDV YAR89                                                           1
000444  32001240  32040574           STA TOPAC                                                           1
                          C CALC. TRI-STIM X WITH XSUBB INCLUDING FLUOR.                                 7
                                  XTRI=.196*XBRINF+.784*RITABL(2)                                        7
000445  00001545  00041100           LDA $FLCON+3                                                        1
000446  72001604  72041136           FMP XBRINF                                                          1
```

```
000447  32001555  32041106           STA $TEMP                                                           1
000450  00001546  00041076           LDA $FLCON+4                                                        1
000451  72002030  72041357           FMP RITABL+2                                                        1
000452  70001555  70041103           FAD $TEMP                                                           1
000453  32001241  32040566           STA XTRI                                                            1
                          C CALC. TRI-STIM Y WITH ILLUM. C                                               7
                                  YTRI=RITABL(4)                                                         7
000454  00002032  00041356           LDA RITABL+4                                                        1
000455  32001242  32040565           STA YTRI                                                            1
000415  32001604  32041167           STA XBRINF                                                          1
                          C CALC BRIGHTNESS FILTER REFLECTANCE WITH FLUOR BY ADDING                      7
                          C EMPIRICAL FRACT OF CHANGEIN Z REFL INPUTS DUE T FLUOR.                       7
                                  BRRINF=RITABL(0)+ZFLUOR*MPAR(2)                                        7
000416  00001602  00041164           LDA ZFLUOR                                                          1
000417  72001312  72040673           FMP MPAR+2                                                          1
000420  70002026  70041406           FAD RITABL                                                          1
000421  32001247  32040626           STA BRRINF                                                          1
                          C CALC. PRINTING OPACITY AS RATIO OF RZERO/RINF FOR YSUBC FILTER.              7
                                  POPAC=RZTABL(4)/RITABL(4)                                              7
000422  00002012  00041370           LDA RZTABL+4                                                        1
000423  73002032  73041407           FDV RITABL+4                                                        1
000424  32001236  32040612           STA POPAC                                                           1
                          C CALC. TRI-STIM Y REFL. WITH ILLUM. A + .89 BACKING.                          7
                                  YAR89=RZTABL(5)+(.89*TTABL(5)*TTABL(5))                                7
                                  1/(1.-.89*RZTABL(5))                                                   7
000425  00001544  00041117           LDA $FLCON+2                                                        1
000426  72002013  72041365           FMP RZTABL+5                                                        1
000427  71001542  71041113           FSU $FLCON                                                          1
000430  32001555  32041125           STA $TEMP                                                           1
000431  00001544  00041113           LDA $FLCON+2                                                        1
000432  72002023  72041371           FMP TTABL+5                                                         1
000433  72002023  72041370           FMP TTABL+5                                                         1
000434  73001555  73041121           FDV $TEMP                                                           1
000435  71002013  71041356           FSU RZTABL+5                                                        1
000436  05004670  05004670           TZE                                                                 1
000437  34000441  34040002           BTS *+2                                                             1
000440  05047027  05047027           CBK 23                                                              1
000441  32001237  32040576           STA YAR89                                                           1
```

```
                              C CALC. TRI-STIM Z WITH FLUOR.                              7

ZTRI=1.18*ZRINF                                           7
000456  00001547  00041071     LDA $FLCON+5                                               1
000457  72001603  72041124     FMP ZRINF                                                  1
000460  32001243  32040563     STA ZTRI                                                   1

C CALC. HUNTER L COORD.                                     7

LH=100.0*SQRTF(YTRI)                                      7
000461  00001242  00040561     LDA YTRI                                                   1
000462  33002037  33041355     SPB SQRTF                                                  1
000463  32001555  32041072     STA $TEMP                                                  1
000464  00001550  00041064     LDA $FLCON+6                                               1
000465  72001555  72041070     FMP $TEMP                                                  1
000466  32001244  32040556     STA LH                                                     1

C CALC. HUNTER SMALL A                                      7

AH=175.*(1.02*XTRI-YTRI)/LH                               7
000467  00001552  00041063     LDA $FLCON+8                                               1
000470  72001241  72040551     FMP XTRI                                                   1
000471  71001242  71040551     FSU YTRI                                                   1
000472  72001551  72041057     FMP $FLCON+7                                               1
000473  73001244  73040551     FDV LH                                                     1
000474  32001245  32040551     STA AH                                                     1

C CALC. HUNTER SMALL B                                      7

BH=70.*(YTRI-.847*ZTRI)/LH                                7
000475  00001554  00041057     LDA $FLCON+10                                              1
000476  72001243  72040545     FMP ZTRI                                                   1
000477  71001242  71040543     FSU YTRI                                                   1
000500  72001553  72041053     FMP $FLCON+9                                               1
000501  73001244  73040543     FDV LH                                                     1
000502  05004670  05004670     TZE                                                        1
000503  34000505  34040002     BTS *+2                                                    1
000504  05047027  05047027     CBK 23                                                     1

000505  32001246  32040541     STA BH                                                     1

C RESET FILTER CYCLE SLOWDOWN INDEX TO INITIAL VALUE IN MPAR<3  7

CAND STORE IN PERM. CORE FILE AT /63200<10 BASE 10          7

FILEX(10)=MPAR(3)                                         7
000506  00001313  00040605     LDA MPAR+3                                                 1
000507  32001114  32040405     STA FILEX+10                                               1

CONTINUE                                                  7
000510  16301526  16341016     LDX FILADD,3         SAVE WORKING CYCLE COUNT IN PERM CORE 6
000511  00001114  00040403     LDA FILEX1+10                                              6
000512  32300012  32300012     STA 10,3                                                   6

PRINT 600,(RZTABL(M),M=0,7)                               7
000513  40000756  40040243     LDK $600                                                   1
000514  45004330  45004330     MAQ                                                        1
000515  33000561  33000561     SPB $PRINT                                                 1
000516  00001527  00041011     LDA $FXCON                                                 1
000517  32001605  32041066     STA M                                                      1
000520  16601605  16641065  $M1 LDX M,6                                                   1
000521  40602006  40641265     LDK RZTABL,6                                               1
000522  32001555  32041033     STA $TEMP                                                  1
000523  33000563  33000563     SPB $OUTRP                                                 1
000524  16701555  16741031     LDX $TEMP,7                                                1
000525  05003000  05003000     LDO 0                                                      1
000526  11001605  11041057     ADD M                                                      1
000527  32001605  32041056     STA M                                                      1
000530  31001540  31041010     SUB $FXCON+9                                               1
000531  05004670  05004670     TZE                                                        1
000532  05004527  05004527     SOD 23                                                     1
000533  34000520  34077765     BTS $M1                                                    1
000534  33000564  33000564     SPB $HLOUT                                                 1

PRINT 600,(TTABL(M),M=0,7)                                7
000535  40000756  40040221     LDK $600                                                   1
000536  45004330  45004330     MAQ                                                        1
000537  33000561  33000561     SPB $PRINT                                                 1
000540  00001527  00040767     LDA $FXCON                                                 1
000541  32001605  32041044     STA M                                                      1
000542  16301605  16341043  $M2 LDX M,3                                                   1
000543  40302016  40341253     LDK TTABL,3                                                1
000544  32001555  32041011     STA $TEMP                                                  1
000545  33000563  33000563     SPB $OUTRP                                                 1
000546  16701555  16741007     LDX $TEMP,7                                                1
000547  05003000  05003000     LDO 0                                                      1
000550  11001605  11041035     ADD M                                                      1
000551  32001605  32041034     STA M                                                      1
000552  31001540  31040766     SUB $FXCON+9                                               1
```

| | | | | | |
|---|---|---|---|---|---|
| 000553 | 05004670 | 05004670 | | TZE | 1 |
| 000554 | 05004527 | 05004527 | | SOD 23 | 1 |
| 000555 | 34000542 | 34077765 | | BTS SM2 | 1 |
| 000556 | 33000564 | 33000564 | | SPB SHLOUT | 1 |

PRINT 600,(RITABL(M),M=0,7)    7

| | | | | | |
|---|---|---|---|---|---|
| 000557 | 40000756 | 40040177 | | LDK $600 | 1 |
| 000560 | 45004330 | 45004330 | | MAQ | 1 |
| 000561 | 33000561 | 33000561 | | SPB SPRINT | 1 |
| 000562 | 00001527 | 00040745 | | LDA SFXCON | 1 |
| 000563 | 32001605 | 32041022 | | STA M | 1 |
| 000564 | 16401605 | 16441021 | SM3 | LDX M,4 | 1 |
| 000565 | 40402026 | 40441241 | | LDK RITABL,4 | 1 |
| 000566 | 32001555 | 32040767 | | STA STEMP | 1 |
| 000567 | 33000563 | 33000563 | | SPB SOUTRP | 1 |
| 000570 | 16701555 | 16740765 | | LDX STEMP,7 | 1 |
| 000571 | 05003000 | 05003000 | | LDO 0 | 1 |
| 000572 | 11001605 | 11041013 | | ADD M | 1 |
| 000573 | 32001605 | 32041012 | | STA M | 1 |
| 000574 | 31001540 | 31040744 | | SUB SFXCON+9 | 1 |
| 000575 | 05004670 | 05004670 | | TZE | 1 |
| 000576 | 05004527 | 05004527 | | SOD 23 | 1 |
| 000577 | 34000564 | 34077765 | | BTS SM3 | 1 |
| 000600 | 33000564 | 33000564 | | SPB SHLOUT | 1 |

PRINT 600,(STABL(M),M=0,7)    7

| | | | | | |
|---|---|---|---|---|---|
| 000601 | 40000756 | 40040155 | | LDK $600 | 1 |
| 000602 | 45004330 | 45004330 | | MAQ | 1 |
| 000603 | 33000561 | 33000561 | | SPB SPRINT | 1 |
| 000604 | 00001527 | 00040723 | | LDA SFXCON | 1 |
| 000605 | 32001605 | 32041000 | | STA M | 1 |
| 000606 | 16501605 | 16540777 | SM4 | LDX M,5 | 1 |
| 000607 | 40501250 | 40540441 | | LDK STABL,5 | 1 |
| 000610 | 32001555 | 32040745 | | STA STEMP | 1 |
| 000611 | 33000563 | 33000563 | | SPB SOUTRP | 1 |
| 000612 | 16701555 | 16740743 | | LDX STEMP,7 | 1 |
| 000613 | 05003000 | 05003000 | | LDO 0 | 1 |
| 000614 | 11001605 | 11040771 | | ADD M | 1 |
| 000615 | 32001605 | 32040770 | | STA M | 1 |
| 000616 | 31001540 | 31040722 | | SUB SFXCON+9 | 1 |
| 000617 | 05004670 | 05004670 | | TZE | 1 |
| 000620 | 05004527 | 05004527 | | SOD 23 | 1 |
| 000621 | 34000606 | 34077765 | | BTS SM4 | 1 |
| 000622 | 33000564 | 33000564 | | SPB SHLOUT | 1 |

PRINT 600,(KTABL(M),M=0,7)    7

| | | | | | |
|---|---|---|---|---|---|
| 000623 | 40000756 | 40040133 | | LDK $600 | 1 |
| 000624 | 45004330 | 45004330 | | MAQ | 1 |
| 000625 | 33000561 | 33000561 | | SPB SPRINT | 1 |
| 000626 | 00001527 | 00040701 | | LDA SFXCON | 1 |
| 000627 | 32001605 | 32040756 | | STA M | 1 |
| 000630 | 16601605 | 16640755 | SM5 | LDX M,6 | 1 |
| 000631 | 40601260 | 40640427 | | LDK KTABL,6 | 1 |
| 000632 | 32001555 | 32040723 | | STA STEMP | 1 |
| 000633 | 33000563 | 33000563 | | SPB SOUTRP | 1 |
| 000634 | 16701555 | 16740721 | | LDX STEMP,7 | 1 |
| 000635 | 05003000 | 05003000 | | LDO 0 | 1 |
| 000636 | 11001605 | 11040747 | | ADD M | 1 |
| 000637 | 32001605 | 32040746 | | STA M | 1 |
| 000640 | 31001540 | 31040700 | | SUB SFXCON+9 | 1 |
| 000641 | 05004670 | 05004670 | | TZE | 1 |
| 000642 | 05004527 | 05004527 | | SOD 23 | 1 |
| 000643 | 34000630 | 34077765 | | BTS SM5 | 1 |
| 000644 | 33000564 | 33000564 | | SPB SHLOUT | 1 |

PRINT 600,(STTABL(M,0),M=0,7)    7

| | | | | | |
|---|---|---|---|---|---|
| 000645 | 40000756 | 40040111 | | LDK $600 | 1 |
| 000646 | 45004330 | 45004330 | | MAQ | 1 |
| 000647 | 33000561 | 33000561 | | SPB SPRINT | 1 |
| 000650 | 00001527 | 00040657 | | LDA SFXCON | 1 |
| 000651 | 32001605 | 32040734 | | STA M | 1 |
| 000652 | 16301605 | 16340733 | SM6 | LDX M,3 | 1 |
| 000653 | 40301136 | 40340263 | | LDK STTABL,3 | 1 |
| 000654 | 32001555 | 32040701 | | STA STEMP | 1 |
| 000655 | 33000563 | 33000563 | | SPB SOUTRP | 1 |
| 000656 | 16701555 | 16740677 | | LDX STEMP,7 | 1 |

| | | | | | |
|---|---|---|---|---|---|
| 000657 | 05003000 | 05003000 | | LDO 0 | 1 |
| 000660 | 11001605 | 11040725 | | ADD M | 1 |
| 000661 | 32001605 | 32040724 | | STA M | 1 |
| 000662 | 31001540 | 31040656 | | SUB SFXCON+9 | 1 |
| 000663 | 05004670 | 05004670 | | TZE | 1 |
| 000664 | 05004527 | 05004527 | | SOD 23 | 1 |
| 000665 | 34000652 | 34077765 | | BTS SM6 | 1 |
| 000666 | 33000564 | 33000564 | | SPB SHLOUT | 1 |
| | | | | PRINT 600,(STTABL(M,1),M=0,7) | 7 |
| 000667 | 40000756 | 40040067 | | LDK $600 | 1 |
| 000670 | 45004330 | 45004330 | | MAQ | 1 |
| 000671 | 33000561 | 33000561 | | SPB SPRINT | 1 |
| 000672 | 00001527 | 00040635 | | LDA SFXCON | 1 |
| 000673 | 32001605 | 32040712 | | STA M | 1 |
| 000674 | 16401605 | 16440711 | SM7 | LDX M,4 | 1 |
| 000675 | 40401146 | 40440251 | | LDK STTABL+8,4 | 1 |
| 000676 | 32001555 | 32040657 | | STA STEMP | 1 |
| 000677 | 33000563 | 33000563 | | SPB SOUTRP | 1 |
| 000700 | 16701555 | 16740655 | | LDX STEMP,7 | 1 |
| 000701 | 05003000 | 05003000 | | LDO 0 | 1 |
| 000702 | 11001605 | 11040703 | | ADD M | 1 |
| 000703 | 32001605 | 32040702 | | STA M | 1 |
| 000704 | 31001540 | 31040634 | | SUB SFXCON+9 | 1 |
| 000705 | 05004670 | 05004670 | | TZE | 1 |
| 000706 | 05004527 | 05004527 | | SOD 23 | 1 |
| 000707 | 34000624 | 34077765 | | BTS SM7 | 1 |
| 000710 | 33000564 | 33000564 | | SPB SHLOUT | 1 |
| | | | | PRINT 600,(RGTABL(M,0),M=0,7) | 7 |
| 000711 | 40000756 | 40040045 | | LDK $600 | 1 |
| 000712 | 45004330 | 45004330 | | MAQ | 1 |
| 000713 | 33000561 | 33000561 | | SPB SPRINT | 1 |
| 000714 | 00001527 | 00040613 | | LDA SFXCON | 1 |
| 000715 | 32001605 | 32040670 | | STA M | 1 |
| 000716 | 16501605 | 16540667 | SM8 | LDX M,5 | 1 |
| 000717 | 40501156 | 40540237 | | LDK RGTABL,5 | 1 |
| 000720 | 32001555 | 32040635 | | STA STEMP | 1 |
| 000721 | 33000563 | 33000563 | | SPB SOUTRP | 1 |
| 000722 | 16701555 | 16740633 | | LDX STEMP,7 | 1 |
| 000723 | 05003000 | 05003000 | | LDO 0 | 1 |
| 000724 | 11001605 | 11040661 | | ADD M | 1 |
| 000725 | 32001605 | 32040660 | | STA M | 1 |
| 000726 | 31001540 | 31040612 | | SUB SFXCON+9 | 1 |
| 000727 | 05004670 | 05004670 | | TZE | 1 |
| 000730 | 05004527 | 05004527 | | SOD 23 | 1 |
| 000731 | 34000716 | 34077765 | | BTS SM8 | 1 |
| 000732 | 33000564 | 33000564 | | SPB SHLOUT | 1 |
| | | | | PRINT 600,(RGTABL(M,1),M=0,7) | 7 |
| 000733 | 40000756 | 40040023 | | LDK $600 | 1 |
| 000734 | 45004330 | 45004330 | | MAQ | 1 |
| 000735 | 33000561 | 33000561 | | SPB SPRINT | 1 |
| 000736 | 00001527 | 00040571 | | LDA SFXCON | 1 |
| 000737 | 32001605 | 32040646 | | STA M | 1 |
| 000740 | 16601605 | 16640645 | SM9 | LDX M,6 | 1 |
| 000741 | 40601166 | 40640225 | | LDK RGTABL+8,6 | 1 |
| 000742 | 32001555 | 32040613 | | STA STEMP | 1 |
| 000743 | 33000563 | 33000563 | | SPB SOUTRP | 1 |
| 000744 | 16701555 | 16740611 | | LDX STEMP,7 | 1 |
| 000745 | 05003000 | 05003000 | | LDO 0 | 1 |
| 000746 | 11001605 | 11040637 | | ADD M | 1 |
| 000747 | 32001605 | 32040636 | | STA M | 1 |
| 000750 | 31001540 | 31040570 | | SUB SFXCON+9 | 1 |
| 000751 | 05004670 | 05004670 | | TZE | 1 |
| 000752 | 05004527 | 05004527 | | SOD 23 | 1 |
| 000753 | 34000740 | 34077765 | | BTS SM9 | 1 |
| 000754 | 33000564 | 33000564 | | SPB SHLOUT | 1 |
| | | | 600 | FORMAT(8F10.5) | 7 |
| 000755 | 14000760 | 14040003 | | BRU SM10 | |
| 000756 | 02470056 | 02470056 | $600 | CON 0,02470056 | 1 |
| 000757 | 60077776 | 60077776 | | CON 0,60077776 | 1 |
| | | | | PRINT 600,(VTABL(M,0),M=0,7) | 7 |
| 000760 | 40000756 | 40077776 | SM10 | LDK $600 | 1 |
| 000761 | 45004330 | 45004330 | | MAQ | 1 |
| 000762 | 33000561 | 33000561 | | SPB SPRINT | 1 |

```
000763  00001527  00040544           LDA  SFXCON
000764  32001605  32040621           STA  M
000765  16301605  16340620    SM11   LDX  M,3
000766  40301176  40340210           LDK  VTABL,3
000767  32001555  32040566           STA  STEMP
000770  33000563  33000563           SPB  SOUTRP
000771  16701555  16740564           LDX  STEMP,7
000772  05003000  05003000           LDO  0
000773  11001605  11040612           ADD  M
000774  32001605  32040611           STA  M
000775  31001540  31040543           SUB  SFXCON+9
000776  05004670  05004670           TZE
000777  05004527  05004527           SOD  23
001000  34000765  34077765           BTS  SM11
001001  33000564  33000564           SPB  SHLOUT

PRINT 600,(VTABL(M,1),M=0,7)
001002  40000756  40077754           LDK  $600
001003  45004330  45004330           MAQ
001004  33000561  33000561           SPB  SPRINT
001005  00001527  00040522           LDA  SFXCON
001006  32001605  32040521           STA  M
001007  16401605  16440576    SM12   LDX  M,4
001010  40401206  40440176           LDK  VTABL+8,4
001011  32001555  32040544           STA  STEMP
001012  33000563  33000563           SPB  SOUTRP
001013  16701555  16740542           LDX  STEMP,7
001014  05003000  05003000           LDO  0
001015  11001605  11040570           ADD  M
001016  32001605  32040567           STA  M
001017  31001540  31040521           SUB  SFXCON+9
001020  05004670  05004670           TZE
001021  05004527  05004527           SOD  23
001022  34001007  34077765           BTS  SM12
001023  33000564  33000564           SPB  SHLOUT

PRINT 700,(MPAR(M),M=0,6)
001024  40001047  40040023           LDK  $700
001025  45004330  45004330           MAQ
001026  33000561  33000561           SPB  SPRINT
001027  00001527  00040500           LDA  SFXCON
001030  32001605  32040555           STA  M
001031  16501605  16540554    SM13   LDX  M,5
001032  40501310  40540256           LDK  MPAR,5
001033  32001555  32040522           STA  STEMP
001034  33000563  33000563           SPB  SOUTRP
001035  16701555  16740520           LDX  STEMP,7
001036  05003000  05003000           LDO  0
001037  11001605  11040546           ADD  M
001040  32001605  32040545           STA  M
001041  31001533  31040477           SUB  SFXCON+4
001042  05004670  05004670           TZE
001043  05004527  05004527           SOD  23
001044  34001031  34077765           BTS  SM13
001045  33000564  33000564           SPB  SHLOUT

700    FORMAT(3F10.5,I10,3F10.5)
001046  14001053  14040005           BRU  SM14
001047  02420056  02420056    $700   CON  0,02420056
001050  22401602  22401602           CON  0,22401602
001051  02420056  02420056           CON  0,02420056
001052  60077774  60077774           CON  0,60077774

PRINT 500,(OUTABL(M),M=0,9)
001053  40001076  40040023    SM14   LDK  $500
001054  45004330  45004330           MAQ
001055  33000561  33000561           SPB  SPRINT
001056  00001527  00040451           LDA  SFXCON
001057  32001605  32040526           STA  M
001060  16601605  16640525    SM15   LDX  M,6
001061  40601236  40640155           LDK  OUTABL,6
001062  32001555  32040473           STA  STEMP
001063  33000563  33000563           SPB  SOUTRP
001064  16701555  16740471           LDX  STEMP,7
001065  05003000  05003000           LDO  0
001066  11001605  11040517           ADD  M
001067  32001605  32040516           STA  M
001070  31001541  31040451           SUB  SFXCON+10
001071  05004670  05004670           TZE
001072  05004527  05004527           SOD  23
001073  34001060  34077765           BTS  SM15
001074  33000564  33000564           SPB  SHLOUT

500    FORMAT(10F10.5)
001075  14001100  14040003           BRU  SM16
001076  02510056  02510056    $500   CON  0,02510056
001077  60077776  60077776           CON  0,60077776

120    CONTINUE
001100  300000000  300000000  SM16   BSS  0
001100  300000000  300000000  $120   BSS  0

C TURN PROG. 42 OFF. WILL BE TURNED ON BY PROG. 14
                                     STOP
001100  33000405  33000405           SPB  OFFC02
```

```
001101  10000000   10000000              PRG 0,1,0,0,0                    1
001102  300000014  300000014     FILEX1  BSS 12                           6
001116  300000020  300000020     CTABL1  BSS 16                           6
001136  300000020  300000020     STTAB1  BSS 16                           6
001156  300000020  300000020     RGTAB1  BSS 16                           6
001176  300000020  300000020     VTABL1  BSS 16                           6
001216  300000020  300000020     SGTAB1  BSS 16                           6
001236  300000012  300000012     OUTAB1  BSS 10                           6
001250  300000010  300000010     STABL1  BSS 8                            6
001260  300000010  300000010     KTABL1  BSS 8                            6
001270  300000020  300000020     RSTAB1  BSS 16                           6
001310  300000020  300000020     MPAR1   BSS 16                           6
001330  00070632   00070632      BWPFA   CON 0,70632                      6
001331  00073261   00073261      MOD     CON 0,73261                      6
                                 CON     EQL *                            6
001332  300000174  300000174             BSS 124                          6
001526  00063200   00063200      FILADD  CON 0,63200                      6
                                         DEFINE CTABL(CTABL1),FILEX(FILEX1)   7
                                 CTABL   EQL CTABL1                       1
                                 FILEX   EQL FILEX1                       1
                                         DEFINE STTABL(STTAB1),RGTABL(RGTAB1)  7
                                         1,VTABL(VTABL1),SGTABL(SGTAB1),OUTABL(OUTAB1),STABL(STABL1),  7
                                         2KTABL(KTABL1),RSTABL(RSTAB1)    7
                                 STTABL  EQL STTAB1                       1
                                 RGTABL  EQL RGTAB1                       1
                                 VTABL   EQL VTABL1                       1
                                 SGTABL  EQL SGTAB1                       1
                                 OUTABL  EQL OUTAB1                       1
                                 STABL   EQL STABL1                       1
                                 KTABL   EQL KTABL1                       1
                                 RSTABL  EQL RSTAB1                       1
                                         DEFINE MPAR(MPAR1)               7
                                 MPAR    EQL MPAR1                        1
                                         END                              7
001527  300000000  300000000             BSS 0                            1
001527  00000000   00000000      $FXCON  CON 0,00000000                   1
001530  00000001   00000001              CON 0,00000001                   1
001531  00000010   00000010              CON 0,00000010                   1
001532  00000002   00000002              CON 0,00000002                   1
001533  00000006   00000006              CON 0,00000006                   1
001534  00000003   00000003              CON 0,00000003                   1
001535  00000004   00000004              CON 0,00000004                   1
001536  00000005   00000005              CON 0,00000005                   1
001537  00000012   00000012              CON 0,00000012                   1

001540  00000007   00000007              CON 0,00000007                   1
001541  00000011   00000011              CON 0,00000011                   1
001542  20600000   20600000      $FLCON  CON 0,20600000                   1
001543  21200000   21200000              CON 0,21200000                   1
001544  20343656   20343656              CON 0,20343656                   1
001545  17310550   17310550              CON 0,17310550                   1
001546  20310550   20310550              CON 0,20310550                   1
001547  20627024   20627024              CON 0,20627024                   1
001550  23710000   23710000              CON 0,23710000                   1
001551  24257000   24257000              CON 0,24257000                   1
001552  20602437   20602437              CON 0,20602437                   1
001553  23614000   23614000              CON 0,23614000                   1
001554  20330652   20330652              CON 0,20330652                   1
                                 $STBRU  BSS 0                            1
001555  300000003  300000003     $TEMP   BSS 3                            1
                                 POPAC   EQL OUTABL                       1
                                 YAR89   EQL OUTABL+1                     1
                                 CYCLE   EQL FILEX+10                     1
                                 BW      EQL MPAR+4                       1
                                 TOPAC   EQL OUTABL+2                     1
                                 XTRI    EQL OUTABL+3                     1
```

|        |           |           | YTRI   | EOL OUTABL+4 | 1 |
|--------|-----------|-----------|--------|--------------|---|
|        |           |           | ZTRI   | EOL OUTABL+5 | 1 |
|        |           |           | LH     | EOL OUTABL+6 | 1 |
|        |           |           | AH     | EOL OUTABL+7 | 1 |
|        |           |           | BH     | EOL OUTABL+8 | 1 |
|        |           |           | BRRINF | EOL OUTABL+9 | 1 |
| 001560 | 300000001 | 300000001 | NX     | BSS 1        | 1 |
| 001561 | 300000001 | 300000001 | IRR    | BSS 1        | 1 |
| 001562 | 300000001 | 300000001 | J      | BSS 1        | 1 |
| 001563 | 300000001 | 300000001 | I      | BSS 1        | 1 |
| 001564 | 300000001 | 300000001 | SGCF   | BSS 1        | 1 |
| 001565 | 300000001 | 300000001 | TD     | BSS 1        | 1 |
| 001566 | 300000001 | 300000001 | TDP    | BSS 1        | 1 |
| 001567 | 300000001 | 300000001 | RG     | BSS 1        | 1 |
| 001570 | 300000001 | 300000001 | R      | BSS 1        | 1 |
| 001571 | 300000001 | 300000001 | RZERO  | BSS 1        | 1 |
| 001572 | 300000001 | 300000001 | T      | BSS 1        | 1 |
| 001573 | 300000001 | 300000001 | AI     | BSS 1        | 1 |
| 001574 | 300000001 | 300000001 | BI     | BSS 1        | 1 |
| 001575 | 300000001 | 300000001 | RINF   | BSS 1        | 1 |
| 001576 | 300000001 | 300000001 | AX     | BSS 1        | 1 |
| 001577 | 300000001 | 300000001 | LN4X   | BSS 1        | 1 |
| 001600 | 300000001 | 300000001 | S      | BSS 1        | 1 |
| 001601 | 300000001 | 300000001 | K      | BSS 1        | 1 |
| 001602 | 300000001 | 300000001 | ZFLUOR | BSS 1        | 1 |
| 001603 | 300000001 | 300000001 | ZRINF  | BSS 1        | 1 |
| 001604 | 300000001 | 300000001 | XBRINF | BSS 1        | 1 |
| 001605 | 300000001 | 300000001 | M      | BSS 1        | 1 |
| 001606 | 300000200 | 300000200 | TMPSAV | BSS 128      | 1 |

| 002006 | 300000010 | 300000010 | RZTABL | BSS 8 | 1 |
|--------|-----------|-----------|--------|-------|---|
| 002016 | 300000010 | 300000010 | TTABL  | BSS 8 | 1 |
| 002026 | 300000010 | 300000010 | RITABL | BSS 8 | 1 |
| 002036 | 926054130 | 926054130 | XXXEXP | LIB   | 1 |
|        | 921254120 | 921254120 |        |       | 1 |
| 002037 | 924650522 | 924650522 | SORTF  | LIB   | 1 |
|        | 925043040 | 925043040 |        |       | 1 |
| 002040 | 923047507 | 923047507 | LOGF   | LIB   | 1 |
|        | 921420040 | 921420040 |        |       | 1 |

|          |           |           | *PROGRAM END. | 0 FORTRAN ERRORS | 1 |
|----------|-----------|-----------|---------------|------------------|---|
|          | *00000000 | *00000000 |               | END              | 1 |
|          |           |           |               | 0 ASSEMBLY ERRORS. |  |
|          |           |           |   002342 PROGRAM OCTAL SIZE. | | |
|          |           |           |   000470 EQL TABLE OCTAL SIZE. | | |

Proposed Optical Control Strategy

While the on-line automatic control of paper optical properties is an ultimate objective of the work reported herein, the claimed subject matter relates to on-machine monitoring of paper optical properties whether used as an aid to conventional manual control or for other purposes. Nevertheless, in order to provide a disclosure of the best mode presently contemplated for automatic control as a separate but related area of endeavor, the following discussion is presented.

The optical properties of a sheet of paper are dependent upon all of the materials of which it is made but primarily upon the furnished pulp, fillers, pigments, dyes, and some additives. It is often very difficult to maintain the optical attributes of the pulp, fillers and additives constant within a given production run. Such variation is even greater between runs. The optical properties of the finished paper may, however, be reasonably controlled to specified standards by varying the additions of dyes and fillers and pigments until the desired compensations are achieved. The problem is that each furnished ingredient affects each of the resulting paper optical properties in a rather complicated manner. Indeed the intuition of experienced papermakers has essentially been the sole method of optical property control. Unfortunately, this approach is inefficient, resulting in considerable off-standard paper and/or waste of costly materials. Accordingly, a dire need exists within the paper industry for a highly reliable and continuous optical property monitor coupled with a closed loop computer control system.

The value of such closed loop control, based on a feedback color detector, has already been demonstrated for the continuous addition of two and sometimes three dyes. (1) (2) Target dye concentrations changes of up to three dyes can be determined by solving three simultaneous equations containing three unknowns. (1) One disadvantage of such control is that accurate color monitoring is not presently available unless large and frequent empirically determined correction factors are applied to the original output results. A second disadvantage arises when opacity and the fluorescence must also be simultaneously controlled. In this case the number of independently controlled continuous additions increases from three to five. An optical brightener and an opacifying pigment constitute the two additional factors.

An object of this invention is to demonstrate a method by which fluorescence can be continuously monitored. A means by which the optical brightener addition can be separately and independently controlled is inherently implied. The paper color is also analyzed without the fluorescent contribution. It is, of course, this latter characterization (without fluorescence) which should be, but which has not in the past been, used to determine the required addition of the conventional dyes. In other words, the effect of the optical brightener is decoupled from the three conventional dyes making possible the simultaneous control of all four dyes.

Another portion of this invention demonstrates a means of continuously determining the scattering coefficient of the moving web for each of the six available light spectrums. It is possible to determine the scattering coefficient required to achieve a given opacity specification whenever the basis weight and absorption coefficient are known. When the latter are set equal to a given set of product specifications, then the calculated scattering coefficient becomes the target scattering coefficient. (The absorption coefficient can be acquired by off-line testing of a sample of the standard color to be matched. In reality, this becomes a target absorption coefficient as well.) The dyes have little, if any, effect on the scattering coefficient but the effect of the slurry pigment is very large. Thus the target scattering coefficient is used as the sole feedback variable to control the slurry pigment feed. This will insure that the opacity is at or near the specification as long, as the absorption coefficient and basis weight are also on target. The absorption coefficient should, of course, be on target by virtue of the independent color control. A completely independent system controls the basis weight.

A method by which the decoupling of three conventional dyes, one optical brightener and one opacifying pigment has hereby been explained. Heretofore, such decoupling as revealed in the prior art has been limited to three absorptive dyes and thereby neglecting the need to also achieve a specified degree of fluorescence and opacity.

References

1. The development of dynamic color control on a paper machine by H. Chao and W. Wickstrom; Automatica, Vol. 6 PP 5-18, Pergamon Press, 1970.
2. Another consideration for color and formation by Henry H. Chao and Warren A. Wickstrom, color engineering, Sept/Oct. 1971.

General Discussion of the Invention Particularly in Relation to an On-Machine System The present invention is for the purpose of obtaining a quantitative measure of an optical property such as brightness, color, opacity and fluorescence of single thickness sheet material.

The sheet material is substantially homogeneous in its thickness dimension such that the optical property of interest can be reliably calculated from reflectance and transmittance measurements on the basis of existing theory. Thus the present invention is not applicable to the sensing of localized surface effects (such as due to surface migration of light absorbing powder particles, for example). To the contrary the present invention is concerned with the average or bulk optical characteristics of the sheet material considered as a whole, and especially is concerned with the characteristics of paper sheet material as it is delivered from a paper machine after completion of the paper manufacturing process.

The present invention in its broader aspect does not require strictly homogeneous material since empirical correction factors can be applied for cases where theory is less effective. For example, the paper optical properties of calendered and coated papers may be effectively measured by the system of the present invention using grade correction factors to correlate on-machine results with the measurements obtained by standard off-line instruments.

The optical system of the monitoring device includes components such as those shown in FIG. 3 which define or optically affect the incident, reflected and transmitted light paths such as indicated at 133, 137 and 141–143 in FIG. 3. For the case of a filter wheel as indicated in FIG. 4, each filter wheel position may be considered to define a separate light energy path with its own predetermined spectral response characteristics.

In each filter wheel position, there are two distinct light energy paths for measuring a reflectance value and a transmittance value, respectively. In the illustrated embodiment each such light energy path includes a common incident light path 133, but the paths diverge, one coinciding with the reflectance sensing light path 137 and the other including the transmittance sensing light path. The photometric sensors 203 and 260 thus provide simultaneous reflectance and transmittance output signals with respect to essentially a common region of the web. The reflectance sensing light path collects light from a circular region with a diameter of about 3/16 inch, and the transmittance sensing light path collects light from a total elliptical region which includes substantially the same circular region as mentioned above. Because of sheet formation effects and other localized variations in web characteristics it is considered valuable that the reflectance and transmittance output signals are based on readings from essentially a common region of the web.

By taking at least one reading in each traverse of the web, and taking such readings at different points along the width in successive traverses, it is considered that accuracies equal to or superior to those of an off-line sampling of a finished reel can be achieved, while at the same time the readings are available immediately instead of after completion of a manufacturing run.

By way of example, in the illustrated system a traversal of the web by the sensing head takes about forty-five seconds, so that the sensing head operates at a rate of at least one traversal of the width of the web per minute in the time intervals between the hourly off-sheet standardizing operations.

In accordance with the teachings of the present invention, the optical window 135 is itself selected as to its optical characteristics so as to provide the basis for off-sheet standardization. To this end to is advantageous that the optical window exhibit an absolute reflectance value as measured by the standard automatic color-brightness tester of at least about thirty-five percent (35%). The corresponding absolute transmittance value as measured on the G.E. Recording Spectrophotometer with conventional optics is about fifty-six percent (56%). With the illustrated embodiment, once the system is properly adjusted with respect to the zero reflectance readings (as by the use of a black sheet of known minimal reflectance) the system maintains such zero adjustment quite stably; accordingly the higher the reflectance value of the optical window, the more effective is the reflectance standardization by means of the optical window. On the other hand a transmittance value which is of a reasonable magnitude is also desirable, so that the provision of an optical window that substantial values of absolute reflectance and transmittance is advantageous.

With the illustrated embodiment, the transmittance readings for the moving web are relatively more nearly independent of misalignment of the upper and lower sensing heads than the reflectance readings. Further it is considered that tilting of the lower sensing head relative to the optical axis of the upper sensing head has less effect on transmittance readings than on reflectance readings. Thus it is considered that it would be advantageous to have an optical window such as 135 with an absolute reflectance value of seventy percent (70%) or more. A value of reflectance as high as ninety percent (90%) would not be unreasonable and would generally still permit a transmittance value of a substantial magnitude to give reasonably comparable accuracy of reflectance and transmittance readings for on-line operation as herein described.

While separate photometric sensing means for the reflectance and transmittance readings have been shown, it is possible with the use of fiber optics, for example, to use a common photometric sensor and alternately supply light energy from the reflectance and transmittance light paths thereto, providing the response time of the sensor enables reflectance and transmittance readings to be obtained for essentially the same region of the moving web. Generally the possibility of such time multiplexing of reflectance and transmittance readings will depend on the speed of movement of the web and the degree of uniformity of sheet formation and the like.

It is very desirable that the system of the present invention be applicable to sheet materials having a wide range of characteristics such as basis weight and sheet formation, and operable at high speeds of movement such as 100 to 3000 feet per minute. Further, for maximum accuracy, it is necessary that a region of the sheet material being sampled have substantially uniform opacity. Accordingly, especially for sheet material of relatively low basis weight and relatively poor sheet formation, greater accuracy can be expected when the response of the photometric sensor is relatively fast, and when reflectance and transmittance readings are taken simultaneously and are a measure of the characteristics of a common sampling region of minimum area (consistent with adequate signal to noise ratios). Thus multiplexing of reflectance and transmittance readings is not preferred for the case of high speed paper machinery and comparable environments, nor is it desirable to use reflectance and transmittance light paths which intersect the web at spacially offset regions.

With respect to speed of response of the photometric sensing means, substantial improvements over the previously described components are deemed presently available. If the spectral response and other necessary characteristics are suitable, a sensor with such a higher speed of response is preferred for the illustrated embodiment. Good experience has been had with a silicon photocell presently considered as having an appropriate spectral response characteristics for color and other measurements in accordance with the present invention. The specific silicon cell referred to is identified as a Schottky Planar Diffuse Silicon Pin 10 DP photodiode of a standard series supplied by United Detector Technology Incorporated, Santa Monica, California.

In place of a rotatable filter wheel arrangement as shown in FIGS. 3 and 4, a set of twelve fiber optic light paths may define six simultaneously operative reflectance light paths in upper sensing head 11 and six simultaneously operative transmittance light paths in lower sensing head 12. The six reflectance fiber optic paths would include respective filters corresponding to filters 281–286 and respective individual photocells and would be located to receive respective portions of the reflected light which is reflected generally along path 137 in FIG. 3. The six transmittance fiber optic paths would also include respective filters corresponding to filters 281–286 and respective individual photocells, and would be located to receive respective portions of the transmitted light which is transmitted generally along paths such as 141–143 in FIG. 3. The filter means in the incident light path such as indicated at 133 in FIG. 3 might include a filter in series with filters 271 and 272 for filtering out the ultraviolet component from the incident beam, so that the twelve simultaneous photocell readings corresponding to those designated RSD1 through RSD6, and TSD1 through TSD6 (when the device is off-sheet), and corresponding to those designated RSP1 through RSP6, and TSP1 through TSP6 (when the device is on-sheet) will exclude a fluorescent contribution. (See Table 3 where this notation is introduced.)

If a reflectance reading corresponding to RSD7 (when the device is off-sheet) and corresponding to RSP7 (when the device is on-sheet) is desired so as to enable computation of fluorescent contribution to brightness, it would be necessary to mechanically remove the ultraviolet filter from the incident light path, or otherwise introduce an ultraviolet component of proper magnitude, and obtain another brightness (Z) reading, for example from the number four reflectance photocell.

As an alternative to the above fiber optic system with a common incident light path, seven fiber optical tubes incorporating filters corresponding to 281–287 of FIGS. 3 and 4, respectively, at say the light exit points of the tubes, could be used to supply the incident light to seven different points on the paper web. The reflected light from each of these seven points could be monitored by seven different systems, each involving lenses and a photocell, and the number seven reflected light path including also a filter corresponding to filter 288, FIG. 4. The transmitted light from the first six points would also need to be kept separately, and this could be accomplished by six integrating cavities and six photocells.

As a further alternative the seven fiber optical tubes defining the seven incident light paths could have a second set of seven fiber optical tubes and photocells respectively disposed to receive reflected light from the respective illuminated points. Another set of six fiber optical tubes and photocells could be associated with the first six illuminated points for receiving transmitted light. This could eliminate the need for the light collecting lenses in the upper sensing head and the integrating cavities in the lower sensing head.

The last two mentioned alternatives with seven fiber optical tubes defining the incident light paths appear to be rather complicated systems, but they do offer means of eliminating both the mechanical filter wheel as well as any mechanical device to control the presence of ultraviolet light in the incident beam.

Still another alternative is to use "screens" in addition to the filters in the embodiment of FIGS. 1–5. The new photodiodes are considered sensitive enough to measure reduced light intensities so that screens with different transmittance values could be used with six of the incident beam filters so that the net photocell output for each reflectance light path, and for each transmittance light path, would be similar enough so that separate and individual pre-amplification for the respective reflectance outputs would not be necessary, and so that separate and individual preamplification for each transmittance output would not be necessary. This means that reed switches 341–347 and 351–357, and relays $K_1$ through $K_7$ in FIG. 6 could be eliminated, and that the feedback paths for amplifiers 361 and 429 could have the same resistance value in each filter wheel position. A means of sensing filter wheel position would still be necessary, but this could be done in a number of simple ways, one of which would be a single reed switch such as reed switch 358 shown in FIG. 6. The number of necessary conductors in the cables 51 and 52, FIG. 5, would, of course, be reduced in this modification.

The term "screen is understood in the art as referring to a network of completely opaque regions and intervening openings or completely translucent regions, such that light energy is uniformly attenuated over the entire spectrum by an amount dependent on the proportion of opaque to transmitting area.

The device of FIGS. 1 and 2 has been tested on a machine operating at about 1000 feet per minute, and no problems have appeared in maintaining the necessary uniform and stable contact geometry between the head and the moving web.

It will be apparent that many further modifications and variations may be effected without departing from the scope of the novel concepts of the present invention.

Description Of The Off-The-Machine Optical Device Of FIGS. 21–23

FIGS. 21–23 illustrate an instrument for use off the paper machine. It is contemplated that this instrument will enable the development of the relationships between off-machine specification and the on-line instrument of FIGS. 1–20. These relationships would include the "grade-correction" factors to be used in the on-line system of FIGS. 1–20 relative to off-machine optical specifications. The instrument is shown as including a specimen support 1000 having an aperture 1001 which may conform with the aperture 130, FIG. 3, in diameter. The web support 1000 is of extended area so as to be capable of conveniently supporting a full-width web and for adjustment of such web to expose successive portions thereof at the aperture 1001. At the same time, the support 1000 will accommodate a small size paper specimen such as indicated at 1002. Generally the housing for the optical components will conform with the housing 11 of the prior embodiment from the standpoint of light proofing and interior finish.

The optical system as diagrammatically indicated includes a light source means 1010 and the lenses 1011–1016 generally having the characteristics of the lenses 202, 273 and 274 of FIG. 3 of the previous embodiment, and such that the spectral response of the system can duplicate that of the prior embodiment. The illustrated optical system further includes a fixed lamp socket 1020 and an iris diaphram 1021 for attenuating the incident light beam.

FIG. 21 illustrates also a transmittance sensing head 1025 which may be hingedly secured to the support 1000 at a single corner so as to minimize the obstruction provided to movement of a paper web over the support surface 1000. The transmittance sensing head 1025 may include an optical window 1026 of the same diameter, thickness and physical composition and characteristics as the window 135 of the prior embodiment. The description with respect to the window 135 is specifically incorporated here with respect to the window 1026 in its entirety. As illustrated, the lower surface of window 1026 may directly contact the paper specimen 1002 which will be in smooth continuous contact therewith over the optical viewing area of the system which may be of the same dimensions as that described with respect to the prior embodiment. The sensing head 1025 may comprise a light integrating cavity 1028 and a transmittance sensing light photocell 1030.

It will be understood that the reflectance and transmittance light paths have the incident path in common, and that in the illustrated embodiment the transmittance light path into the integrating cavity 1028 may conform with those described with respect to FIG. 3. Also, the reflectance light path generally conforms with that of FIG. 3 and includes a reflectance photocell 1032. The photocell 1032 may have a plate 1033 with a ⅜-inch aperture and may conform with the plate 275 of FIG. 3. Thus, a piece of diffusing glass corresponding to the glass 276 of FIG. 3 may be located in the aperture so that the light distribution over the surface of the photocell 1032 will conform to the light distribution with respect to the surface of photocell 203 in FIG. 3.

The instrument of FIG. 21 further includes an incident light filter disk 1040 and a reflected light filter disk 1041. The disks may be provided with low torque motors 1042 and 1043 which may operate essentially as described with respect to the motor 209 of FIG. 3. Both filter wheels 1040 and 1041 are under constant torque from a motor and slip-clutch arrangement. Each is prevented from turning by a stop pin seated in a small hole in the wheel. Each of the twenty-one filters in a wheel has a corresponding hole. The wheel rotates whenever a solenoid pulls the pin clear of the wheel. It stops again after the pin is dropped and a new hole comes under the pin allowing it to seat. Since this arrangement essentially conforms with that shown in FIG. 3, the details are not further illustrated in FIG. 21. It will be apparent that the indexing of the filter wheels 1040 and 1041 may be controlled from an on-line computer system 1230 in the same manner as generally described with respect to the preceding embodiment, so that further detail with respect to such on-line computer is unnecessary with respect to FIG. 21.

FIGS. 22 and 23 diagrammatically indicate the respective filters 1101–1121 and 1201–1221 of the filter disks 1040 and 1041. The filters 1101–1106 and 1201–1206 may conform identically to the filters 281–286 of FIG. 4, while filter positions 1107 and 1207 may be free of filters. The filters 281–286 have been designed as a standard filter for measuring TAPPI brightness, standard filters for a four-filter colorimeter and conventionally designated X (blue), X (red), Z and $Y_C$, and a filter required by the TAPPI standard method for opacity measurement, conventionally designated as a $Y_A$ filter. Thus filters 1101 through 1106 may be designated as TAPPI brightness, X (blue), X (red), Z, $Y_C$ and $Y_A$. The filters 287 and 288 were designated Z (blue) and Z (yellow). In this case, the complete number seven filter of the embodiment of FIG. 4 can be located at a position (for example position 1204) in the reflected beam. The filters 1108 through 1121 and 1208 through 1221 may comprise interference-type narrow-band filters which together transmit the complete visible spectrum.

By way of example each of the filter diameters may be ⅝ inch. The reflectance and transmittance photocells 1032 and 1030 may be of the Schottky silicon photodiode type. Amplifiers for each of the photodiodes can be Analog 234 K and AD 741 C. Two digital volt meters 1225 and 1226 can be used, one for reflectance and the other for transmittance and these may be 3½ digit, zero to 200 millivolt instruments with 8-4-2-1 BCD positive logic output.

As indicated at 1040a and 1041a, a portion of each of the filter wheels 1040 and 1041 is preferably exposed outside of the case so that the number of the filter in the optical train can be observed directly by the operator. The filter wheel arrangement accommodates a manual placement of both wheels to any position desired. Thus manual means is provided for unlocking the solenoid operated pin for each of the wheels, whereupon the wheels may be manually manipulated at the exposed region such as 1040a.

The ability for an operator to test a machine wide strip by moving it either left to right or right to left is desirable and is accommodated by the illustrated arrangement.

By providing at least one open position in the reflectance filter wheel, such as a position 1207, it will be apparent that the filter wheels 1040 and 1041 may provide the seven reflectance measurements and the six transmittance measurements with respect to the paper specimen 1002 in precise conformity with the corresponding measurements of the on-machine device. Reflectance and transmittance values could be obtained by the on-line computer system 1230 from simultaneous readings of the photocells 1030 and 1032, or the readings could be taken separately. Since the sensing head 1025 is conveniently removable, the instrument of FIG. 21 can also measure thickpad reflectivities, $R_{oo}$. The basic design consideration is that the reflectivity value determined on a thickpad would be in agreement with the established scale and that the thickpad reflectivity calculated from a reflectance and transmittance measurement made on a single sheet would be in agreement with the directly measured value. To accomplish this objective, fourteen narrow-band filters 1108–1121 and 1208–1221 are employed to obtain data permitting calculation of the thickpad reflectivity through the weighted-ordinate integration approach. Filters of identical kind are selectively introduced in the incident and reflected beam. Transmittance and reflectance measurements are performed with the open hole position such as 1207 in the reflected beam and the filter disk 1040 located through its various positions in the incident beam. The open hole 1107 in the incident beam is used with filter disk rotation in the reflected beam. In this way, fluorescence appearing in any part of the spectrum is handled properly.

The scope of the program presently under way includes construction of the instrument as shown in FIGS. 21–23 and testing of its operation to insure that it performs in accordance with the basic objective predicting thickpad reflectivity via the fourteen narrow-band filter and weighted ordinate integration approach.

The results of a feasibility study conducted at The Institute Of Paper Chemistry in which an Automatic Color-Brightness Tester equipped with sixteen narrow-band filters was employed to obtain $R_o$ and $R_{oo}$ values and the General Electric Recording Spectrophotometer was employed to obtain transmittance data indicate the success of this approach in calculating the thickpad reflectivity compared to the directly measured values. This work was conducted by a joint applicant herein, and is set forth in the following section.

Feasibility Study for the Design and Construction of a Laboratory Instrument Based on the Principle of the On-Machine Device The ACBT equipped with the sixteen narrow-band filters was used to obtain $R_o$ and $R_{oo}$ values for six paper samples. Transmittance data for the same specimens were obtained using the conventional GERS. $R_{oo}$ values were calculated using the following formulas.

$$a = (1 + R_o^2 - T^2)/R_o$$

$$R_{oo} = (a/2) - \sqrt{(a/2)^2 - 1}$$

The values for T, $R_o$, $R_{oo}$ measured and $R_{oo}$ calculated, are given in Table A. The data show reasonable agreement between the measured and calculated $R_{oo}$ values. There are several factors which contribute to the differences. Fluorescence was not properly accounted for and some of the samples do fluoresce, particularly Samples 18 and 29. The samples were illuminated with a collimated beam whereas the theoretical relationship is based on diffuse illumination and diffuse viewing. The samples do change somewhat with handling as a large number of readings must be taken on each specimen. The same specimens were evaluated on filters No. 6 and 21 after all the data were collected. The data given in Table C show that some changes occurred as a result of handling during the many tests.

Tristimulus values were calculated from the $R_{oo}$ values obtained from the T and $R_o$ values using the weighting factors given by the CIE system. These tristimulus values were then compared with the directly measured tristimulus values obtained on the ACBT using the "tristimulus filters". The data, given in Table B show good agreement for most of the samples. Here again the same factors discussed earlier are responsible for the differences. In addition, the braod-band tristimulus functions of the ACBT no doubt differ slightly from the theoretical functions. It appears that sample 29 (cherry bond) shows the largest discrepancy.

It appears feasible to design and construct an instrument similar to the on-machine device of FIGS. 1–20 but also equipped with narrow-band filters which would give very nearly the correct tristimulus values in either mode. Perhaps the reasons for the discrepancies noted could be determined and further improvements made.

Table A

| Sample | T | $R_o$ | RINFM | RINFC | RINFM-RINFC |
|---|---|---|---|---|---|
| 6-3 | 0.0940 | 0.6180 | 0.6250 | 0.6270 | −0.0020 |
| 618 | 0.1070 | 0.4730 | 0.4740 | 0.4801 | −0.0061 |
| 620 | 0.1150 | 0.5590 | 0.5700 | 0.5701 | −0.0001 |
| 623 | 0.0420 | 0.4440 | 0.4450 | 0.4450 | 0.0000 |
| 629 | 0.0250 | 0.2940 | 0.2940 | 0.2942 | −0.0002 |
| 630 | 0.0110 | 0.2330 | 0.2340 | 0.2330 | 0.0010 |
| 7-3 | 0.1120 | 0.6920 | 0.7120 | 0.7095 | 0.0025 |
| 718 | 0.1270 | 0.7610 | 0.7880 | 0.7933 | −0.0053 |
| 720 | 0.1350 | 0.5930 | 0.6100 | 0.6104 | −0.0004 |
| 723 | 0.0420 | 0.4440 | 0.4460 | 0.4450 | 0.0010 |
| 729 | 0.0280 | 0.3110 | 0.3110 | 0.3113 | −0.0003 |
| 730 | 0.0090 | 0.2190 | 0.2210 | 0.2190 | 0.0020 |
| 8-3 | 0.1350 | 0.7270 | 0.7580 | 0.7578 | 0.0002 |
| 818 | 0.1460 | 0.8200 | 0.8740 | 0.8903 | −0.0163 |
| 820 | 0.1500 | 0.6160 | 0.6400 | 0.6398 | 0.0002 |
| 823 | 0.0490 | 0.4640 | 0.4660 | 0.4654 | 0.0006 |
| 829 | 0.0350 | 0.3300 | 0.3300 | 0.3305 | −0.0005 |
| 830 | 0.0120 | 0.2390 | 0.2400 | 0.2390 | 0.0010 |
| 9-3 | 0.1480 | 0.7370 | 0.7760 | 0.7768 | −0.0008 |
| 918 | 0.1550 | 0.8050 | 0.8660 | 0.8765 | −0.0105 |
| 920 | 0.1610 | 0.6240 | 0.6530 | 0.6525 | 0.0005 |
| 923 | 0.0630 | 0.4910 | 0.4940 | 0.4936 | 0.0004 |
| 929 | 0.0240 | 0.2810 | 0.2810 | 0.2812 | −0.0002 |
| 930 | 0.0170 | 0.2700 | 0.2710 | 0.2701 | 0.0009 |
| 10-3 | 0.1600 | 0.7460 | 0.7980 | 0.7962 | 0.0018 |
| 1018 | 0.1650 | 0.7980 | 0.8700 | 0.8778 | −0.0078 |
| 1020 | 0.1740 | 0.6380 | 0.6740 | 0.6738 | 0.0002 |
| 1023 | 0.1090 | 0.5820 | 0.5930 | 0.5928 | 0.0002 |
| 1029 | 0.0130 | 0.2090 | 0.2090 | 0.2090 | −0.0000 |
| 1030 | 0.0430 | 0.3650 | 0.3690 | 0.3658 | 0.0032 |
| 11-3 | 0.1660 | 0.7520 | 0.8110 | 0.8089 | 0.0021 |
| 1118 | 0.1680 | 0.7950 | 0.8740 | 0.8766 | −0.0026 |
| 1120 | 0.1750 | 0.6390 | 0.6750 | 0.6754 | −0.0004 |
| 1123 | 0.1310 | 0.6260 | 0.6440 | 0.6445 | −0.0005 |
| 1129 | 0.0090 | 0.1590 | 0.1590 | 0.1590 | −0.0000 |
| 1130 | 0.0860 | 0.4700 | 0.4760 | 0.4745 | 0.0015 |
| 12-3 | 0.1680 | 0.7480 | 0.8090 | 0.8051 | 0.0039 |
| 1218 | 0.1730 | 0.7910 | 0.8760 | 0.8766 | −0.0006 |
| 1220 | 0.1670 | 0.6210 | 0.6510 | 0.6515 | −0.0005 |
| 1223 | 0.1300 | 0.6170 | 0.6350 | 0.6346 | 0.0004 |
| 1229 | 0.0100 | 0.1400 | 0.1400 | 0.1400 | −0.0000 |
| 1230 | 0.1220 | 0.5400 | 0.5530 | 0.5517 | 0.0013 |
| 13-3 | 0.1680 | 0.7420 | 0.8000 | 0.7971 | 0.0029 |
| 1318 | 0.1740 | 0.7890 | 0.8760 | 0.8744 | 0.0016 |
| 1320 | 0.1520 | 0.5950 | 0.6170 | 0.6176 | −0.0006 |
| 1323 | 0.1170 | 0.5920 | 0.6040 | 0.6049 | −0.0009 |
| 1329 | 0.0110 | 0.1360 | 0.1360 | 0.1360 | −0.0000 |
| 1330 | 0.1520 | 0.5960 | 0.6200 | 0.6186 | 0.0014 |
| 14-3 | 0.1700 | 0.7350 | 0.7900 | 0.7893 | 0.0007 |
| 1418 | 0.1770 | 0.7880 | 0.8760 | 0.8769 | −0.0009 |
| 1420 | 0.1280 | 0.5480 | 0.5600 | 0.5613 | −0.0013 |
| 1423 | 0.0910 | 0.5400 | 0.5470 | 0.5464 | 0.0006 |
| 1429 | 0.0160 | 0.1510 | 0.1510 | 0.1510 | −0.0000 |
| 1430 | 0.1860 | 0.6450 | 0.6900 | 0.6878 | 0.0022 |
| 15-3 | 0.1680 | 0.7320 | 0.7870 | 0.7839 | 0.0031 |
| 1518 | 0.1800 | 0.7870 | 0.8780 | 0.8796 | −0.0016 |
| 1520 | 0.1000 | 0.5000 | 0.5060 | 0.5068 | −0.0008 |
| 1523 | 0.0690 | 0.4870 | 0.4900 | 0.4901 | −0.0001 |
| 1529 | 0.0470 | 0.3230 | 0.3250 | 0.3238 | 0.0012 |
| 1530 | 0.2290 | 0.7010 | 0.8000 | 0.7952 | 0.0048 |
| 16-3 | 0.1720 | 0.7330 | 0.7910 | 0.7882 | 0.0028 |
| 1618 | 0.1810 | 0.7880 | 0.8840 | 0.8832 | 0.0008 |
| 1620 | 0.0820 | 0.4560 | 0.4600 | 0.4599 | 0.0001 |
| 1623 | 0.0530 | 0.4370 | 0.4380 | 0.4385 | −0.0005 |
| 1629 | 0.1680 | 0.6070 | 0.6400 | 0.6363 | 0.0037 |
| 1630 | 0.2430 | 0.7220 | 0.8610 | 0.8532 | 0.0078 |
| 17-3 | 0.1770 | 0.7400 | 0.8080 | 0.8018 | 0.0062 |
| 1718 | 0.1840 | 0.7880 | 0.8920 | 0.8882 | 0.0038 |
| 1720 | 0.0680 | 0.4220 | 0.4240 | 0.4244 | −0.0004 |
| 1723 | 0.0410 | 0.3960 | 0.3960 | 0.3968 | −0.0008 |
| 1729 | 0.2400 | 0.7140 | 0.8240 | 0.8321 | −0.0081 |
| 1730 | 0.2470 | 0.7240 | 0.8790 | 0.8654 | 0.0136 |
| 18-3 | 0.1870 | 0.7480 | 0.8290 | 0.8228 | 0.0062 |
| 1818 | 0.1880 | 0.7900 | 0.9020 | 0.9001 | 0.0019 |
| 1820 | 0.0660 | 0.4170 | 0.4190 | 0.4192 | −0.0002 |
| 1823 | 0.0380 | 0.3880 | 0.3880 | 0.3887 | −0.0007 |
| 1829 | 0.2520 | 0.7300 | 0.8780 | 0.8928 | −0.0148 |
| 1830 | 0.2510 | 0.7240 | 0.8850 | 0.8739 | 0.0111 |
| 19-3 | 0.1950 | 0.7560 | 0.8530 | 0.8450 | 0.0080 |
| 1918 | 0.1930 | 0.7900 | 0.9140 | 0.9111 | 0.0029 |
| 1920 | 0.0710 | 0.4230 | 0.4250 | 0.4256 | −0.0006 |
| 1923 | 0.0410 | 0.3930 | 0.3940 | 0.3938 | 0.0002 |

Table A-continued

| Sample | T | $R_o$ | RINFM | RINFC | RINFM-RINFC |
|---|---|---|---|---|---|
| 1929 | 0.2580 | 0.7300 | 0.8980 | 0.9111 | −0.0131 |
| 1930 | 0.2550 | 0.7230 | 0.8900 | 0.8806 | 0.0094 |
| 20-3 | 0.2030 | 0.7640 | 0.8790 | 0.8715 | 0.0075 |
| 2018 | 0.1980 | 0.7930 | 0.9270 | 0.9345 | −0.0075 |
| 2020 | 0.0660 | 0.4110 | 0.4130 | 0.4132 | −0.0002 |
| 2023 | 0.0400 | 0.3840 | 0.3840 | 0.3847 | −0.0007 |
| 2029 | 0.2610 | 0.7280 | 0.9080 | 0.9142 | −0.0062 |
| 2030 | 0.2590 | 0.7240 | 0.8960 | 0.8940 | 0.0020 |
| 21-3 | 0.2110 | 0.7630 | 0.8960 | 0.8838 | 0.0122 |
| 2118 | 0.2020 | 0.7890 | 0.9340 | 0.9337 | 0.0003 |
| 2120 | 0.0900 | 0.4650 | 0.4770 | 0.4699 | 0.0071 |
| 2123 | 0.0560 | 0.4410 | 0.4480 | 0.4427 | 0.0053 |
| 2129 | 0.2610 | 0.7240 | 0.9110 | 0.8999 | 0.0111 |
| 2130 | 0.2600 | 0.7180 | 0.8980 | 0.8792 | 0.0188 |

T Transmittance measured with GERS
$R_o$ Reflectance with black backing measured on the ACBT
RINFM Reflectance of opaque pad measured on the ACBT
RINFC Reflectance of opaque pad as calculated from $R_o$ and T
RINFM-RINFC Difference between the measured and calculated $R_{\infty}$ values
Sample The first number (6 through 21) designates the filter number. The last two characters designate the sample number.

Table B

| | X | | Y | | Z | |
|---|---|---|---|---|---|---|
| Sample | C | M | C | M | C | M |
| 3 | 77.7 | 77.9 | 79.6 | 79.3 | 90.4 | 90.6 |
| 18 | 86.5 | 86.3 | 88.0 | 87.6 | 102.4 | 102.5 |
| 20 | 49.3 | 50.0 | 55.1 | 55.2 | 76.4 | 76.3 |
| 23 | 45.0 | 45.3 | 52.8 | 52.9 | 59.7 | 59.9 |
| 29 | 52.2 | 50.9 | 34.2 | 31.5 | 33.0 | 31.8 |
| 30 | 71.1 | 69.9 | 68.5 | 68.2 | 34.0 | 33.9 |

C Values calculated from narrow-band filter data.
M Values determined using the "tristimulus filters".
Sample Description
   3    Advantage offset wave 50 lb.
  18   S-20 Nekoosa Bond
  20   S-20 Nekoosa Bond Blue
  23   S-20 Nekoosa Bond Green
  29   S-20 Nekoosa Bond Cherry
  30   S-20 Nekoosa Bond Buff

Table C

Change in the Measured $R_{\infty}$ Values with Handling for No. 6 and 21 Filters on the ACBT No. 6 Filter (401 nm)

| | 3 | 18 | 20 | 23 | 29 | 30 |
|---|---|---|---|---|---|---|
| Start of test | 0.625 | 0.474 | 0.570 | 0.445 | 0.294 | 0.234 |
| End of test | 0.623 | 0.465 | 0.570 | 0.445 | 0.293 | 0.234 |

No. 21 Filter (697 nm)

| | 3 | 18 | 20 | 23 | 29 | 30 |
|---|---|---|---|---|---|---|
| Start of test | 0.896 | 0.934 | 0.477 | 0.448 | 0.911 | 0.898 |
| End of test | 0.889 | 0.927 | 0.474 | 0.446 | 0.895 | 0.898 |

Instructions for Using the Off-Machine Instrument of FIGS. 21–23

The instrument should be located in a reasonably constant temperature room and positioned so that intense room lights are not located directly above it.

Apply power (60 hz, 117 V) to the instrument and throw the power switch and the filter disk drive switch to the "on" position. For best operation, allow about two hours for warm-up. It is suggested to leave the instrument "on" continuously as temperature changes do influence the reading. The lamp voltage (5.83 volts as measured at the test terminals) should be checked occasionally.

The first step in calibration is to place the reflected beam filter disk 1041 to the brightness (B) position and the incident beam filter disk 1040 to the open hole (O).

Place the opal glass standard over the specimen opening. The transmittance unit 1025 should be set back out of the way.

Adjust the right hand potentiometer (not shown) on the front of the instrument so that the value assigned to the standard appears on the right hand digital panel meter (DPM) designated 1225 in FIG. 21. If necessary, the coarse adjust potentiometer (not shown) may be used to make the adjustment. When this adjustment is properly made, it should be possible to check the paper brightness calibration standards. Upon completion of that check, papermaker's brightness of other samples can be measured. Occasional reference to the opal glass standard should be made to check the stability of the instrument.

The instrument should then be calibrated for the measurement of the tristimulus values for Illuminant C. The step switch (not shown) on the right should be pressed to move the filter disk 1041 in the reflected beam to the XB position which gives the blue portion of the X function. Place the calibrated ceramic color standard over the specimen opening and adjust the potentiometer No. 2 on the right (not shown) in the sloping portion of the front panel so that the right DPM 1225 indicates the value assigned to the ceramic standard for that function. The remaining three functions XR, Z and $Y_c$ can be calibrated in the same manner using the appropriate potentiometers. The reflectance values can then be determined for each function and converted to CIE tristimulus values as follows:

$$X = 0.9804[(0.2012 R_{XB}) + (0.7988 R_{XR})]$$

$$Y_c = R Y_c$$

$$Z = 1.1812 R_Z$$

The next position (1206, FIG. 23) on the filter disk 1041 gives the spectral response of the $E_a \bar{y}$ function which is appropriate for the measurement of opacity. This position can be calibrated in the same manner. TAPPI opacity can be calculated from the $R_o$ and $R_{oo}$ values as follows when R' equals 0.89.

$$R_{R'} = R_o + \frac{R'(R_{oo} - R_o)(1 - R_o R_{oo})}{R_{oo}(1 - R_o R')}$$

TAPPI Opacity = $100 R_o / R_{R'}$

The narrow-band interference type filters are located in positions marked 420 through 680. The numbers marked on the filter disk are nominal wavelengths. The actual effective wavelengths are as follows:

| Position | Effective Wavelength, nm | Associated Reference Numeral, | |
|---|---|---|---|
| 420 | 423 | 1108 | 1208 |
| 440 | 439 | 1109 | 1209 |
| 460 | 456 | 1110 | 1210 |
| 480 | 475 | 1111 | 1211 |
| 500 | 505 | 1112 | 1212 |
| 520 | 523 | 1113 | 1213 |
| 540 | 540 | 1114 | 1214 |
| 560 | 559 | 1115 | 1215 |
| 580 | 579 | 1116 | 1216 |
| 600 | 598 | 1117 | 1217 |
| 620 | 617 | 1118 | 1218 |
| 640 | 641 | 1119 | 1219 |
| 660 | 655 | 1120 | 1220 |
| 680 | 672 | 1121 | 1221 |

The instrument can be calibrated to read the correct standard value for these positions (1208-1221, FIG. 23) using the appropriate potentiometers 8 through 21 on the right (not shown). The tristimulus values can be calculated by integrating the product of the reflectances obtained and the appropriate weighting function of the CIE system. The time element would be excessively long if this were to be done manually. However, computer processing of the data by computer system 1230, FIG. 21, should minimize the time factor. The reflectance measurements performed so far, with the open hole 1107 in the incident beam and with reflected beam filtering, includes the fluorescent component as is the case of using the conventional brightness tester.

The next mode would be to set the filter disk 1041 in the reflected beam to the open hole position (O) and set the incident filter disk 1040 to the brightness position (B), for example position 1101, FIG. 23. Place the opal glass standard over the specimen opening and adjust the No. 15 potentiometer on the left bank to give the value of the glass standard on the right DPM 1225. The instrument is then ready to measure brightness excluding the fluorescent component. This exclusion of the fluorescent component is somewhat different from the usual laboratory standard instrument in that both filter components are placed in the incident beam. This was necessary to permit the measurement of transmittance using the same filter components. It is also different from OMOD. However, once the relationship is established, it should remain fixed and a factor may be employed to relate the different systems.

The other active positions (e.g. 1102-1106 and 1108-1121, FIG. 22,) on the filter disk 1040 may be calibrated in the same manner using respective corresponding potentiometers in the left bank (not shown).

There is some drift evident when the filters are placed in the incident beam as a result of the change in filter temperature upon exposure to the beam. This effect may be minimized by exposing the filter to the beam about the same length of time for calibration as for evaluation of a sample. This is also a problem with OMOD. However, if the period to which the filter is exposed to the light source is fixed, then the error should be minimal.

The next mode is the measurement of transmittance. The transmittance head 1025, FIG. 21, should be placed over the specimen opening 1001 and the incident beam filter disk 1040 placed in the brightness position (B). The reading on the left hand DPM 1226, FIG. 21, should be adjusted to 100.0 using the fine gain control knob (second from left) on the front panel of the instrument. The coarse gain control (left knob) may be used if necessary. The remaining positions (e.g. 1102-1106, FIG. 22) can then be calibrated to 100.0 using the potentiometers No. 2 through 6 in the left bank.

The instrument is now in calibration for the measurement of reflectance including the fluorescent component, the measurement of reflectance excluding the fluorescent component and the measurement of transmittance. Reflectance and/or transmittance values may be obtained for the following functions.

1. Papermaker's brightness
2. Tristimulus functions, $E_c \bar{x}$, $E_c \bar{y}$ and $E_c \bar{z}$
3. Opacity, $E_a \bar{y}$
4. Narrow-band reflectance data from 420 to 680 nm (nominal) at approximately 20 nm intervals.

The measurement of reflectance and transmittance of a single sheet of paper permits the calculation of the $R_{oo}$ value for an opaque pad if the measurements are performed correctly. In this case, the use of the broad spectral functions of the CIE system causes an error in the calculated $R_{oo}$ value. However, for a given color or shade, this error should be fairly constant thus permitting a correction to be applied by grade.

The transmittance measurement as performed on the instrument of FIGS. 21-23 is not true transmittance but a ratio of the paper plus the diffuser transmittance in series to the diffuser transmittance which is designated $T_{pd}/T_d$. The reflectance value is that of the paper backed by the diffuser 1026, FIG. 21, ($R_{pd}$) relative to the absolute reflectance of magnesium powder. It is possible to calculate the effective diffuser reflectance through the measurement of the true $R_o$ and $R_{oo}$ values as follows.

$$T^2 = [1-(R_o/R_{oo})][1-(R_o R_{oo})]$$

$$R_d = (R_{pd} - R_o)/(R_o R_{pd} + T^2 - R_o^2)$$

T and $R_o$ can be calculated from $R_{pd}$, $R_d$ and $T_{pd}/T_d$ as follows.

$$R_o = [R_{pd} - R_d(T_{pd}/T_d)^2]/[1-(R_d T_{pd}/T_d)^2]$$

$$T = (T_{pd}/T_d)[1-(R_d R_{pd})]/[1-(R_d T_{pd}/T_d)^2]$$

Knowing T and $R_o$ of the single sheet, the reflectance of an opaque pad ($R_{oo}$) can be calculated.

$$a = (1 + R_o^2 - T^2)/R_o$$

$$R_{oo} = (a/2) - \sqrt{(a/2)^2 - 1}$$

The instrument permits the determination of the transmittance and reflectance of a single sheet from which $R_{oo}$ can be calculated as well as permitting the direct measurement of $R_{oo}$ so that it should be possible to establish grade corrections for OMOD by comparison of the calculated $R_{oo}$ with the measured $R_{oo}$. Also, the fluorescent contribution can be determined with the instrument to assist in the operation of OMOD, (the on-machine instrument of FIGS. 1-20).

We claim as our invention:

1. Apparatus for measuring an optical property of a single thickness sheet material, the apparatus comprising receiving means for receiving a single thickness sheet material having a fluorescent constituent, light source means, reflectance measuring photometric sensing means, light path means including a reflectance light path, and operable for directing light energy in a visible band and in a fluorescent producing band from the light source means to the reflectance measuring photometric sensing means via a single thickness sheet material at the receiving means, and light spectrum control means for controlling the spectrum of light energy so directed to the reflectance measuring photometric sensing means by the light path means and operable for producing by means of the reflectance measuring photometric sensing means a first reflectance signal substantially exclusive of any fluorescent contribution, and operable for characterizing the optical property substantially exclusive of the fluorescent contribution, the light path means being further operable for directing the fluorescence producing band of light energy to impinge on single thickness sheet material at the receiving means for producing by means of the reflectance measuring photometric sensing means a second reflectance signal comprised of a fluorescent contribution to the optical property, in which the control means comprises spectral response filter means for essentially blocking the fluorescence producing band, and the light path means simultaneously providing a transmittance light path such that the light path means provides simultaneously operative reflectance and transmittance light paths each including at least the light souce means, said spectral response filter means, and photometric sensor means, the reflectance and transmittance light paths having substantially a common spectral response characteristic sufficient to characterize the optical property but being respectively arranged for collecting light from the receiving means after impingement on sheet material thereat under respective substantially differentiated conditions such as to essentially characterize a plurality of essentially independent optical response parameters of the sheet material each substantially excluding fluorescence and such as to characterize the optical property with substantially greater accuracy than any characterization of said optical property by one of such optical response parameters taken by itself, in which the transmittance light path includes an optical window member of translucent diffusing material, the window member being disposed on the opposite side of the receiving means from the light source means and having an extended surface adjacent the receiving means for underlying the sheet material, the transmittance light path including transmittance measuring photometric sensing means for receiving light from the light source means after transmission through the single thickness sheet material at the receiving means and through the optical window member, and means whereby the transmittance mesuring photometric sensing means is operable for providing a transmittance signal simultaneously with the production of the first reflectance signal by the reflectance measuring photometric sensing means.

2. Apparatus as claimed in claim 1 having means for guiding a moving web of single thickness of sheet material into conforming stable contact wih the extended surface of the optical window member.

3. Apparatus as claimed in claim 1 in which the optical window member has an absolute reflectance value of about thirty-five percent and an absolute transmittance value of substantial magnitude.

4. Apparatus as claimed in claim 3 in which the optical window member has an absolute reflectance value of about seventy percent.

5. Apparatus as claimed in claim 4 in which the optical window member has an absolute reflectance of about ninety percent.

6. Apparatus as claimed in claim 3 in which the optical window member has an absolute transmittance value equal to or less than fifty-six percent.

7. Apparatus as claimed in claim 1 in which the sheet receiving means is arranged for receiving a web of sheet material moving along a web path.

8. Apparatus as claimed in claim 1 with automatic digital computer means connected on line with the photometric sensing means for receiving therefrom the output signals and automatically operable on the basis of the output signals to calculate a quantitative indication of the optical property and of the fluorescent constituent thereof, means comprising said automatic digital computer means for receiving the output from said reflectance measuring and transmittance measuring photometric sensing means in the absence of sheet material at said sheet receiving means and for causing the computer means to thereupon store the output from the photometric sensing means as characterizing the current optical response of the optical window member itself exclusive of the sheet material.

9. Apparatus for measuring a plurality of optical properties of single thickness sheet material, comprising an optical measuring system including light source means, sheet receiving means for receiving a single thickness of sheet material, and photometric sensor means for receiving light energy from the light source means after impingement on single thickness sheet material at said sheet receiving means to provide reflectance and transmittance measurement components with respect to such sheet material at said sheet receiving means, the optical measuring system having further means operable in conjunction with said photometric sensor means for providing a plurality of resultant outputs from the system in accordance with a plurality optical measurement spectral response functions corresponding to such optical properties, and an optical window member having an absolute reflectance of substantial value, having an absolute transmittance of substantial value, and being disposed for partially reflecting light energy received from the sheet receiving region back toward the sheet receiving region and for partially transmitting light energy so as to provide for a plurality of standardization readings from the photometric sensor means in the absence of sheet material in said sheet receiving region.

10. Apparatus according to claim 9 with said further means comprising a plurality of spectral response filter means having respective spectral response characteristics for characterizing said optical properties, said filter means being mounted for controlling the spectrum of light energy from the light source means received by the photometric sensor means, and providing for the generation of a plurality of reflectance measurement components with at least one thereof including a fluorescent component and another thereof excluding a fluorescent component and both in accordance with a common optical measurement spectral response function.

11. Apparatus according to claim 9 with said further means comprising spectral response filter means having a spectral response characteristic in accordance with a brightness measurement spectral response function such that one of said outputs may be used to provide a quantitative indication of the brightness of the single thickness sheet material with substantially greater accuracy than a corresponding quantitative indication based on a reflectance or transmittance measurement alone.

12. Apparatus according to claim 9 with said further means comprising a plurality of spectral response filter means having spectral response characteristics in accordance with respective color component measurement spectral response functions such that the optical system provides outputs for characterizing the color of the single thickness sheet material with substantially greater accuracy than a characterization on the basis of reflectance or transmittance measurements alone.

13. Apparatus according to claim 9 with said further means including spectral response filter means having a spectral response characteristic in accordance with an opacity measurement spectral response function such that one of said outputs may be used to provide a quantitative indication of the opacity of the single thickness sheet material with substantially greater accuracy than a corresponding quantitative indication based on a reflectance or transmittance measurement alone.

14. Apparatus according to claim 9 with said further means comprising a series of narrow band filter means together covering a spectrum of light energy for characterizing said plurality of optical properties, and mounted for controlling the spectrum of light energy from the light source means received by the photometric sensor means.

15. Apparatus according to claim 14 with said further means comprising two series of narrow band filters each for covering a spectrum of light energy for characterizing fluorescence, one series being arranged to block ultraviolet energy from reaching the sheet receiving region and the other series accomodating the transmission of ultraviolet energy to the sheet receiving region, thereby to provide respective series of outputs from the measuring device suitable for characterizing the fluorescence of the sheet material.

16. Apparatus for measuring an optical property of single thickness sheet material, comprising an optical measuring system including light source means, sheet receiving means for receiving light energy therefrom, photometric sensor means for receiving light energy from the sheet receiving means for providing respective reflectance and transmittance output signal components as a function of respective reflectance and transmittance parameters of a single thickness sheet material at the sheet receiving means, and further means operable in conjunction with said photometric sensor means for providing a quantitative output based on the reflectance and transmittance output signal components and in accordance with an optical measurement spectral response function for characterizing the optical property, said further means comprising an optical window member disposed in optical coupling relation to said sheet receiving means during the sensing of the reflectance and transmittance parameters of sheet material at said sheet receiving means and comprising translucent diffusing material exhibiting an absolute reflectance of substantial magnitude and an absolute transmittance of substantial magnitude.

17. Apparatus according to claim 16 with said optical window member in conjunction with said photometric sensor means providing said reflectance output signal component and said transmittance output signal component, both with a sheet material at the sheet receiving means and without a sheet material at the sheet receiving means, for characterizing the optical property of the sheet material and for providing a reference standardizing measurement of the optical property with respect to the optical window member alone.

18. Apparatus according to claim 16 with said translucent diffusing material having an absolute reflectance of about thirty-five percent.

19. Apparatus according to claim 16 with said translucent diffusing material having an absolute reflectance in the range from about 35% to about 90%.

20. Apparatus according to claim 16 with said further means in conjunction with said photometric sensor means being operable for providing a quantitative output based on said reflectance and transmittance output signal components and in accordance with an opacity measurement spectral response function.

21. Apparatus according to claim 16 with said further means in conjunction with said photometric sensor means being operable for providing a quantitative output based on said reflectance and transmittance output signal components and in accordance with a brightness measurement spectral response function.

22. Apparatus according to claim 16 with said further means in conjunction with said photometric sensor means being operable for providing a quantitative output based on said reflectance and transmittance output signal components and in accordance with each of a plurality of color component measurement spectral response functions for characterizing the color of single thickness sheet material at the sheet receiving means.

23. Apparatus according to claim 16 with said further means in conjunction with said photometric sensor means being operable for providing a quantitative output based on said reflectance and transmittance output signal components and in accordance with each of an opacity measurement spectral response function and a brightness measurement spectral response function.

24. Apparatus for obtaining a quantitative measure of an optical property of a moving web of substantially homogeneous sheet material, which comprises:
 (a) an optical monitoring device having a web receiving region for receiving in operative relation thereto a web of sheet material moving along a web path,
 (b) said optical monitoring device having an optical system with photometric sensor means capable of providing two essentially independent output signals and with two distinct light energy paths each including light source means, spectral response filter means and said photometric sensor means, said photometric sensor means being responsive to light energy received from the web receiving region after impingement on sheet material in said region,
 (c) each of said two distinct light energy paths having substantially a common spectral response characteristic sufficient to characterize said optical property but being respectively arranged for collecting said light energy from the web receiving region after impingement on said web under respective substantially differentiated conditions so as to provide respective essentially independent output signals from said photometric sensor means such as to essentially characterize two essentially independent optical response parameters of the sheet material and such as to characterize the optical property with substantially greater accuracy than any characterization of said optical property by either one of such optical response parameters taken by itself,
 (d) automatic digital computer means connected on line with said optical monitoring device and coupled with said photometric sensor means for receiving therefrom said respective essentially independent output signals in accordance with the respective essentially independent optical response parameters and automatically operable on the basis of said output signals to calculate a quantitative indication of said optical property,
 (e) said monitoring device including an optical window member disposed on the opposite side of the web receiving region from said light source means, and having an extended web-engaging surface adjacent the web receiving region for slidably supporting the web of sheet material as it moves through said web receiving region, said optical window member having a substantial absolute reflectance and a substantial absolute transmittance, and
 (f) one of the light energy paths being a reflectance sensing light path for sensing of reflectance of the sheet material as backed by said optical window member and the other of said light energy paths being a transmittance sensing light path for sensing the transmittance of the sheet material and said optical window member in series.

25. Apparatus according to claim 24, with means mounting said monitoring device for movement transversely of the web path to sample the reflectance and transmittance of the web of sheet material at different portions of the width thereof, and mounting said monitoring device for movement to an off-web position to one side of the web path such that said optical window member is clear of the web of sheet material, and means for automatically signalling said digital computer means when the monitoring device is in the off-web position and for cuasing the computer means to thereupon store the output signals from the photometric sensor means as reflectance and transmittance values for the optical window member itself exclusive of the sheet material.

26. An optical property calibration system for on-line web optical property measuring apparatus including light source means, a web receiving region for receiving a web of single thickness sheet material, and photometric sensor means for receiving light energy from the light source means after impingement on the web of single thickness sheet material at said web receiving region to provide reflectance and transmittance measurement components with respect to such web of single thickness sheet material at said web receiving region, and further means operable in conjunction with said photometric sensor means for providing resultant output information from the system in accordance with at least one optical measurement spectral response function corresponding to at least one optical property, said optical property calibration system comprising an optical window member for partially reflecting and partially transmitting light incident thereon, said window member being disposed for reflecting a substantial proportion of the light energy received from the web receiving region back toward the web receiving region and for also transmitting light energy so as to provide for at least one standardization reading from the photometric sensor means in the absence of the web in said web receiving region.

27. An optical property calibration system according to claim 26 with said optical window member comprising translucent diffusing material having a surface area disposed for sliding contact with the web of single thickness sheet material.

28. An optical property calibration system according to claim 27 with processing means for receiving reflectance and transmittance signals in accordance with the optical response of the translucent diffusing material with respect to light energy from the light source means impinging on said surface area of said translucent diffusing material and respectively reflected therefrom and transmitted therethrough in the absence of a web at the web receiving region.

29. An optical property calibration system according to claim 28 with said processing means being operative to store values for said reflectance and transmittance signals with respect to a brightness spectral response function.

30. An optical property calibration system according to claim 27 with said processing means being operative to store values for said reflectance and transmittance signals with respect to a plurality of color-characterizing spectral response functions.

31. An optical property calibration system according to claim 28 with said processing means being operative to store values for said reflectance and transmittance signals with respect to an opacity characterizing spectral response function.

32. An optical property calibration system according to claim 26 with said optical window member comprising translucent diffusing material for disposition in series with the light source means and the web of single thickness sheet material during generation of the transmittance measurement component, and processing means for receiving a transmittance signal in accordance with the transmittance of the translucent diffusing material in the absence of a web at the web receiving region.

33. An optical property calibration system according to claim 32 with said processing means being operative to store a value for said transmittance signal with respect to a brightness spectral response function.

34. An optical property calibration system in accordance with claim 32 with said processing means being operative to store a value for said transmittance signal with respect to a plurality of color-characterizing spectral response functions.

35. An optical property calibration system according to claim 32 with said processing means being operative to store a value for said transmittance signal with respect to an opacity characterizing spectral response function.

36. An optical property calibration system according to claim 32 with said translucent diffusing material having an absolute transmittance equal to or less than fifty-six percent.

37. An optical property calibration system according to claim 26 with said optical window member being arranged in backing relation to the web of single thickness sheet material during generation of the reflectance measurement component, and processing means for receiving a reflectance signal in accordance with the reflectance of the optical window member in the absence of a web at the web receiving region.

38. An optical property calibration system in accordance with claim 37 with said processing means being operative to store a value for said reflectance signal with respect to a brightness spectral response function.

39. An optical property calibration system according to claim 37 with said processing means being operative to store a value for said reflectance signal with respect to each of a plurality of color-characterizing spectral response functions.

40. An optical property calibration system according to claim 37 with said processing means being operative to store a value for said reflectance signal with respect to an opacity characterizing spectral response function.

41. An optical property calibration system according to claim 37 with said optical window member comprising translucent diffusing material having an absolute reflectance of about thirty-five percent.

42. An optical property calibration system according to claim 37 with said optical window member comprising translucent diffusing material having an absolute reflectance of about seventy percent.

43. An optical property calibration system according to claim 37 with said optical window member comprising translucent diffusing material having an absolute reflectance in a range from about thirty-five percent to about ninety percent.

44. An optical property calibration system for apparatus for measuring an optical property of a single thickness sheet material, the apparatus comprising receiving means having a common area for receiving a single thickness sheet material having a fluorescent constituent, a single light source, reflectance measuring photometric sensing means, light path means including a reflectance light path, and operable for directing light energy in a visible band and in a fluorescent producing band from the light source to the reflectance measuring photometric sensing means via said common area of the receiving means, and light spectrum control means for controlling the spectrum of light energy so directed to the common area of the receiving means from the single light source and operable for producing by means of the reflectance measuring photometric sensing means a first reflectance signal substantially exclusive of any fluorescent contribution, for partially characterizing the optical property substantially exclusive of the fluorescent contribution, the light path means being further operable for directing the fluorescence producing band of light energy to impinge on the receiving means for producing by means of the reflectance measuring photometric sensing means a second reflectance signal comprised of a fluorescent contribution to the optical property, and the light path means simultaneously providing a transmittance light path such that the light path means provides simultaneously operative reflectance and transmittance light paths each including a common incident light path extending from the single light source to the common area of the receiving means, the reflectance and transmittance light paths being respectively arranged for collecting light from the common area of the receiving means after impingment on single sheet material thereat, said optical property calibration system comprising an optical window member forming part of the simultaneously operative reflectance and transmittance light paths, and processing means for receiving the output of the reflectance measuring photometric sensing means in the absence of sheet material at the receiving means and operable for storing a reflectance parameter in accordance with the reflectance of said optical window member exclusive of any material for use in calibration of the optical property measurements of the apparatus.

45. A calibration system for apparatus for measuring an optical property of material, said apparatus comprising an optical measuring system including light source means, material receiving means for receiving light energy therefrom, photometric sensor means for receiving light energy from the material receiving means for providing respective reflectance and transmittance output signal components as a function of respective reflectance and transmittance parameters of material at the material receiving means, and further means operable in conjunction with said photometric sensor means for providing a quantitative output based on the reflectance and transmittance output signal components for characterizing the optical property, said optical property calibration system comprising an optical window member of substantial absolute reflectance disposed in optical coupling relation to said material receiving means during the sensing of the reflectance and transmittance parameters of material at said material receiving means, said optical window member in conjunction with said light source means and said photometric sensor means providing said reflectance output signal component and said transmittance output signal component, both with material at the material receiving means and without material at the material receiving means, and processing means for providing calibration values for the optical property with respect to the optical window member alone based on the reflectance and transmittance output signal components obtained from the photometric sensor means without material at the material receiving means.

* * * * *